United States Patent
Beauregard et al.

(10) Patent No.: US 10,788,477 B2
(45) Date of Patent: Sep. 29, 2020

(54) POLYMER PROBES AND METHODS

(71) Applicants: Buckman Laboratories International, Inc., Memphis, TN (US); Universite du Quebec a Trois-Rivieres, Trois-Rivieres (CA)

(72) Inventors: Marc Beauregard, Drummondville (CA); Fatma Meddeb-Mouelhi, Trois-Rivieres (CA); Yannick Hebert-Ouellet, Trois-Rivieres (CA); Bernard Janse, Collierville, TN (US); Kevin J. MacDonald, Middle Sackville (CA)

(73) Assignees: BUCKMAN LABORATORIES INTERNATIONAL, INC., Memphis, TN (US); UNIVERSITE DU QUEBEC A TROIS-RIVIERES, Quebec (CA)

( * ) Notice: Subject to any disclaimer, the term of this patent is extended or adjusted under 35 U.S.C. 154(b) by 607 days.

(21) Appl. No.: 15/332,588

(22) Filed: Oct. 24, 2016

(65) Prior Publication Data
US 2017/0115267 A1    Apr. 27, 2017

Related U.S. Application Data

(60) Provisional application No. 62/246,231, filed on Oct. 26, 2015.

(51) Int. Cl.
| | | |
|---|---|---|
| G01N 33/34 | (2006.01) | |
| G01N 33/53 | (2006.01) | |
| D21H 23/76 | (2006.01) | |
| C07K 14/00 | (2006.01) | |

(52) U.S. Cl.
CPC ......... *G01N 33/343* (2013.01); *C07K 14/001* (2013.01); *D21H 23/76* (2013.01); *G01N 33/5308* (2013.01); *G01N 2400/26* (2013.01)

(58) Field of Classification Search
None
See application file for complete search history.

(56) References Cited

U.S. PATENT DOCUMENTS

| | | | |
|---|---|---|---|
| 5,670,623 | A | 9/1997 | Shoseyov et al. |
| 5,719,044 | A | 2/1998 | Shoseyov et al. |
| 5,738,984 | A | 4/1998 | Shoseyov |
| 5,837,814 | A | 11/1998 | Shoseyov et al. |
| 5,856,201 | A | 1/1999 | Shoseyov et al. |
| 5,928,917 | A | 7/1999 | Kilburn et al. |
| 5,962,289 | A | 10/1999 | Kilburn et al. |
| 6,174,700 | B1 | 1/2001 | Haynes et al. |
| 7,361,487 | B2 | 4/2008 | Alapuranen et al. |

OTHER PUBLICATIONS

Alvira P et al. Pretreatment technologies for an efficient bioethanol production process based on enzymatic hydrolysis: A review. 2010. Bioresource Technology. 101. 4851-4861. (Year: 2010).*
Young RA. Comparison of the properties of chemical cellulose pulps. 1994. Cellulose. 1. 107-130. (Year: 1994).*
Blake AW et al. Understanding the Biological Rationale for the Diversity of Cellulose-directed Carbohydrate Modules in Prokaryotic Enzymes. 2006. The Journal of Biological Chemistry. vol. 281, No. 39. pp. 29321-29329. (Year: 2006).*
Day RN et al. The fluorescent protein palette: tools for cellular imaging. 2009. Chem. Soc. Rev. 38(10):2887-2921 (Year: 2009).*
Boraston et al., "Carbohydrate-binding modules: tine-tuning polysaccharide recognition", Biochemical Journal, vol. 382, 2004, pp. 769-781.
Christiansen et al., "The carbohydrate-binding module family 20-diversity, structure, and function", FEBS Journal, vol. 276, 2009, pp. 5006-5029.
Deddish et al., "Detection of Polysaccharide, Teichoic Acid, and Protein Antigens in Bacterial Colonies on an Agar Surface", Journal of Bacteriology, vol. 97, No. 3, Mar. 1969, pp. 1352-1356.
Rubin, Edward M., "Genomics of cellulosic biofuels", Nature, vol. 454, Aug. 14, 2008, pp. 841-845.
Hilden et al., "Use of a fluorescence labelled, carbohydrate-binding module from Phanerochaete chrysosporium Cel7D for studying wood cell wall ultrastructure", Biotechnology Letters, vol. 25, 2003, pp. 553-558.
Pettersson et al., "Characterization of pulp fiber surfaces by lignin specific antibodies", Nordic Pulp and Paper Research Journal, vol. 3, No. 3, 1988, pp. 152-155.
Shoseyov et al., "Carbohydrate Binding Modules: Biochemical Properties and Novel Applications", Microbiology and Molecular Biology Reviews, vol. 70, No. 2, Jun. 2006, pp. 283-295.

(Continued)

*Primary Examiner* — Paul J Holland
(74) *Attorney, Agent, or Firm* — Kilyk & Bowersox, P.L.L.C.

(57) ABSTRACT

A polymer detection probe is provided that includes a binding module that specifically binds to at least one polymer and a reporter module that is spectroscopically detectable. The binding module can be a carbohydrate-binding module (CBM). The reporter module can be a fluorescent protein. A complex is provided that includes a probe specifically bound to a pulp or paper product including at least one surface available lignocellulosic polymer. A pulp or paper product is provided that includes at least one surface available lignocellulosic polymer and at least one probe bound thereto. Methods are provided that employ a lignocellulosic probe. A method of detecting a lignocellulosic polymer or other type of polymer is provided. A method of determining the effectiveness of an industrial treatment on pulp or a paper product is also provided. A method of determining a physical property of pulp or a paper product is further provided.

46 Claims, 30 Drawing Sheets
Specification includes a Sequence Listing.

(56) References Cited

OTHER PUBLICATIONS

International Search Report and Written Opinion issued in corresponding International Patent Application No. PCT/US2016/058464, dated Jan. 23, 2017 (15 pages).

* cited by examiner

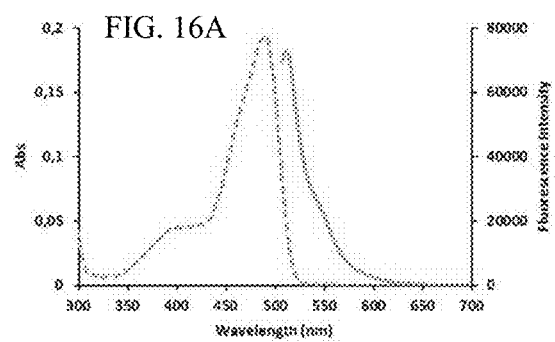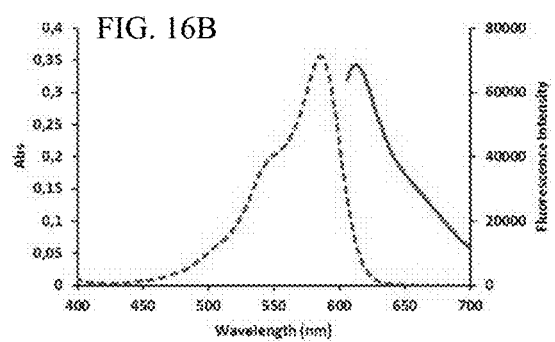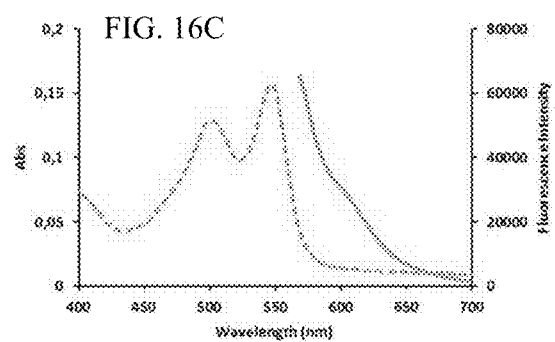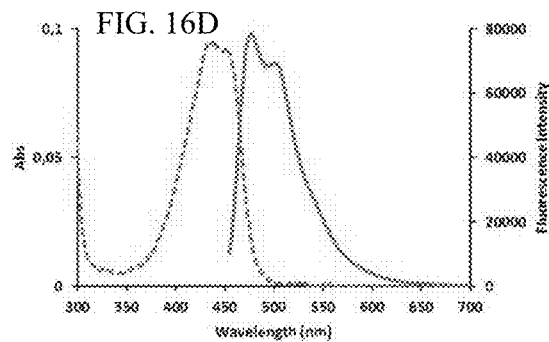

POLYMER PROBES AND METHODS

This application claims the benefit under 35 U.S.C. § 119(e) of prior U.S. Provisional Patent Application No. 62/246,231, filed Oct. 26, 2015, which is incorporated in its entirety by reference herein.

BACKGROUND OF THE INVENTION

The present invention relates to detection, characterization, and quantification of specific polymers, for example, lignocellulosic polymers such as polysaccharides, in biomass, and further relates to detection of any polymer, such as oligosaccharides, for instance, for a variety of uses as described herein.

In the field of pulp and papermaking, industries rely on a number of physical, chemical, and biological treatments to enhance the value of their product. Treatments include, for example, mechanical shearing (refining) of the fibers to help develop desired paper properties. Currently, there is no practical way to predict the outcome of such treatments without a thorough analysis of pulp and paper properties. Such an analysis involves pilot or industrial scale trials that are costly and time-consuming.

Current methods for polymer detection and fiber surface characterization include, for example, X-ray photoelectron spectroscopy (XPS), scanning electron microscopy (SEM); time-of-flight secondary ion mass spectrometry (ToF-SIMS) and Fourier transform infra-red (FTIR). These techniques involve specialized equipment, specific expertise, and lengthy manipulation and interpretation. These techniques also do not distinguish between cellulose and hemicellulose. Other approaches have been developed for indirect detection of polymers based on the use of dyes, for example, acrydin orange and phenanthren. They have been successfully used for studying plant cell morphology, but they employ sophisticated microscopes and are not quantitative. Still other techniques detect hemicellulose using antibodies raised against representative molecules. However, such antibodies are expensive and only detect a segment of polymers that resemble the molecules used for antibody production. If the exact epitope recognized by a particular antibody is not found or accessible, then the polymers will not be detected. Antibody techniques are lengthy and also involve use of secondary antibodies.

Carbohydrate binding modules (CBMs) are a group of molecules specialized for biomass polymer detection. CBMs are proteins optimized for specific detection of various targets, for example, carbohydrates such as crystalline cellulose and xylan. In order to detect binding of such CBM to biomass, one can attach a reporter dye to it. Such techniques involve microscopy. However, none of these methods have been successfully used for rapid characterization of fiber surface polymers that would enable the prediction of the impact of various treatments on pulp or paper.

Accordingly, there is a need for better materials and methods for detecting lignocellulosic polymers in biomass, and for the detection, in general, of polymers, such as oligosaccharides, in various applications.

SUMMARY OF THE PRESENT INVENTION

A feature of the present invention is to provide materials and methods for detecting and measuring lignocellulosic polymers in biomass, such as in a time and cost effective manner.

Another feature of the present invention is to provide materials and methods for determining the effectiveness of industrial treatments on pulp or paper before, during, and/or after a particular treatment is applied.

A further feature of the present invention is to provide materials and methods for determining a physical property of pulp or a paper product indirectly based on the presence and/or content of lignocellulosic polymers in the pulp or the paper product.

An additional feature of the present invention is to provide materials and methods for simultaneously measuring the presence and/or amounts of multiple, different lignocellulosic polymers in biomass independent of separate or sequential testing procedures.

A further feature of the present invention is to provide materials and methods for detection of any polymer, such as one or more oligosaccharides.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention, in part, relates to a lignocellulosic polymer detection probe including a binding module that specifically binds at least one lignocellulosic polymer and a reporter module that is spectroscopically detectable. Either or both of the modules can include a polypeptide. The binding module can be a carbohydrate-binding module (CBM). The reporter module can be a fluorescent protein. The probe can contain a plurality of probes with each probe specific to a particular lignocellulosic polymer and each probe containing a unique fluorescent spectral profile.

The present invention also relates to a complex including a probe specifically bound to a pulp or paper product including at least one surface available lignocellulosic polymer.

The present invention further relates to a pulp or paper product including at least one surface available lignocellulosic polymer and at least one probe specifically bound thereto.

The present invention also relates to method of detecting a lignocellulosic polymer. The method can include contacting the probe with a biomass material, and measuring a property associated with the reporter module to determine the presence or absence of at least one lignocellulosic polymer in the biomass material.

The present invention further relates to a method of determining the effectiveness of an industrial treatment on pulp or a paper product. A lignocellulosic polymer detection probe can be contacted with a pulp or a paper product. The specific binding of the probe to the pulp or the paper product can be detected. The amount of at least one lignocellulosic polymer on a surface of the pulp or the paper product can be calculated. The effectiveness or need of an industrial treatment on the pulp or paper product can be determined based on the amount of the at least one lignocellulosic polymer detected.

The present invention also relates to a method of determining a physical property of pulp or a paper product. A lignocellulosic polymer detection probe can be contacted with a pulp or a paper product. The specific binding of the probe to the pulp or the paper product can be detected. The amount of at least one lignocellulosic polymer on a surface of the pulp or the paper product can be determined (e.g., calculated). The at least one physical property of the pulp or paper product can be determined based on the amount of the at least one lignocellulosic polymer detected.

The present invention further relates to a polymer detection probe. The probe can have, for example, one or more characteristics or functions of the lignocellulosic polymer probes described herein, overlapping characteristics or functions, or different characteristics or functions. The polymer detection probe can include, for example, a binding module that specifically binds to at least one polymer (e.g., oligosaccharides or other saccharide polymers) and a reporter module that is spectroscopically detectable. A complex is provided including the probe specifically bound to a material including at least one surface available polymer.

The present invention also relates to a method of detecting a polymer (e.g., oligosaccharides or other saccharide polymers). A probe of the present invention can be contacted with a material. A property associated with the reporter module can be measured to determine the presence or absence of at least one polymer in the material based on specific binding of the probe to the at least one polymer. The detection or non-detection has a number of applications as described herein.

The materials and methods disclosed herein enable rapid and simultaneous detection of various lignocellulosic polymers at the surface of fibers used in pulp and paper, for example, cellulose and hemicellulose using fusion proteins. Signal patterns can be correlated to various changes in pulp and paper properties. The methods enable prediction of various treatments impact on paper properties. Such prediction allows for rapid and accurate choice of treatment, dosage, and/or other conditions for a given target, for example, conditions leading to a paper with higher burst index, a pulp with higher drainage rate, and/or the optimal xylanase concentration for bleaching boost. The methods enable optimal use of chemical, enzymatic, or physical treatments alike. The methods can be used in any industry based on wood biomass.

Further, the present invention has many applications. The effect of any relevant chemical, physical, or biological treatment that has an impact on fiber polymer exposure or distribution or hydrolysis on pulp and paper properties can be determined or predicted. For instance, an enzymatic sequence for optimizing pulp refining can be determined or predicted. Xylanase treatment for boosting bleaching can be optimized. Degradation of hemicelluloses when hydrolyzing biomass can be monitored. Production conditions for purified cellulosic materials, for example, nanocellulose or filaments, can be optimized by monitoring the presence of amorphous cellulose versus crystalline cellulose using the methods of the present invention.

It is to be understood that both the foregoing general description and the following detailed description are exemplary and explanatory only and intended to provide a further explanation of the present invention, as claimed.

BRIEF DESCRIPTION OF DRAWINGS

FIGS. 16A-16D are examples of graphs of excitation (dashed) and emission (full) spectra of the FP-CBM proteins for probes 1, 2b, 3, and 4, respectively.

DETAILED DESCRIPTION OF THE PRESENT INVENTION

Figure 1:
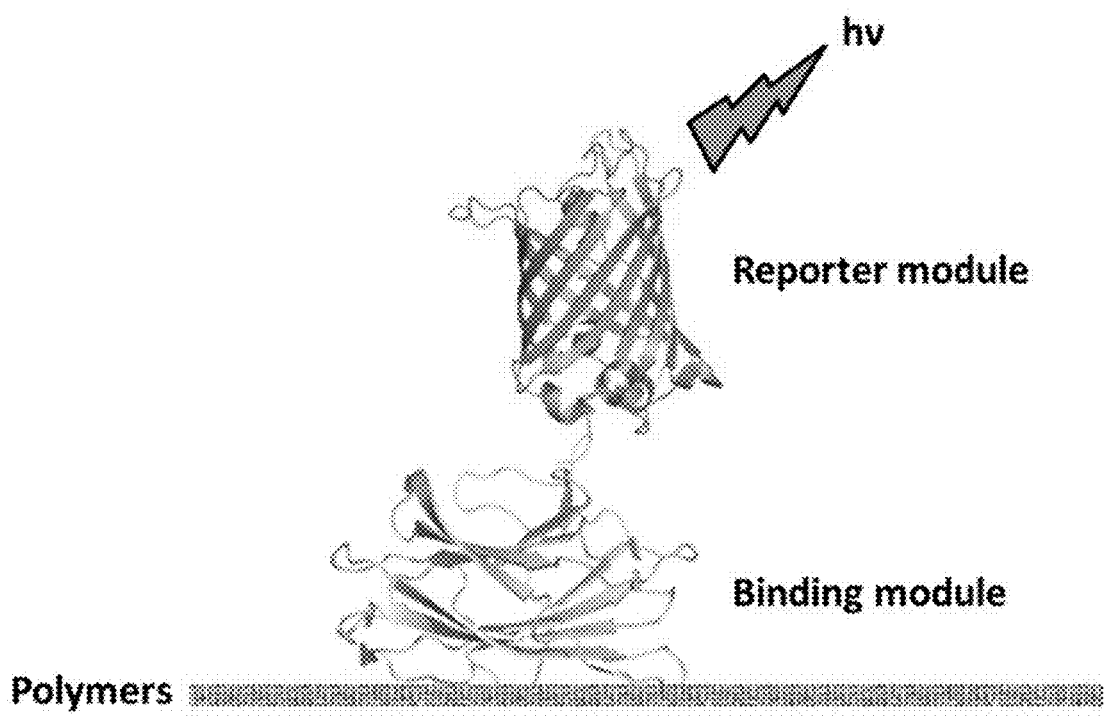
FIG. 1 is a schematic depiction of an example of polymer detection using the probes of the present invention.
Figure 2:
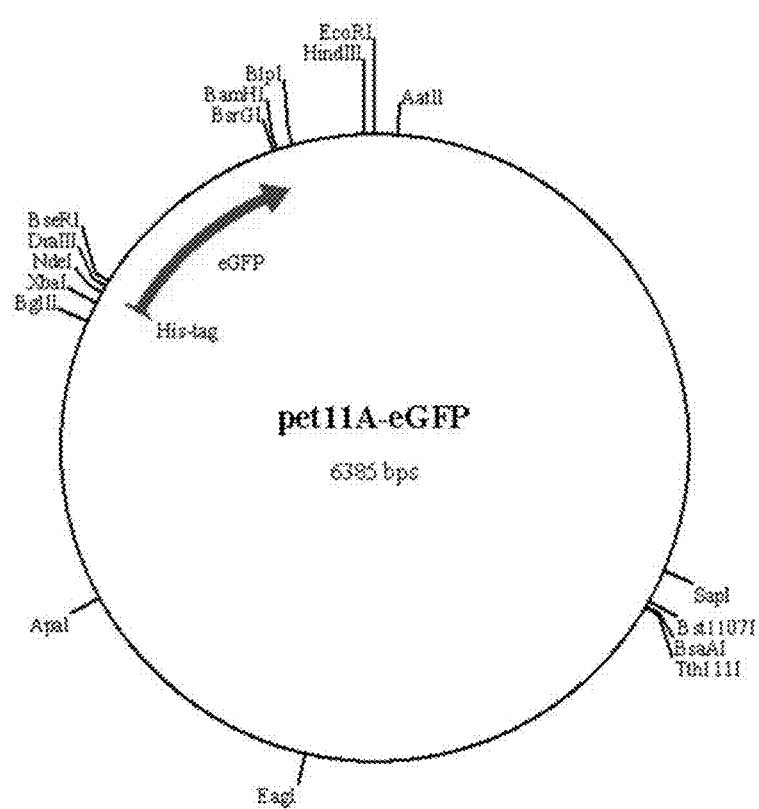
FIG. 2 is a schematic diagram of an expression vector of the pet11A-eGFP (eGFP reporter module).
Figure 3:
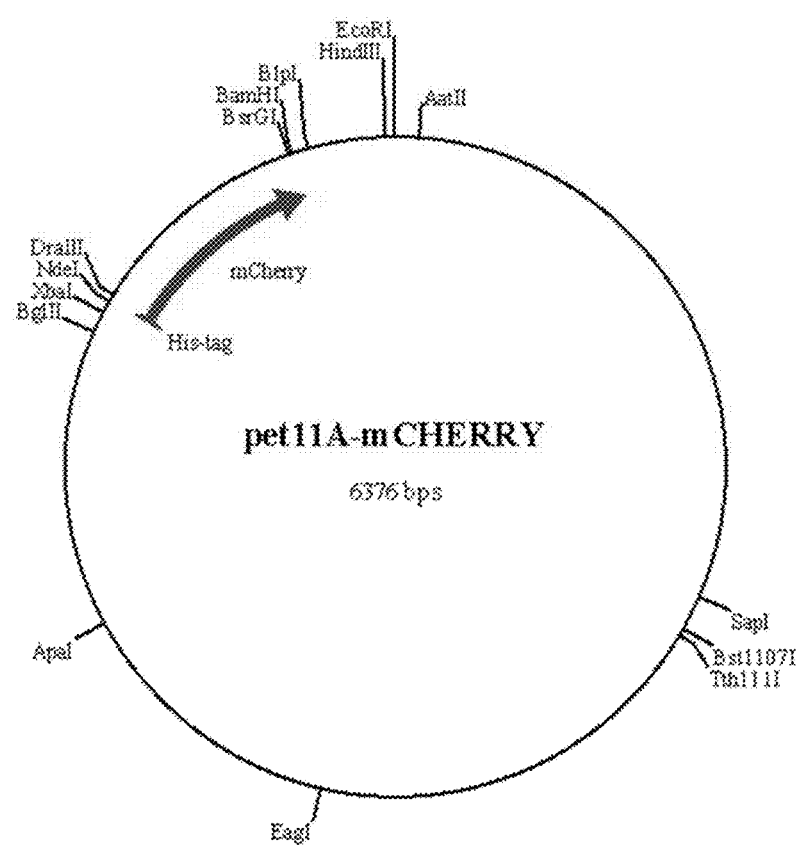
FIG. 3 is a schematic diagram of an expression vector of the pet11A-mCherry (mCherry reporter module).
Figure 4:
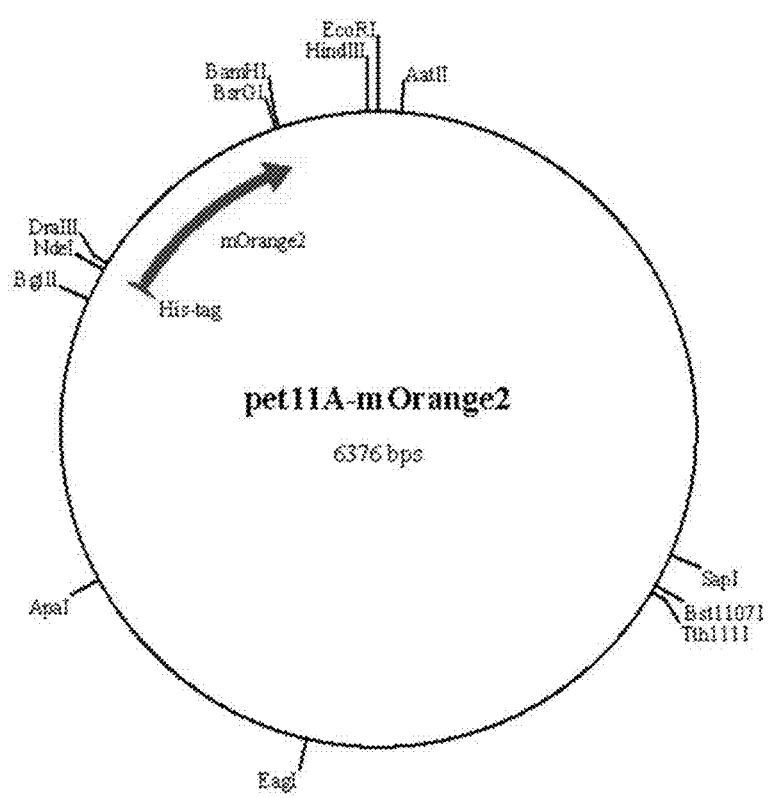
FIG. 4 is a schematic diagram of an expression vector of the pet11A-mOrange2 (mOrange2 reporter module).
Figure 5:
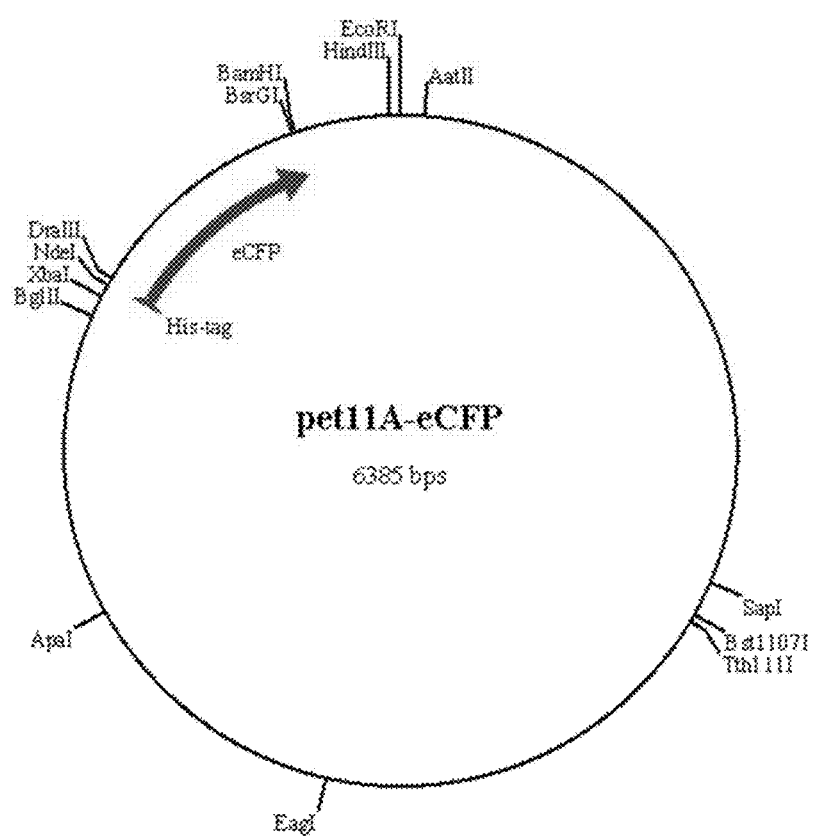
FIG. 5 is a schematic diagram of an expression vector of the pen 1A-eCFP (eCFP reporter module).

The present invention in part relates to a lignocellulosic polymer detection probe including a) a binding module that specifically binds to at least one lignocellulosic polymer and b) a reporter module that is spectroscopically detectable. Any suitable binding module and reporter module can be employed. A given probe can vary with respect to the number and/or kind of binding module and reporter module. A probe can contain a single binding module and a single reporter module. A probe can contain more binding modules than reporter modules, more reporter modules than binding modules, or an equal number of binding modules and reporter modules. A probe can contain from one to three, one to five, one to ten, or more binding modules and/or reporter modules. Each binding module can specifically bind a particular lignocellulosic polymer or a particular subset of lignocellulosic polymers.

The lignocellulosic polymer detection probe can include at least one probe polypeptide. All or part of a probe can be constructed from a polypeptide(s). Polypeptides are understood to contain proteins including the standard twenty amino acids modified in whole or part. One or more non-standard amino acids can replace or be used in addition to one or more standard amino acids. The polypeptides can be constructed by chemical synthesis or using molecular biological expression systems whether in vitro or in vivo. Any suitable expression system can be employed, for example, prokaryotic expression systems, eukaryotic expression systems, plasmid based expression systems, chromosomally integrated expression systems, or any combination thereof. Modification can be done synthetically, via post-translation modification in an expression system, or both. Any suitable modification can be employed, for example, phosphorylation, sulfonation, fluorination, acetylation, addition of carbohydrate groups, addition of lipid groups, addition of nucleic acids, addition of polynucleotides, addition of other amino acids, addition of other polypeptides, addition of synthetic organic molecules, addition of inorganic groups, or any combination thereof.

The binding module can be or include a binding module polypeptide. The reporter module can be or include a reporter module polypeptide. The binding module and reporter module polypeptide can be directly or indirectly connected to each other. For example, the binding module polypeptide can be fused directly to the reporter module polypeptide. The binding module polypeptide can be linked to the reporter polypeptide covalently, for example, via a linker polypeptide. The linker can be of any suitable length, for example, at least one amino acid, from 2 to about 2,000 amino acids (residues), from about 5 to about 1,000 amino acids, from about 10 to about 500 amino acids, from about 25 to about 250 amino acids, from about 50 to about 100 amino acids, or more than 2,000 amino acids. The linker can include a molecule other than or in addition to a polypeptide, for example, a carbohydrate, a polynucleotide, a lipid, a synthetic organic small molecule, a non-naturally occurring polymer, a metal, or any combination thereof. For example, the binding module and reporter module can be cross-linked using formaldehyde, glutaraldehyde, or both. The connection or attachment between the binding module and the reporter module can be an ionic bonding, hydrogen bonding, hydrophobic interactions, hydrophilic interactions, solvent-excluding interactions, or any combination thereof. The connection or attachment can include at least a covalent bond to ensure that the reporter module is tethered or otherwise stably attached to the binding module.

The probe polypeptide can be or include, for example, an amino acid sequence of any one of SEQ ID NOS: 2, 6, 8, 10, and 12, or a combination thereof; encoded by a nucleic acid sequence of SEQ ID NOS: 1, 5, 7, 9, and 11, respectively. The binding module polypeptide can be or include, for example, an amino acid sequence of any one of SEQ ID NOS: 14, 16, 18, 20, and 22; encoded by a nucleic acid sequence of 13, 15, 17, 19, and 21, respectively. The reporter module polypeptide can be or include, for example, an amino acid sequence of any one of SEQ ID NOS: 24, 26, 28, and 30; encoded by a nucleic acid sequence of 23, 25, 27, and 29, respectively. Histidine tag sequences can be omitted from the sequences for the probes, binding modules, and/or reporting modules, for example, if purification methods do not employ a nickel column.

The probes of the present invention are advantageous as they can function independent of, without including, or without using an antibody or a polypeptide including an antigen-binding fragment of an antibody. Neither the binding module polypeptide nor the reporter module need be or include an antibody or a fragment thereof. Either the binding module polypeptide or the reporter module can be or include an antibody or a fragment thereof. Both the binding module polypeptide and the reporter module can be or include an antibody or a fragment thereof. Even if a binding module is not an antibody or antigen-binding fragment thereof, the binding module can still bind a target with the specificity of an antibody. The binding of the binding module to its target lignocellulosic can occur under conditions similar to or different from the binding of an antibody to its antigen. Binding can be performed under any suitable conditions that increase specific binding of a binding module to its desired target(s), and decrease, minimize, or prevent non-specific binding of the binding module to non-targets. Binding can be assisted by the presence of one or more additional factors, for example, probe concentration, ions, for example calcium ions, ionic strength, pH, and/or temperature, and the like. Both, neither, or just one of the binding module and reporter module can be or include a polypeptide of any kind. Binding modules and/or reporter modules can be or include nucleotides, carbohydrates, lipids, synthetic organic groups, and/or inorganic groups instead of or in addition to polypeptides. For example, polynucleotides, polysaccharides, fatty acids, esters, sterols, and/or non-naturally occurring polymers can be used. Binding modules and/or reporter modules and/or other portions of a probe can contain any suitable type or number of molecules, for example, molecules described herein.

Any suitable reporter module or combination of reporter modules can be used in the probes and methods of the present invention. For example, the reporter module in whole or part can be fluorescent. The reporter module can have any suitable fluorescent excitation and emission spectra. The reporter module can have a unique excitation spectrum and/or excitation peak maximum. For example, the reporter module can have a fluorescence excitation peak (maximum) of, for example, lower than 300 nm, from about 300 nm to about 750 nm, from about 350 nm to about 700 nm, from about 400 nm to about 650 nm, from about 350 nm to about 400 nm, from about 400 nm to about 450 nm, from about 450 nm to about 500 nm, from about 500 nm to about 550 nm, from about 550 nm to about 600 nm, from about 600 nm to about 650 nm, from about 650 nm to about 700 nm, greater than 700 nm or any intervening range (for example, a 1-3 nm, 5 nm, 10 nm, or 25 nm range) or value. The reporter module can have a unique emission spectrum (±1 nm, or ±3 nm, or ±5 nm) and/or emission peak maximum (±1 nm, or ±3 nm, or ±5 nm). For example, the reporter module can have a fluorescence emission peak (maximum) of less than 350 nm, from about 350 nm to about 800 nm, from about 400 nm to about 750 nm, from about 450 nm to about 700 nm, from about 350 nm to about 400 nm, from about 400 nm to about 450 nm, from about 450 nm to about 500 nm, from about 500 nm to about 550 nm, from about 550 nm to about 600 nm, from about 600 nm to about 650 nm, from about 650 nm to about 700 nm, from about 700 nm to about 750 nm, greater than 750 nm, or any intervening range (for example, a 1-3 nm, 5 nm, 10 nm, or 25 nm range) or value.

The reporter module can include any number or type of fluorescent moieties. For example, the fluorescent moiety can be or include a polypeptide, a polynucleotide, a polysaccharide, a small organic molecule, a metal, a coordination complex, or any combination thereof. For example, the reporter module can be or include a fluorescent protein or a combination of fluorescent proteins. The fluorescent protein can be or include an ultraviolet fluorescent protein, a blue fluorescent protein, a cyan fluorescent protein, a green fluorescent protein, a yellow fluorescent protein, an orange fluorescent protein, a red fluorescent protein, a far-red fluorescent protein, a near infrared fluorescent protein, an infrared fluorescent protein, a sapphire-type fluorescent protein, a long Stokes shift fluorescent protein, a switchable fluorescent protein, or any combination thereof. The fluorescent protein can be or include, for example, Sirius, TagBFP, mTagBFP2, Azurite, EBFP2, mKalama1, Sirius, Sapphire, T-Sapphire, ECFP, mAmetrine, Cerulean, mCerulean3, SCFP3A, CyPet, mTurguoise, mTurquoise2, monomeric Midoriishi-Cyan, Aquamarine, eCFP, TagCFP, mTFP1, AmCyan1, EGFP, Emerald, Superfolder GFP, monomeric Azami Green, TurboGFP, TagGFP2, mUKG, mWasabi, Clover, mNeonGreen, eGFP, AcGFP1, ZGreen1, ZsYellow1, mBanana, EYFP, Topaz, Citrine, Venus, SYFP2, Ypet, IanRFP-deltaS83, mPapaya1, TagYFP, mOrange, mOrange2, monomeric Kusabira-Orange, mKOk, mKO2, mTangerine, mNectarine, TagRFP, TagRFP-T, mApple, mRuby, mRuby2, DsRed-Express2, DsRed-Express, tdTomato, DsRed-Monomer, DsRed-Monomer, DsRed2, AsRed2, mStrawberry, mCherry, HcRed1, FusionRed, mRaspberry, E2-Crimson, mPlum, HcRed-Tandem, mKate2, mNeptune, NirFP, TagRFP657, TagRFP675, iFP1.4, iRFP(iRFP713), iRFP670, iRFP682, iRFP702, iRFP720, iFP2.0, mIFP, mKeima Red, LSS-mKate1, LSS-mKate2, LSSmOrange, mBeRFP, PA-GFP, PATag RFP, Dendra2, Timer, PAmCherry, Kaede (green), Kaeda (red), KikGR1 (green), KikGR1 (red), PS-CFP2, mEos2 (green), mEos2 (red), mEos3.2 (green), mEos3.2(red), PSmOrange, Dropna, or any combination thereof. Reporter modules other than fluorescent reporter modules can be employed in addition to or in the alternative to fluorescent reporter modules. For example, antibodies, antibody fragments, radioisotopes, dyes, synthetic organic molecules, phosphorescent molecules, enzymes, or the like, or any combination thereof can be used. Reporter modules described in Knox P. J. (2012) Methods in Enzymology, volume 510, 233-245, which is incorporated by reference herein in its entirety, can be used. The accessible primary amines of binding modules, for example, CBMs, can be labelled using a reactive dye that contains a tetrafluorophenyl ester moiety (Invitrogen).

Any suitable binding module or combination of binding modules can be used in the probes and methods of the present invention. For example, the binding module can be or include a carbohydrate-binding module (CBM) including CBM1, CBM2, CBM3, CBM3a, CBM4, CBM5, CBM6, CBM7, CBM8, CBM9, CBM10, CBM11, CBM12, CBM13, CBM14, CBM15, CBM16, CBM17, CBM18, CBM19, CBM20, CBM21, CBM22, CBM23, CBM24, CBM25, CBM26, CBM27, CBM28, CBM29, CBM30, CBM31, CBM32, CBM33, CBM34, CBM35, CBM36, CBM37, CBM38, CBM39, CBM40, CBM41, CBM42, CBM43, CBM44, CBM45, CBM46, CBM47, CBM48, CBM49, CBM50, CBM51, CBM52, CBM53, CBM54, CBM55, CBM56, CBM57, CBM58, CBM59, CBM60, CBM61, CBM62, CBM63, CBM64, CBM65, CBM66, CBM67, CBM68, CBM69, CBM70, CBM71, or a family member thereof, or any combination thereof. Binding specificities can be or include those of particular CBM families or specific CBM family members, for example, CBM1 (cellulose), CBM2 (cellulose), CBM3 (crystalline cellulose), CBM4 (amorphous cellulose), CBM5 (chitin), CBM6 (cello-oligosaccharides, laminarins, xylooligosaccharides, beta1,4,-beta1,3-mixed linked glucans), CBM8 (cellulose), CBM9 (crystalline cellulose), CBM10 (cellulose), CBM11 (cellulose), CBM12 (chitin), CBM13 (cellulose, xylans, mannose), CBM14 (chitin), CBM15 (xylans and xylooligosaccharides), CBM16 (cellulose and glucomannans), CBM17 (amorphous cellulose), CBM18 (chitin), CBM19 (chitin), CBM20 (starch), CBM21 (glycogen), CBM22 (mixed β-1,3/β-1,4-glucans), CBM23 (mannans), CBM24 (α-1,3-glucan), CBM25 (alpha-glucooligosaccharides and granular starch), CBM 26 (starch), CBM27 (beta-1,4-mannooligosaccharides, carob galactomannan, and konjac glucomannans, mannans), CBM28 (amorphous cellulose, cellooligosaccharides, and β-(1,3)(1,4)-glucans), CBM29 (mannans and glucomannans), CBM30 (cellulose), CBM31 (β-1,3-xylans), CBM32 (galactose, lactose, polygalacturonic acid, and β-D-galactosyl-1,4-β-D-N-acetylglucosamine), CBM33 (chitin), CBM34 (granular starch), CBM35 (xylans, mannans, and β-galactans), CBM36 (xylans and xylooligosaccharides), CBM37 (xylans, chitin, microcrystalline cellulose, and phosphoric-acid swollen cellulose), CBM38 (inulin), CBM39 (β-1,3-glucan, lipopolysaccharide, and lipoteichoic acid) CBM48 (glycogen), CBM40 (sialic acid), CBM 41 (α-glucans, amylose, amylopectin, and pullulans), CBM42 (arabinofuranose and arabinoxylans), CBM43 (β-1,3-glucans), CBM44 (cellulose and xyloglucans), CBM45 (starch), CBM46 (cellulose), CBM47 (fucose), CBM48 (glycogens), CBM49 (crystalline cellulose), CBM50 (chitin and chitopentaose), CBM51 (galactose and A/B blood group antigens), CBM52 (β-1,3-glucans), CBM53 (starch), CBM54 (xylans), CBM55 (chitin), CBM56 (β-1,3-glucans), CBM58 (maltoheptaose), CBM59 (mannans, xylans, and cellulose), CBM60 (xylans), CBM61 (β-1,4-galactans), CBM62 (galactose, xyloglucans, arabinogalactans, and galactomannans), CBM63 (cellulose), CBM64 (cellulose), CBM65 (xyloglucans), CBM66 (fructans), CBM67 (L-rhamnose), CBM68 (maltotriose and maltotetraose), CBM69 (starch), CBM70 (hyaluronan), CBM71 (lactose and β-D-galactosyl-1,4-β-D-N-acetylglucosamine), or any combination thereof. Any suitable carbohydrate binding module can be employed, for example, as described in Boraston et al., Biochem J., 382: 769-781 (2004), Shoseyov et al., Microbiology and Molecular Biology Reviews, 70(2): 283-295 (2006) or Christiansen et al., FEBS Journal, 276:5006-5029 (2009). CBMs or other binding modules can be synthetically or genetically evolved or otherwise generated to bind to any desired target whether carbohydrates, other types of polymers, or non-polymer compounds. Techniques such as phage display, for example, can be used. For example, CBMs can be produced that bind to polymers, for example, a polyaryletherketone (PAEK), a polyether ether ketone (PEEK), a polyethylene, a polypropylene, a polystyrene, a polytetrfluoroethylene, a polyvinylchloride, a polyamide, a para-aramid, a polyethylene terephthalate, a polyimide, a polycarbonate, a polypeptide, a polynucleotide, a glycoprotein, a protein, a phosphorylated protein, a modified protein, a lipid, a surfactant, lecithin, or a biosurfactant, or any combination thereof. The CBMs can be replaced by antibodies and the detection method can be tailored for antibodies. See, for example, Knox P. J. (2012) Methods in Enzymology, volume 510, 233-245, which is incorporated by reference herein in its entirety.

A binding module can bind specifically to any desired polymer (e.g., lignocellulosic polymer or combination thereof, or any oligosaccharide). For example, the binding module can specifically bind to cellulose, hemicellulose, lignin, xylan, mannan, glucuronoxylan, arabinoxylan, glucomannan, xyloglucan, or any combination thereof or a linear fragment thereof, or a branched fragment thereof, or an oligomer thereof (for example, an oligosaccharide), or a monomer and/or macromer thereof, for example, glucose, D-glucose, mannose, xylose, galactose, rhamnose, arabinose, monolignol, p-coumaryl alcohol, coniferyl alcohol, sinapyl alcohol, p-hydroxyphenyl phenylpropanoid, guaiacyl phenylpropanoid, syringyl phenylpropanoid, or a combination thereof. The binding module can bind to an amorphous or crystalline lignocellulosic polymer. The binding module can recognize both an amorphous and crystalline form of a particular lignocellulosic polymer or be specific to one or the other. For example, the binding module can specifically bind to crystallized cellulose (and not to amorphous cellulose). A binding module can specifically bind to amorphous cellulose (and not to crystallized cellulose).

The lignocellulosic polymer detection probe can include a plurality of lignocellulosic polymer detection probes, each lignocellulosic polymer detection probe binding solely or essentially solely to a different lignocellulosic polymer. The plurality of probes can include any number or kind of probes. For example, a plurality can include at least two probes, at least three probes, at least four probes, at least five probes, at least ten probes, from two probes to twenty probes, from two probes to ten probes, or from two probes to four probes. A plurality of probes can be provided as a pre-formulated composition or combined from separate stock solutions of individual probes. The concentration, for example, weight percentage, of each probe in a composition can be the same or differ between types of probes based on the total weight of the composition. For example, the weight ratio of probes in a composition including four different types of probes could be 1:1:1:1, or some other ratio. The relative amounts, ratio, and/or concentration of probes can be adjusted based on the lignocellulosic polymer profile of a particular biomass.

A probe composition can include various other components, for example, one or more stabilizers, one or more preservatives, one or more emulsifiers, one or more thickeners, one or more diluents, or any combination thereof.

Each lignocellulosic polymer detection probe can include a different reporter module. For example, each reporter module can have a different (or unique) fluorescence signature. Any combination of fluorescent reporter modules can be used, for example, one or more of eGFP, mCherry, mOrange2, and eCFP. Any combination of binding modules can be used, for example, one or more of CBM3a, CBM4-1, CBM15, and CBM27. A plurality of probes can be provided such that each binding module is paired with a unique reporter module and vice versa. For example, the lignocellulosic polymer detection probe can include eGFP-CBM3a, mCherry-CBM4-1, mOrange2-CBM15, eCFP-CBM27, or any combination thereof.

The lignocellulosic or any polymer detection probe of the present invention can be detectable at a distinct wavelength (±0.5 nm, ±1 nm, 3 nm, ±5 nm). Thus, a combination of different probes can be used and measured simultaneously, instead of using different probes separately or sequentially.

The present invention also relates to a complex including any probe or combination thereof bound to a pulp or paper product including at least one surface available lignocellulosic polymer. The present invention also relates to a pulp or paper product including at least one surface available lignocellulosic polymer and at least one probe bound thereto. The pulp can be any grade of pulp and a pulp at any stage of production of a paper or other biomass product. The pulp can include furnish. The pulp can include white water. The pulp can be or include product waste, for example, paper sludge. The pulp can be chemical pulp, mechanical pulp, thermomechanical pulp or chemi (thermo) mechanical pulp or a Kraft pulp. The pulp can be pulp from hardwood, softwood, or both types, or can include textile fibers, agricultural plant pulp, or the like. The pulp can be beached, pre-bleached, or unbleached. The pulp can be refined or unrefined. The paper product can be an intermediate paper product, a sample paper product useful for testing, or a finished paper product. Paper products can be, for example, printable or inkable paper sheets, sheets for cardboard construction, tissue paper, hygiene and personal care sheet or liner materials, or the like.

The present invention also is directed to various methods that employ lignocellulosic or any polymer detection probes. The methods can use any number or types of probes, for example a single probe or a plurality of probes. The present invention relates to a method of detecting a lignocellulosic polymer or any polymer. A probe can be contacted with a biomass material. This can be accomplished by introducing, adding, mixing, or otherwise combining the probe with the biomass material (e.g., pulp or paper product). Contacting can include and/or result in binding of the probe if its specific target lignocellulosic polymer or any polymer is present. A property associated with the reporter module can be measured to determine the presence or absence of at least one lignocellulosic polymer in the biomass material. For example, the property measured can be or include fluorescence. The method can also include calculating the amount of the at least one lignocellulosic polymer, determining the type of the at least one lignocellulosic polymer, or both.

The biomass material measured can be or include any suitable biomass material. The biomass material can be a raw material, a partially processed material, or a finished product. The biomass material can be or include a wood biomass material. The wood biomass material can be or include pulp, furnish, white water, paper, a paper product, paper sludge, or any combination thereof. The method can include forming at least one handsheet from the wood biomass product, wherein the measuring is performed on the handsheet.

The measuring can be performed before treatment, during treatment, and/or after treatment, or any combination thereof of the biomass material. The treatment can include, for example, an enzymatic treatment, bleaching, amorphogenesis, milling, or PFI refilling, or any combination thereof. The treatment can be or include, for example, enzymatic treatment with at least one enzyme including a cellulase, a xylanase, a mannase, a lignase, or any combination thereof. The method can be or include performing at least one treatment of the biomass material based on the amount of the at least one lignocellulosic polymer measured, the type of lignocellulosic polymer measured, or both. The amount of lignocellulosic polymer measured can correlate negatively or positively with at least one physical property of the biomass product. The at least one physical property can include, for example, burst index, drainage rate, tear index, tensile index, internal bond strength, or any combination thereof. The at least one physical property can include, for example, density, elastic modulus, shear modulus, Young's modulus, Poisson's ratio, yielding stress, ultimate stress, fiber length, elongation, or the like.

The amount of lignocellulosic polymer measured, the type of lignocellulosic polymer measured or both can be used to determine the amount or type of treatment to be applied to the biomass material. For example, the method can include dosing at least one enzyme based on the amount of lignocellulosic polymer measured, the type of lignocellulosic polymer measured or both. For example, if the amount of crystalline cellulose is relatively low, a greater amount of cellulase can be added. If the amount of lignin is high, for example, the amount of bleach can be increased. A high amount of xylan measured can be addressed, for example, by increasing the amount of xylanase added to the pulp. For pre-bleaching, for example, a measurement of high mannan content can be addressed by increasing the amount of mannase added to the pulp. The method can include adjusting mill speed based on the amount of lignocellulosic polymer measured, the type of lignocellulosic polymer measured or both. For example, if the amount of crystalline cellulose is relatively low, the intensity of refining (e.g., mill speed, in number of rpms) can be increased. The method can include adjusting total water content of the biomass material based on the amount of lignocellulosic polymer measured, the type of lignocellulosic polymer measured or both. For example, water can be added to the pulp if the amount of crystalline cellulose is relatively high and the amount of amorphous cellulose is relatively low. Thus, the method can be used to adjust the concentration of pulp or one or more components thereof.

The present invention further relates to a method of determining the effectiveness of an industrial treatment on pulp or a paper product. A lignocellulosic polymer detection probe can be contacted with or attached to a pulp or a paper product. The specific binding of the probe to the pulp or the paper product can be detected. The amount of at least one lignocellulosic polymer on a surface of the pulp or the paper product can be determined (e.g., calculated). The effectiveness of an industrial treatment on the pulp or paper product can be determined based on the amount of the at least one lignocellulosic polymer detected. The effectiveness of any suitable industrial treatment can be determined. The industrial treatment can be or include, for example, an enzymatic treatment, a chemical treatment, a physical treatment, or any combination thereof. The method can be performed before the industrial treatment, during the industrial treatment, after the industrial treatment, or any combination thereof. The polymer detection probe can be detectable at a distinct wavelength as part of the method. The method can be performed on paper waste, for example, paper sludge, and the industrial treatment can include a treatment for paper waste.

The present invention also relates to a method of determining a physical property of pulp or a paper product. A lignocellulosic polymer detection probe can be contacted with pulp or a paper product. The specific binding of the probe to the pulp or the paper product can be detected. The amount of at least one lignocellulosic polymer on a surface of the pulp or the paper product can be calculated. The at least one physical property of the pulp or paper product can be determined based on the amount of the at least one lignocellulosic polymer detected. The at least one physical property can be or include, for example, burst index, drainage rate, tear index, tensile index, or internal bond strength, or any combination thereof. The at least one physical property can be or include, for example, density, elastic modulus, shear modulus, Young's modulus, Poisson's ratio, yielding stress, ultimate stress, fiber length, or elongation, or the like.

The probes and methods of the present invention are applicable in applications other than pulp and paper processing. For example, the probes and methods can be used for environmental compliance and/or monitoring. The probes and methods can be used, for example, in the food industry to track the types and/or amounts of carbohydrates present during various stages of food production, and subsequently to detect food spoliation or other conditions or properties. The probes and methods can be used to track the presence and/or amounts of microbes or other cell types in any material. The probes and methods can be used to detect cell markers such as glycoproteins, for example, those characteristic of blood groups, cancers, or pathogens. The probes and methods can be used in medical contexts, for example, histology. The probes and methods of the present invention are applicable to any relevant sector of industrial production, food production/testing, agricultural applications, plastics, medicine, diagnostics, microbiology, biomass/biofuel, and/or petroleum production/testing, and the like.

A polymer detection probe, in general, is provided by the present invention. The probe can have, for example, one or more characteristics or functions of the lignocellulosic polymer probes described herein, overlapping characteristics or functions, or different characteristics or functions. The polymer detection probe can include, for example, a) a binding module that specifically binds to at least one polymer and b) a reporter module that is spectroscopically detectable. The polymer detection probe can be or include, for example, a probe polypeptide. The reporter module can be, for example, fluorescent. The reporter module can be or include a fluorescent protein. The binding module can be a carbohydrate-binding module (CBM). The binding module can specifically bind to, for example, cellulose, hemicellulose, lignin, xylan, mannan, glucuronoxylan, arabinoxylan, glucomannan, xyloglucan, or any combination thereof or a linear fragment thereof, or a branched fragment thereof, or an oligomer thereof, or a monomer and/or macromer thereof, for example, glucose, D-glucose, mannose, xylose, galactose, rhamnose, arabinose, monolignol, p-coumaryl alcohol, coniferyl alcohol, sinapyl alcohol, p-hydroxyphenyl phenylpropanoid, guaiacyl phenylpropanoid, or syringyl phenylpropanoid, or a combination thereof. The binding module can specifically bind to, for example, a glycoprotein, carbohydrate, or both, specific to a particular blood antigen, type, group, or subgroup.

The binding module can specifically bind to any particular polymer (e.g., oligosaccharide or other saccharide polymer or other polymer). The polymer can be naturally occurring or synthetic. The binding module can specifically bind to, for example, a polyaryletherketone (PAEK), a polyether ether ketone (PEEK), a polyethylene, a polypropylene, a polystyrene, a polytetrfluoroethylene, a polyvinylchloride, a polyamide, a para-aramid, a polyethylene terephthalate, a polyimide, a polycarbonate, a polypeptide, a polynucleotide, a glycoprotein, a protein, a phosphorylated protein, a modified protein, a lipid, lecithin, a surfactant, or a biosurfactant, or any combination thereof or a material including or containing one or more of these polymers. The polymer detection probe can include a plurality of polymer detection probes, each polymer detection probe specifically binding to a different polymer. Each polymer detection probe can include a different reporter module. Each reporter module can have a different fluorescence signature. The polymer detection probe can be detectable at a distinct wavelength (±0.2 nm, ±0.5 nm, ±1 nm, ±3 nm, ±5 nm). A complex is provided including the probe specifically bound to a material including at least one surface available polymer. The manner in which the lignocellulosic polymer probe is designed and used (as described herein) can equally apply in general to the broader polymer probes of the present invention for any polymer and for the detection of that polymer that specifically binds to the probe.

A method of detecting a polymer (such as the classes and specific ones described earlier) is provided. A probe of the present invention can be contacted with a material. A property associated with the reporter module can be measured to determine the presence or absence of at least one polymer in the material based on specific binding of the probe to the at least one polymer. The property measured can be, for example, fluorescence. The method can include calculating the amount of the at least one polymer, determining the type of the at least one polymer, or both. The material can be or include a biological sample, for example, a cancer biopsy, cells, a tissue sample, a microbiological sample, or a blood sample. The presence or absence of a cancer and/or an identity of cancer type can be determined, for example, by using a binding module specific to a cancer cell surface marker, such as a glycoprotein. The presence or absence of a beneficial or pathogenic microorganism and/or an identify of a microorganism such as a virus or bacterium can be determined, for example, by using a binding module specific to a microorganism cell surface marker, such as a cell wall polysaccharide or a cell surface glycoprotein. At least one of a blood antigen, type, group, or subgroup of the blood sample can be determined. For example, types A, B, AB, and O can be distinguished in the ABO blood group system. An Rh antigen, such as the D antigen, can be detected in the Rh blood group system to determine whether a blood sample is Rh positive or negative. A plurality of probes, for example, different kinds of probes, can be used in the method. Thus, the ABO group and Rh factor identities of a blood sample, for example, can be determined simultaneously.

The present invention will be further clarified by the following examples, which are intended to be exemplary of the present invention.

EXAMPLES

The following examples demonstrate the utility of the present invention and its surprising advantages over existing techniques. Predictive methods, based on the use of CBMs fused to various fluorescent proteins, were created. Using molecular biology techniques and constructs, four different fusion proteins were created. Each of these "probes" is constructed of a specific binding module (the CBM moiety) and a reporter module (the fluorescent protein). Each probe emits fluorescence at a distinct wavelength, allowing for unambiguous detection of the polymer specifically bound by the binding module. FIG. 1 is a schematic diagram of polymer detection using a probe.

After production and characterization of the probes, they are demonstrated as specifically binding to relevant polymers, and change binding in response to change in surface availability of such polymers. Accordingly, these probes demonstrate that the present invention enables the detection of changes, and that the signal generate by the probes can be correlated with pulp and paper properties measured independently, with industry-standard methods. The method can be used to predict the impact of any industrial treatment on properties that depend on exposure of polymers. As demonstrated by these examples, the present invention can also be used for monitoring surface polymers at any stage for any process involving lignocellulosic biomass.

Table 1 lists CBMs, binding targets, and associated fluorophores. The emission wavelengths are separated by several nanometers, enabling detection of individual probes even when mixed with other probes (spectral deconvolution).

TABLE 1

| Probe # | CBM | Target | Fluorescent protein tag (Ex/Em) |
| --- | --- | --- | --- |
| 1 | CBM3a | Crystalline cellulose | eGFP (488/507) |
| 2a | CBM4-1 | Amorphous cellulose | mCherry (587/610) |
| 2b | CBM17 | Amorphous cellulose | mCherry (587/610) |
| 3 | CBM15 | Xylan | mOrange2 (549/565) |
| 4 | CBM27 | Mannar | eCFP (434/477) |

Probe 1 detects, for example, crystalline cellulose (CBM3a-eGFP) and fluoresces at 507 nm. Probe 2a detects, for example, amorphous cellulose (CBM4-1-mCherry) and emits fluorescence at 610 nm. Probe 2b (CBM17-mCherry) also detects amorphous cellulose, but with a higher affinity compared to Probe 2a. CBM15 fused to mOrange2 detects xylan (Probe 3) and is visible at 565 nm. Probe 4 includes CBM27 fused to eCFP and emits light at 477 nm. The probes emission maxima are separated, and can be detectable even when probes are mixed with others described here.

Example 1

This example demonstrates the production of reporter modules (fluorescent proteins) in accordance with the present invention. Four reporter modules (eCFP, eGFP, mCherry and mOrange2) were cloned in pET11 vector and expressed in prokaryotic systems. FIGS. 2-5 show the genetic maps of the respective reporter modules (fluorescent proteins) cloned into the pET11 vector. Nucleic acid and amino acid sequences for the reporter modules are shown in SEQ ID NOS: 23-30, respectively. These vector constructs are used for labeling binding modules from cloned genes with the reporter modules. Single fluorescent proteins (reporter modules) are used to measure the background (non-specific) binding to the pulp polymers.

Proteins were purified using the following methodology. E. coli BL21(DE3) GOLD pLysS cells (ThermoFisher Scientific) bearing the selected expression plasmid (reporter module, binding module or complete Probe) were grown at 37° C. in Luria-Bertani broth containing 100 µg/ml of ampicillin. Induction of recombinant protein expression was performed by the addition of 500 µM IPTG (ThermoFisher Scientific) to mid-log-phase cells (O.D. 600 nm of 0.6-0.8) and the subsequent incubation for 18 hours at 25° C. Cells were afterward harvested and kept at −80° C. Thawed cell pellets were resuspended in 50 mM $NaPO_4$ pH 8 containing 300 mM NaCl, 2 mM imidazole, and 1 mM PMSF, and then lysed using six cycles of 60 seconds of sonication (Branson Ultrasonics Corporation) at 200 W. Clarification of the lysate was achieved by centrifugation at 10,000 g for 30 minutes at 4° C.

The protein of interest was then purified by affinity chromatography over a HisPrep FF 16/10 column (GE Healthcare Life Sciences) equilibrated in 50 mM $NaPO_4$ pH 8.0 buffer containing 300 mM NaCl and 10 mM imidazole. Following a ten column volumes buffer washes, the desired protein was eluted following a ten column volumes gradient of imidazole (10 to 100 mM) in 50 mM $NaPO_4$ pH 8.0 buffer containing 300 mM NaCl. A final purification step was performed over a SUPERDEX 200 HR 16/50 column (GE Healthcare Life Sciences) in 50 mM Tris-HCl pH 7.5 buffer containing 300 mM NaCl to insure its homogenous purify. The purified probe was then dialyzed in a 20 Tris-HCl pH 7.5 buffer containing 20 mM NaCl and 5 mM $CaCl_2$ at 4° C. and concentrated using a 10k MACROSEP Advance centrifugal device (Pall Corporation). Concentrated protein solutions were stored at −80° C. using flash freezing. Protein purity was verified by SDS-PAGE. The amount of protein was quantified by the Bradford method.

Figure 6:
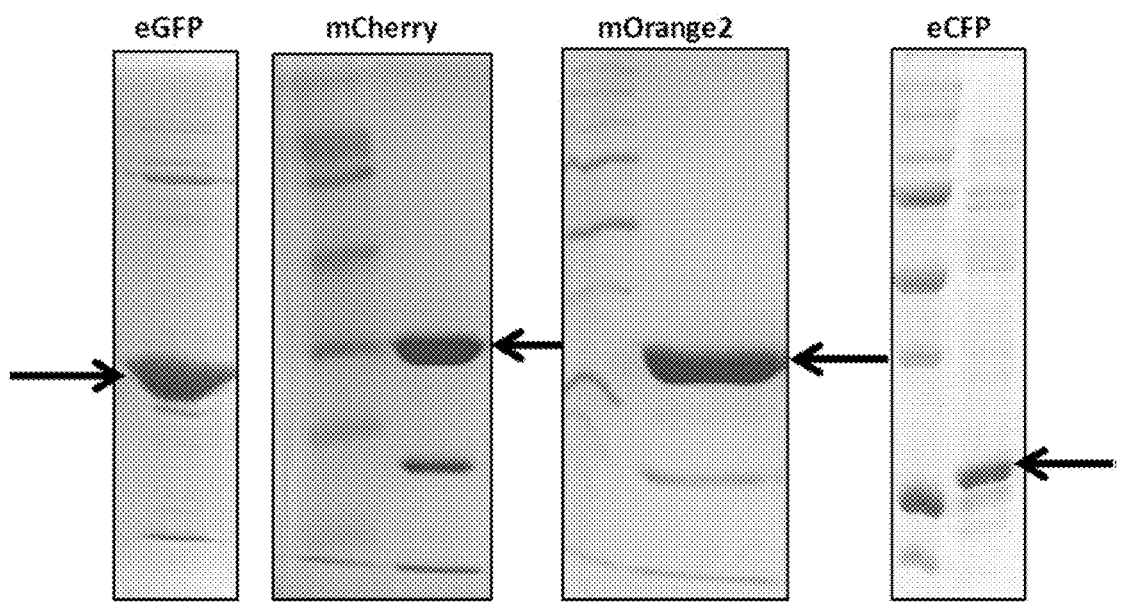
FIG. 6 is a SDS-PAGE example of purified fluorescence proteins. The arrow highlights the protein of interest.

The reporter modules were successfully produced and purified by affinity chromatography (FIG. 6). The yield of the production was around 25 mg of protein/L of culture. FIG. 6 is a SDS-PAGE of purified fluorescent proteins; the arrow highlights the protein of interest. Table 2 shows the properties of the purified reporter modules (here, fluorescent proteins).

TABLE 2

| Protein | Amino Acids (#) | Mol. Wt. (Da) | pI |
|---|---|---|---|
| eGFP | 247 | 27878.1 | 5.99 |
| mCherry | 244 | 27658.8 | 6.06 |
| mOrange2 | 244 | 27756.1 | 6.72 |
| eCFP | 247 | 27842.0 | 5.99 |

Example 2

Figure 7:
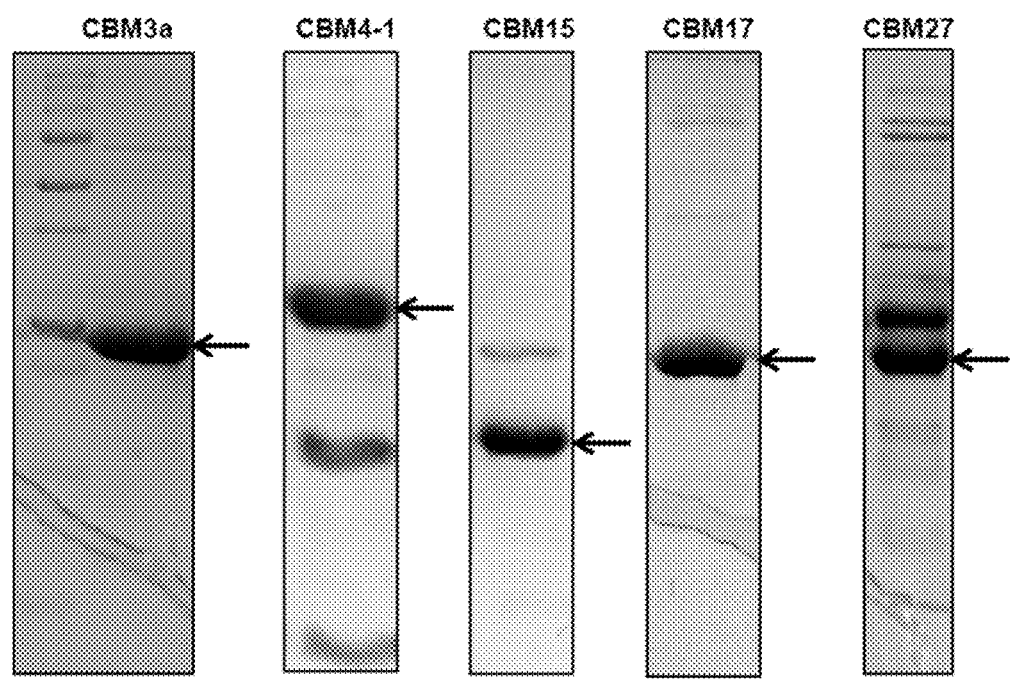
FIG. 7 is an SDS-PAGE example of purified CBMs. The arrow highlights the protein of interest.

This example demonstrates production of binding modules (CBMs) in accordance with the present invention. Five CBM genes (CBM 3a, 4-1, 15, 17, and 27) were cloned in pET11 vector and expressed in prokaryotic systems. The CBMs were produced and purified by affinity chromatography (FIG. 7). The yield of the production of the CBM was around 10 mg of protein/L of culture. FIG. 7 is a SDS-PAGE of purified CBMs; the arrow highlights the protein of interest. Table 3 displays the properties of the purified binding modules (here, CBMs).

TABLE 3

| Protein | Amino Acids (#) | Mol. Wt. (Da) | pI |
|---|---|---|---|
| CBM3a | 206 | 22375.1 | 7.58 |
| CBM4-1 | 161 | 16528.7 | 3.88 |
| CBM17 | 221 | 23926.9 | 5.46 |
| CBM15 | 171 | 17949.4 | 4.31 |
| CBM27 | 185 | 21242.6 | 5.57 |

Example 3

Figure 8:
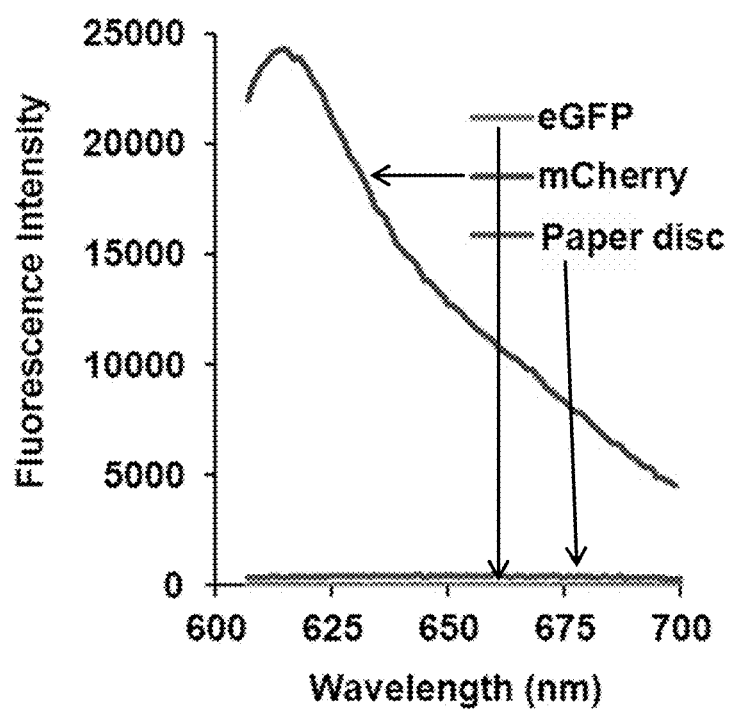
FIG. 8 is an example of a graph depicting emission spectra of reporter modules (eGFP and mCherry) and of a pulp handsheet disk after excitation at 549 nm.
Figure 9:
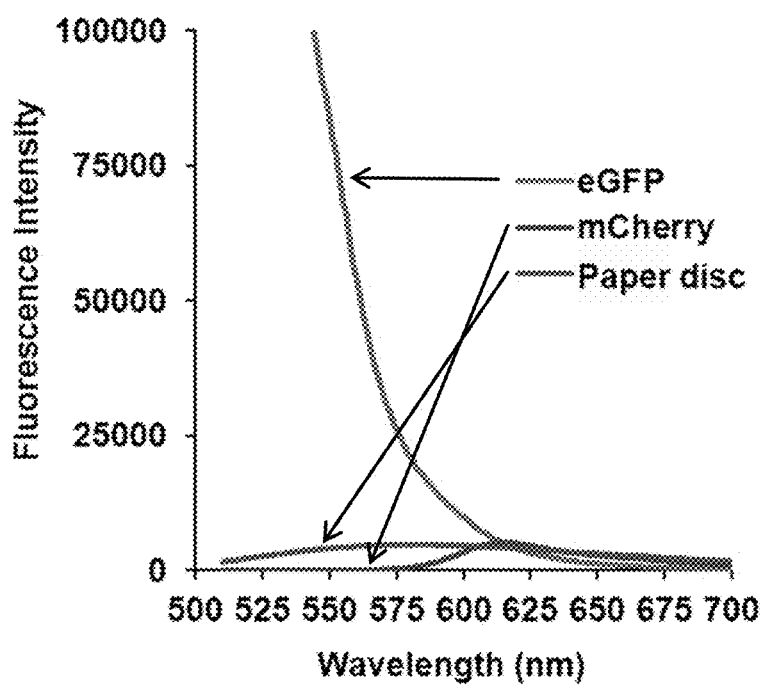
FIG. 9 is an example of emission spectra of FPs (eGFP and mCherry) and a pulp handsheet disk using an excitation wavelength of 488 nm.

This example demonstrates the fluorescence emission by reporter modules in accordance with the present invention. Emission spectra of pulp and reporter modules (eGFP, mCherry and mOrange2) were measured. The spectra were acquired at 23° C. and the proteins were diluted in a 20 mM Tris-HCl pH 7.5 buffer containing 20 mM NaCl and 5 mM $CaCl_2$. The spectra in FIGS. 8 and 9 show that depending on the excitation wavelength (488 nm vs 549 nm), the change in fluorescence intensity (FI) (eGFP vs mCherry) can be measured independent of pulp auto-fluorescence or other probes. FIG. 8 shows the emission spectra of reporter modules (eGFP and mCherry) and of a pulp handsheet disk after excitation at 549 nm. With this excitation wavelength, mCherry fluorescence dominates over the other substrates signal. FIG. 9 shows emission spectra of FPs (eGFP and mCherry) and a pulp handsheet disk using an excitation wavelength of 488 nm. At this excitation wavelength, the pulp and mCherry fluorescence is much weaker than eGFP.

Example 4

Figure 10:
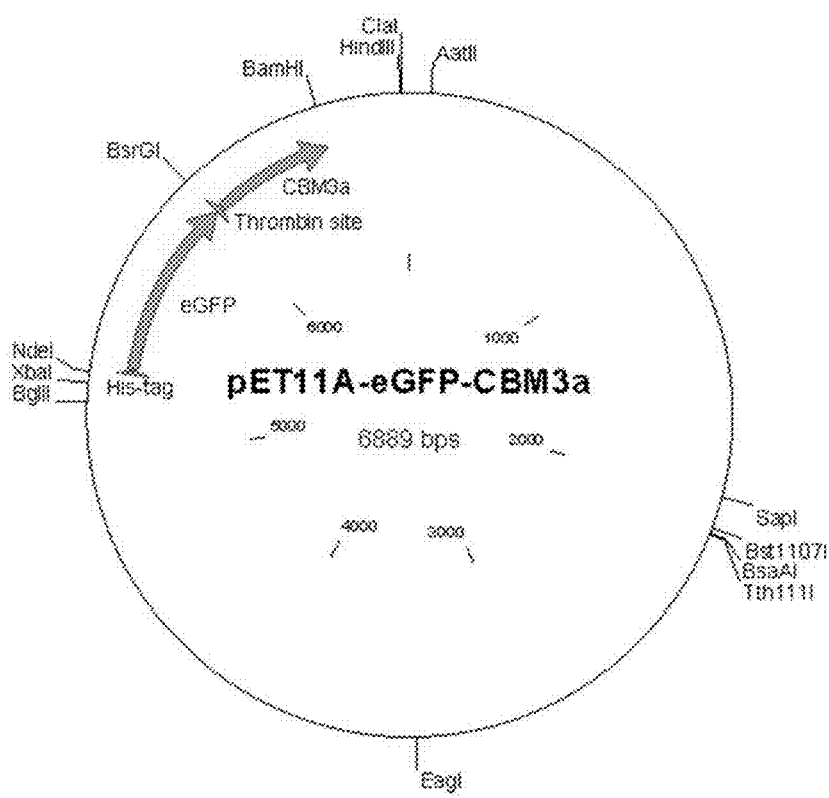
FIG. 10 is an example of a schematic diagram of a pET11A-eGFP-CBM3a expression vector (Probe 1).
Figure 11:
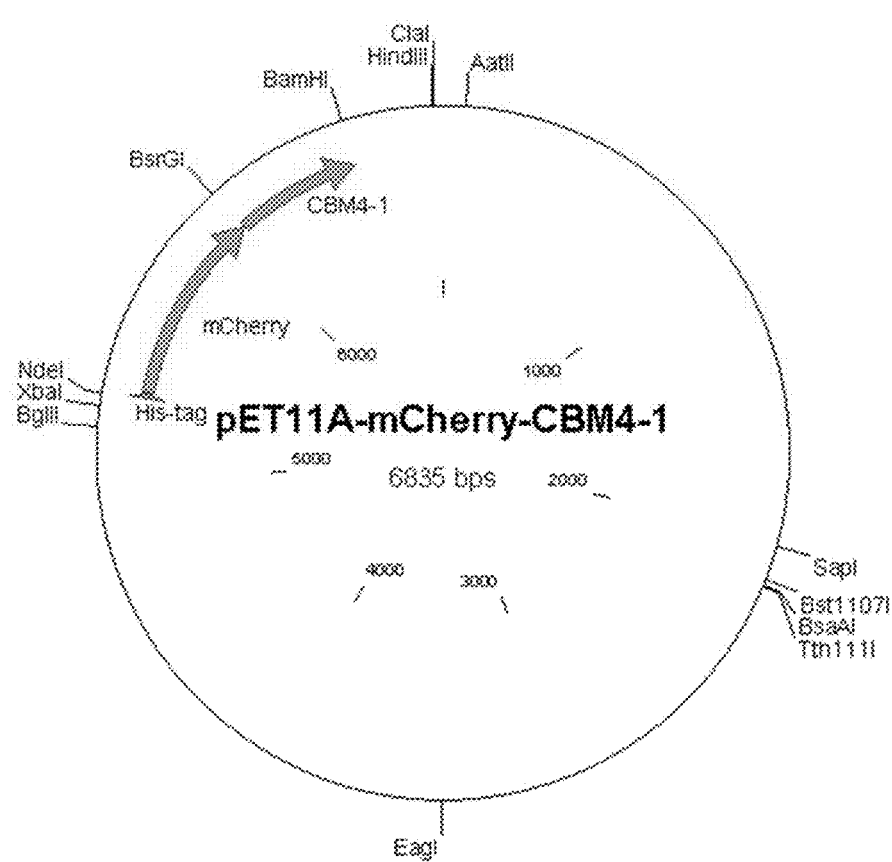
FIG. 11 is an example of a schematic diagram of a pET11A-mCherry-CBM4-1 expression vector (Probe 2a).
Figure 12:
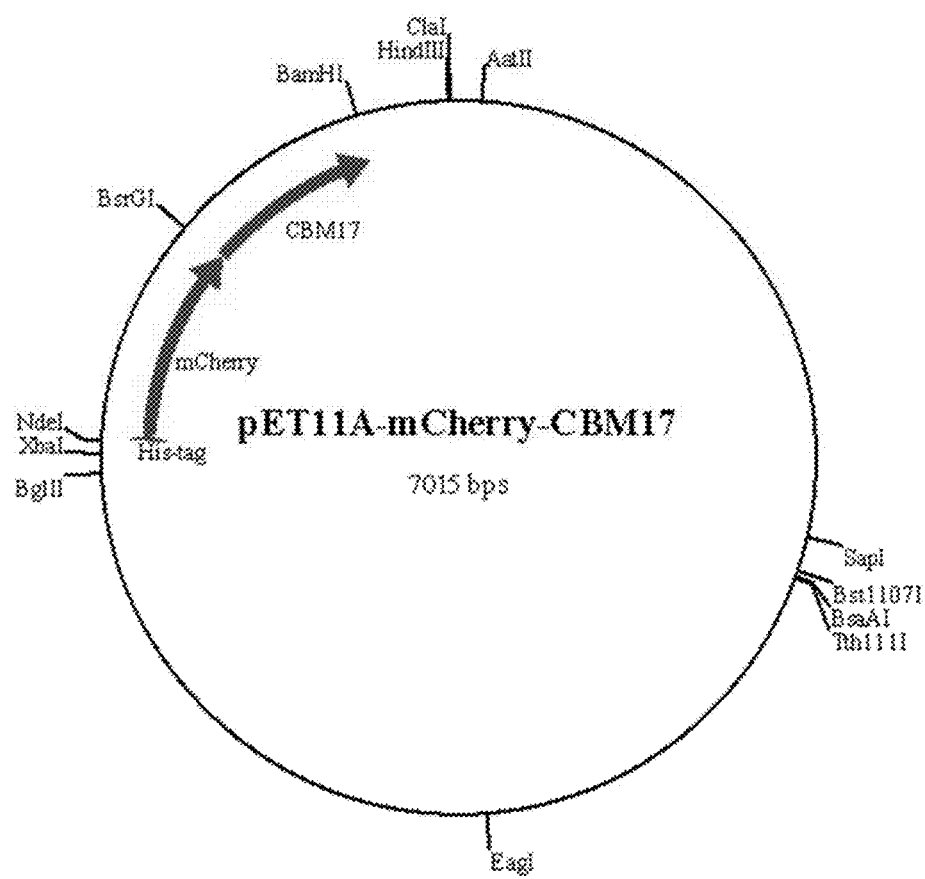
FIG. 12 is an example of a schematic diagram of a pET11A-mCherry-CBM17 expression vector (Probe 2b).
Figure 13:
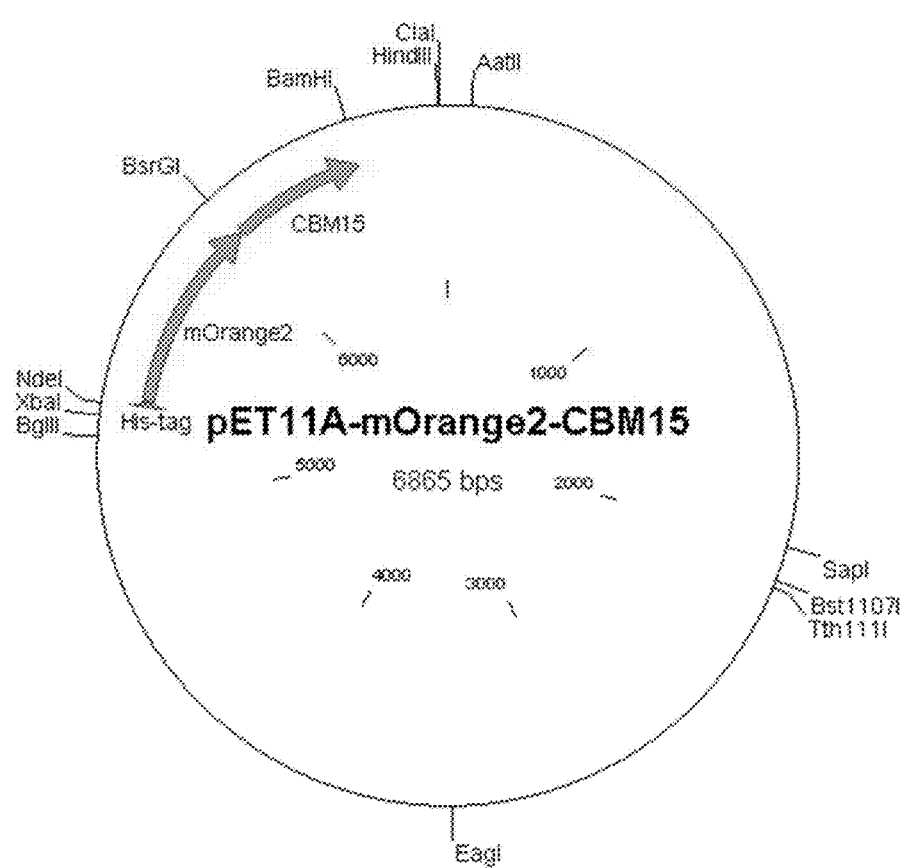
FIG. 13 is an example of a schematic diagram of a pET11A-mOrange2-CBM15 expression vector (Probe 3).
Figure 14:
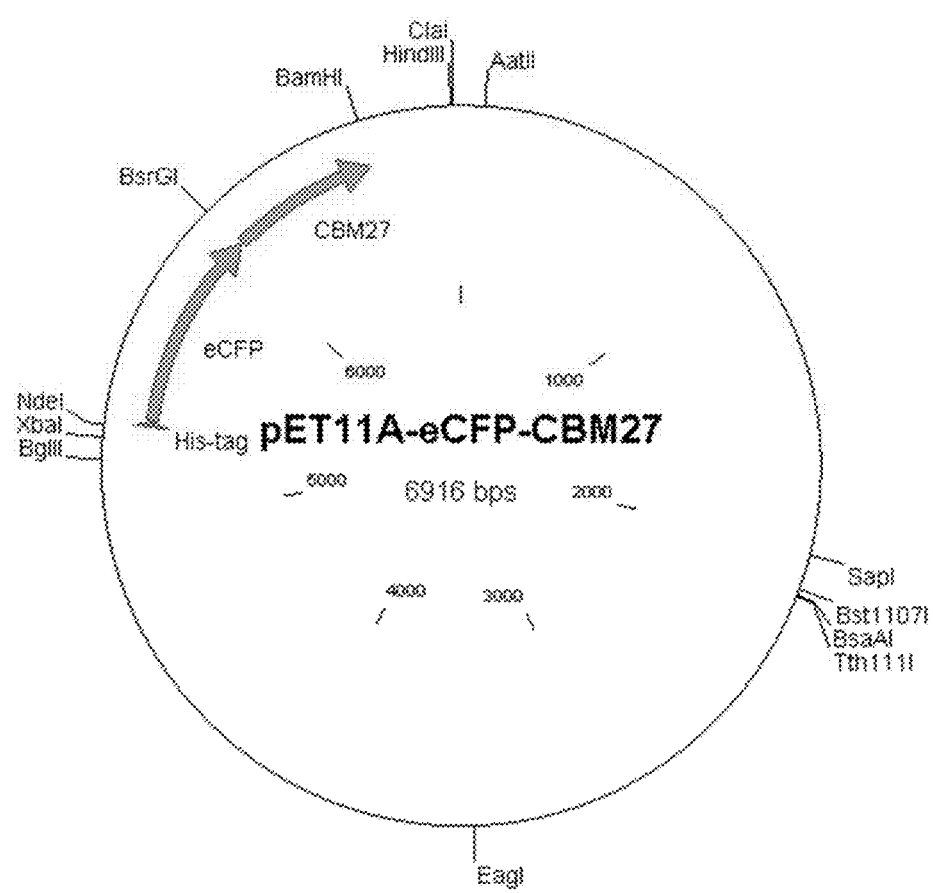
FIG. 14 is an example of a schematic diagram of a pET11A-eCFP-CBM27 expression vector (Probe 4).

This example demonstrates the production of complete probes (binding module-reporter module). The genes that were used for production of reporter modules and binding modules were fused to generate the probes. FIGS. 10-14 show the pET11 vectors and the genetic map covering the fusion sequence. The resulting molecules (probes) include a reporter module at the N-terminus, followed by the binding module. FIG. 10 shows the vector and map for pET11A-eGFP-CBM3a expression vector (Probe 1). FIG. 11 shows the vector and map for pET11A-mCherry-CBM4-1 expression vector (Probe 2a). FIG. 12 shows the vector and map for pET11A-mCherry-CBM17 expression vector (Probe 2b). FIG. 13 shows the vector and map for pET11A-mOrange2-CBM15 expression vector (Probe 3). FIG. 14 shows the vector and map for pET11A-eCFP-CBM27 expression vector (Probe 4). The nucleotide and amino acid sequences for Probe 1 are included in the sequence listing as SEQ ID NOS: 1 and 2 respectively. The nucleotide and amino acid sequences for the linker (joining eGFP and CBM3a) in Probe 1 are included in the sequence listing as SEQ ID NOS: 3 and 4 respectively. The nucleotide and amino acid sequences for Probe 2a are included in the sequence listing as SEQ ID NOS: 5 and 6 respectively. The nucleotide and amino acid sequences for Probe 2b are included in the sequence listing as SEQ ID NOS: 7 and 8 respectively. The nucleotide and amino acid sequences for Probe 3 are included in the sequence listing as SEQ ID NOS: 9 and 10 respectively. The nucleotide and amino acid sequences for Probe 4 are included in the sequence listing as SEQ ID NOS: 11 and 12 respectively. The new molecules (Probes) start with an N-terminal reporter module (fluorescent protein) followed by the appropriate binding module (CBM). The sequence linking the reporter to the binding module is composed of a glycine, except for Probe 1, wherein the linking sequence is SEQ ID NO: 3 encoded by SEQ ID NO: 4 (including a thrombin cleavage site).

The vectors encoding the probes were transformed in *E. coli* BL21-Gold (DE3) pLysS competent cells. Transformed cells were selected on LB-agar with ampicillin (100 μg/mL). *E. coli* cells harboring probe vectors were cultured in Luria-Bertani (LB) broth containing ampicillin (100 μg/mL) at 27° C. to mid exponential phase (A600 nm=0.5). Recombinant protein expression was induced by the addition of 0.5 mM IPTG and further incubated for 16 hours at 27° C. (agitation 200 rpm). Induced cells were centrifuged at 4° C. for 30 min at 4000 g and the pellet were store at −80° C. Cells were suspended in 50 mM sodium phosphate buffer (pH 8.0) and disrupted by sonication. Cells debris was removed by centrifugation at 15,000 rpm for 15 min. The 6×His tagged protein was purified under native conditions using Ni-NTA nickel affinity resin (Qiagen) according to manufacturer specification at pH 8 using imidazole for elution. A second passage was utilized to increase the purity of the protein preparation. In order to remove salts and imidazole, purified probes were dialyzed in a buffer containing 20 mM Tris-HCl pH 7.5, 20 mM NaCl and 5 mM $CaCl_2$ for 24 hours at 4° C. Protein concentration was determined using a Bradford protein assay.

Figure 15:
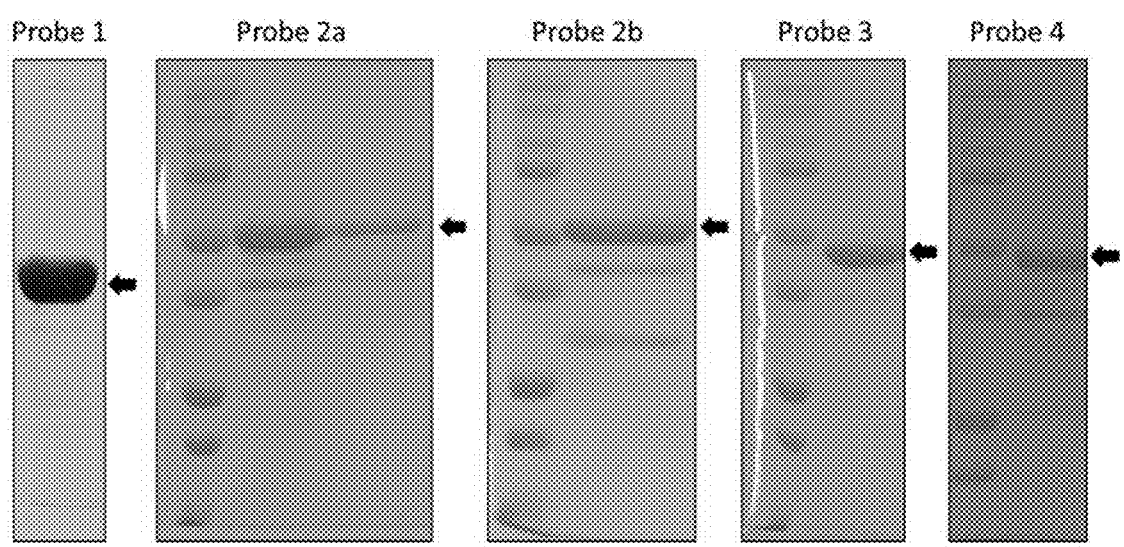
FIG. 15. is a SDS-PAGE example analysis of Probes 1 to 4. From left to right: Probe 1, Probe 2a, Probe 2b (not used here has a higher affinity to amorphous cellulose than Probe 2a), Probe 3 and Probe 4. Shown on the left side of the last four gels is a standard size ladder allowing estimation of sizes for proteins migrated on the same gel.

FIG. 15 shows a SDS PAGE analysis of each probe. The arrows indicate the position of the probe fused proteins. The size of each probe corresponds to the size expected on the basis of its amino acid residue content. Shown on the left side of the last four gels is a standard size ladder allowing estimation of sizes for proteins migrated on the same gel. Table 4 shows the properties of the purified Probes (reporter module-binding module).

TABLE 4

| Protein | Amino Acids (#) | Mol. Wt. (Da) | pI |
| --- | --- | --- | --- |
| eGFP-CBM3a | 415 | 46260.9 | 5.91 |
| mCherry-CBM4-1 | 397 | 43158.4 | 4.67 |
| mCherry-CBM17 | 457 | 50556.6 | 5.49 |
| mOrange2-CBM15 | 407 | 44676.4 | 5.10 |
| eCFP-CBM27 | 424 | 48055.5 | 5.59 |

Example 5

This example demonstrates spectroscopic characterization of probes after production in accordance with the present invention. In order to verify that the fusion of the reporter modules to the binding modules did not prevent native folding, a spectroscopic analysis was carried out. The spectra were acquired at 23° C. and the proteins were diluted in a 20 mM Tris-HCl pH 7.5 buffer containing 20 mM NaCl and 5 mM $CaCl_2$. The absorption and emission spectra recorded for Probe 1, Probe 2b, Probe 3 and Probe 4 are shown in FIGS. 16A-16D. They are comparable with spectra reported in the literature and strongly suggest that the reporter modules are not affected by the presence of the binding modules. In FIGS. 16A-D, excitation spectra are shown as dashed lines and emission spectra as full lines for the FP-CBM proteins. These results strongly indicate that the reporter modules (fluorescent proteins) are properly folded after their recovery from bacteria and that the close proximity of the binding module has no appreciable impact on its reporting capacity.

Example 6

Figure 17:
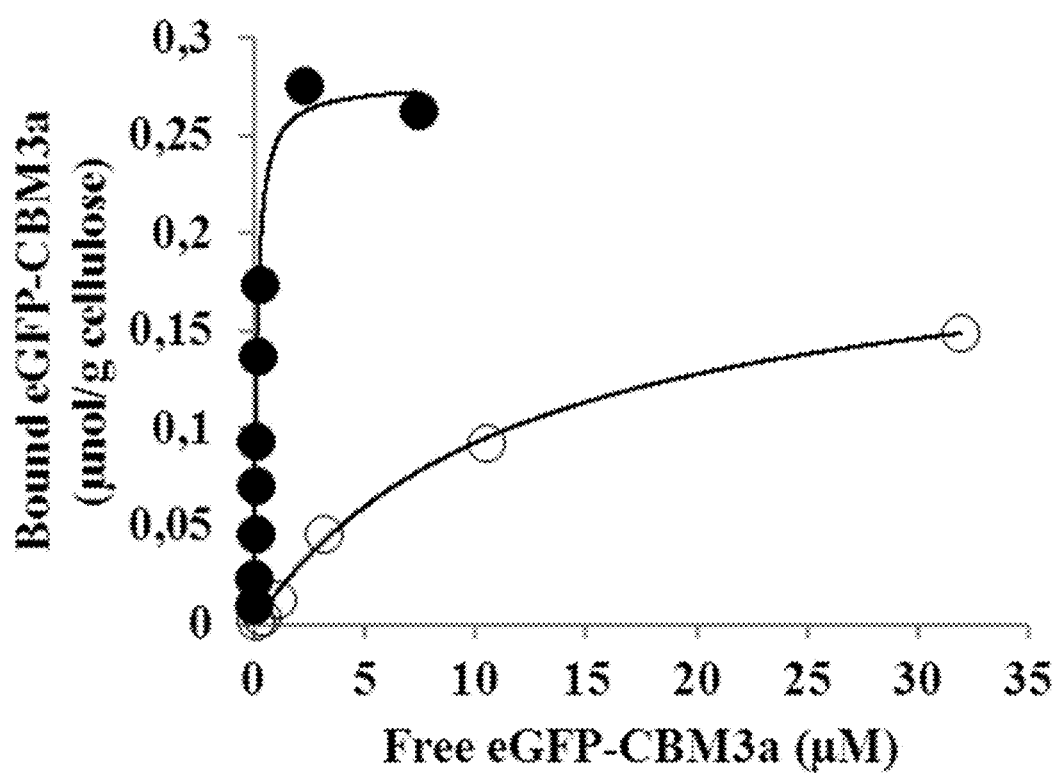
FIG. 17 is an example of a graph of binding saturation from a solid state depletion assay using Probe 1.

This example demonstrates binding of the probes to model compounds in accordance with the present invention. A solid state depletion assay was performed involving Probe 1 and AVICEL or WHATMAN paper as the substrate. AVICEL is a commercial substrate made of crystalline cellulose available from FMC Corporation. WHATMAN paper is an amorphous cellulose filter paper available from GE Healthcare Life Sciences. FIG. 17 shows the results of a solid state depletion assay in which binding saturation of Probe 1 to AVICEL is apparent.

Affinity ($K_a$) of Probe 1 for AVICEL was measured using a modified version of a solid state depletion assay in order to ascertain that the fusion of the reporter module (eGFP) with the binding module (CBM3a) did not negatively affect the folding and thus the affinity of CBM3a for AVICEL. FIG. 17 shows that Probe 1 has an affinity constant ($K_a$) of 8 μM for AVICEL, a value similar to that reported for the commercial construct for crystalline cellulose (7.7 μM). This result confirms that the binding module (CBM3a) of Probe 1 is well folded and that it binds to crystalline cellulose with a high affinity regardless of the close proximity of the reporter module (eGFP).

Binding isotherms of eGFP-CBM3a to AVICEL (filled circle) and WHATMAN paper (open circle) after a 1 hour incubation at 23° C. of the various cellulose support with eGFP-CBM3a (100 μg/well) in a 20 mM Tris-HCl pH 7.5 buffer containing 20 mM NaCl and 5 mM $CaCl_2$. The affinity constant ($K_a$) was calculated from nonlinear regression of $[P_{bound}]=N_oK_a[P_{free}]/(1+K_a[P_{free}])$. In this example, $K_a$ is equal to 8 μM for AVICEL and 0.083 for WHATMAN paper.

Example 7

Example 7 sets forth parameters for a typical probe binding experiment used in the following examples. Materials and solutions included filtered buffer (20 mM Tris-CL pH 7.5+20 mM NaCl+5 mM $CaCl_2$; agitation at room temperature for 1 hour), 6% milk (fresh) in buffer (dissolve 1.2 g of milk into 20 ml of buffer; Centrifuge 2 min, 100 g, RT), 3% milk (fresh) in buffer, TWEEN 0.05% in buffer, pulp-derived handsheet (paper disk: 3 mm diameter) glued onto the bottom of black microplate shining face down. Fluorescence acquisition included endpoint and area scanning 3×3 500 μm; excitation wavelength (reporter module-dependent) (9 mm)/emission wavelength (reporter module-dependent) (9 mm); gain 50; 75 and 100; and top (4.5 mm) detection. The reaction volume was 200 μl. The fluorescent (fusion) probe (or fiber polymer) treatment method FPTM protocol was consistent with that described in Knox P. J. (2012) Methods in Enzymology, volume 510, 233-245, which is incorporated by reference herein in its entirety. A similar procedure is described in Ding et al. (2006) BioTechniques 41, 435-443, which is incorporated by reference herein in its entirety.

The fluorescence of the untreated paper disks was measured. The handsheet was incubated in 200 μl of milk 3%, one hour at room temperature with a slow agitation. Wash 3

(200 µl)×5 min was performed with buffer at room temperature with agitation. The fluorescence of the blocked paper disks was measured. 200 µl of probe/milk 3% was added and incubated at room temperature for one hour with a slow agitation. The supernatant was removed and total fluorescence was measured. Wash 3 (200 µl)×5 min with buffer was performed at room temperature with agitation. The residual fluorescence was measured. Wash 3 (200 µl)×5 min was performed with TWEEN 0.05% at room temperature with agitation. Residual fluorescence was measured. Black 96 wells microplate (Costar, cat #3631) were employed. A SYNERGY Mx program was run (BioTek Instruments, Inc., Winooski, Vt.).

Figure 18:
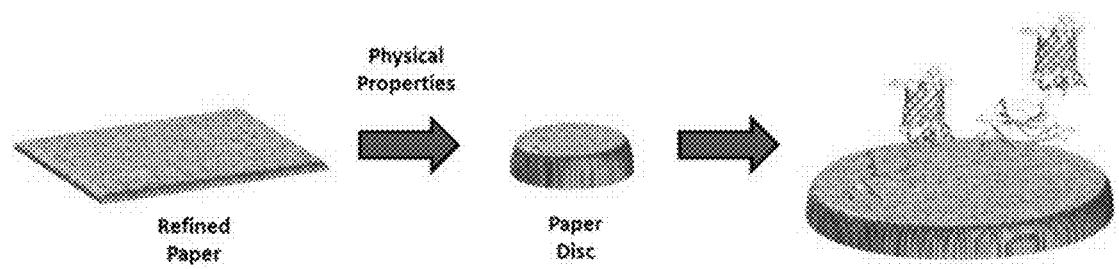
FIG. 18 is an example of a schematic diagram describing a probe-binding experiment on a paper disk.

FIG. 18 is a schematic diagram describing the probe binding experiments on a paper disk. The various pulps used in the following examples are described in Table 5 (NA: Not available; "*"=Pulp chemical composition (wt %) measured at CRML). Pulps used were from North American paper plants.

TABLE 5

Chemical Composition and Available Characteristics of Different Pulps.

| | Pulp 1 | Pulp 2 | Pulp 3 | Pulp 4 | Pulp 5 | Pulp 6 |
|---|---|---|---|---|---|---|
| Pulp origin | Plant 1 | Plant 2 | Plant 3 | Plant 3 | Plant 3 | Plant 3 |
| Pulp | High yield Kraft | Kraft | Kraft | Kraft | Mechanical | Mechanical |
| | Unrefined Unbleached Furnish: softwood (resinous) | Unrefined Unbleached Furnish: softwood (resinous) | Unrefined Unbleached Furnish: softwood (resinous) | Unrefined bleached Furnish: softwood (resinous) | Unrefined Unbleached Furnish: softwood (resinous) | Unrefined bleached Furnish: softwood (resinous) |
| Pulp Consistency (wt %) | 5.16 | 4.39 | 2.81 | 4.37 | 3.77 | 4.17 |
| Pulp Initial pH | 9 | 7.15 | 9.28 | 7.11 | 4.48 | 4.72 |
| Kappa number | 27-29 | 20-25 | NA | NA | NA | NA |
| Cellulose* | 83.91 | 89.49 | 86.7 | 89.7 | 46 | 46.6 |
| Hemicellulose* | 9.54 | 7.29 | 16 | 16.9 | 21.7 | 22.2 |
| Lignin* | 6.7 | 3.2 | 4.4 | 1.9 | 29 | 29 |

Example 8

This example demonstrates the comparison of fluorescence from a commercial "binding-reporter" probe with the fluorescence from a reporter module alone at the surface of paper in accordance with the present invention. The specific detection of crystalline cellulose on the surface of small disks of pulp 1 (~0.5 mg) was achieved by binding commercial eGFP-CBM3a (NZYTech company). The non-specific signal provided by the binding of the reporter module on the small disks was measured after incubation with the reporter module alone. The assay was performed into 96 wells microplate. Excess of Probe 1 (or reporter module GFP) was removed by washing using Tween 20 (0.05%).

Figure 19:
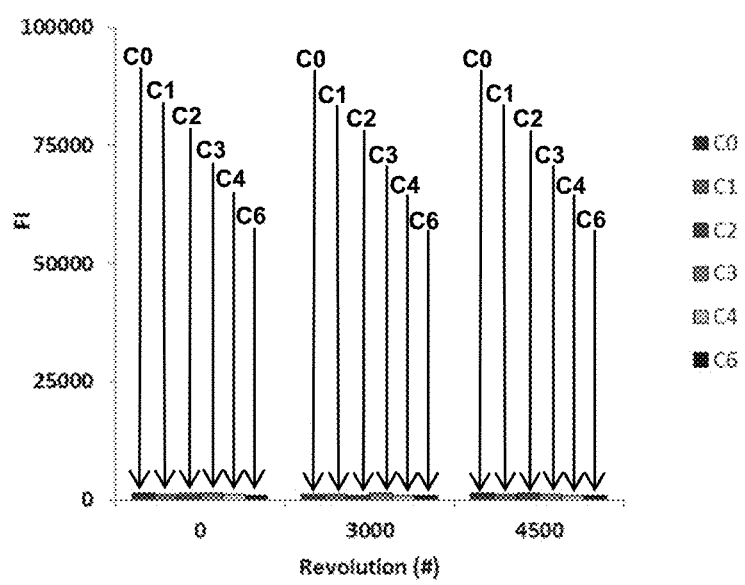
FIG. 19 is an example of a graph of fluorescence intensity (FI) of reporter module (eGFP) alone bound to untreated and cellulase-treated pulp (after two levels of refining).

The fluorescence from the reporter module (alone or as component of the Probe) was measured at a wavelength of 511 nm (excitation wavelength 488 nm) using a SYNERGY Mx microplate reader (BioTek Instruments, Inc.). The fluorescence intensities are presented here as a function of refining intensity and cellulase treatments. FIG. 19 shows fluorescence intensity of reporter module (eGFP) alone bound to untreated and cellulase-treated pulp (after two levels of refining). The non-specific fluorescent signal obtained with the reporter module alone was very low compared to Probe 1.

Figure 20:
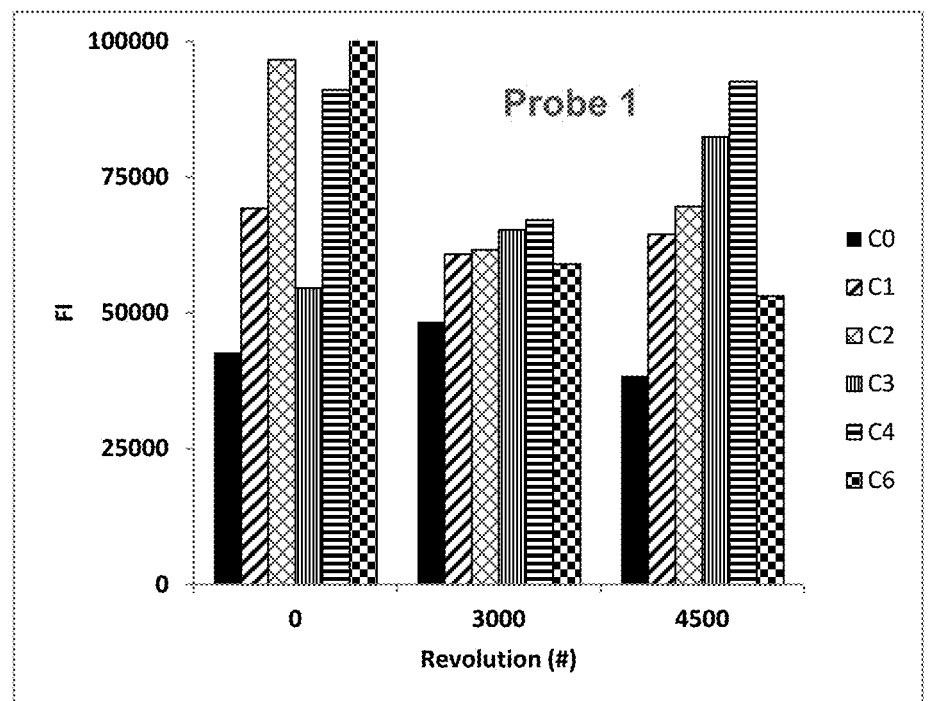
FIG. 20 is an example of a graph of fluorescence intensity of Probe 1 bound to untreated and cellulase-treated pulp (after two level of refining).

FIG. 20 depicts fluorescence intensity of Probe 1 bound to untreated and cellulases treated pulp (after two level of refining). FIG. 20 shows the detection of crystalline cellulose at the surface of cellulase-treated handsheet using Probe 1. Cellulase enzyme treatments of the old pulp increased the fluorescent signal compared to untreated pulp at all levels of refining, which indicates that the cellulase treatments of the pulp uncovered additional crystalline cellulose regions. Accordingly, using Probe 1 of the present invention, the impact of cellulase treatments on pulp can be detected without using any pulp and paper classical tests.

Example 9

This example demonstrates the detection of changes in surface crystalline cellulose after refining and cellulase treatments in accordance with the present invention. The method is based on the fluorescence intensity associated to the recognition of crystalline cellulose by the CBM3a-eGFP (Probe 1) on the surface of handsheets. Using a standardized Probe 1 fluorescence curve, the measured fluorescence intensity can be converted into a quantity (µg) that is then divided by the surface ($mm^2$) of the handsheets. The results ($µg/mm^2$) enable the quantification of the crystalline cellulose on the surface of the handsheets.

Quantification of crystalline cellulose on the surface of pulp 1 handsheets was performed on small disks of ~0.5 mg. The handsheets at basis weight 60 $g/m^2$ were produced from previously treated (cellulases at 0.05%, 1 h, 50° C., pH 7) and untreated pulp 1. The specific detection of crystalline cellulose on the surface of pulp 1 handsheets was achieved with Probe 1 (250 µg/ml, 1 h, room temperature, pH 7.4) in a 24 wells microplate (Gourlay et al., 2012). After three washing steps, the green residual fluorescence was measured at 511 nm (excitation wavelength: 488 nm) using a Synergy Mx microplate reader (Bioteck). The fluorescence intensities were averaged and presented as percentages, as a function of PFI revolutions (FIG. 21) or cellulase treatments (FIG. 22).

Figure 21:
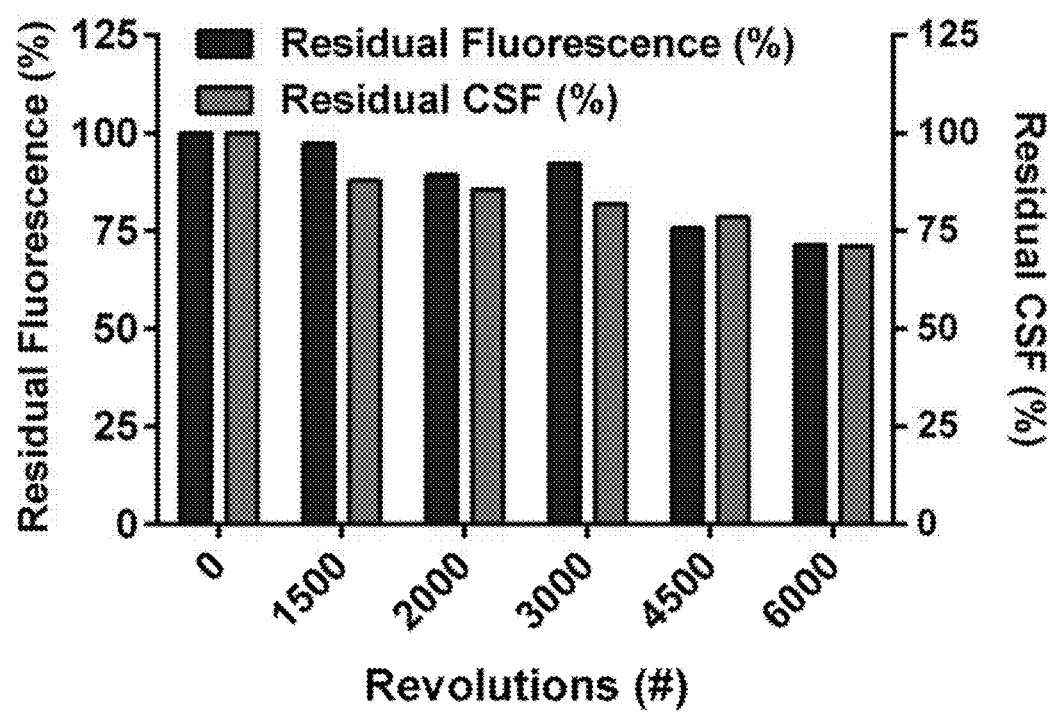
FIG. 21 is an example of a graph showing the impact of PFI refining on the quantification of crystalline cellulose on the surface of pulp 1 handsheets.

FIG. 21 depicts the impact of PFI refining on the quantification of crystalline cellulose on the surface of pulp 1 handsheets. The unrefined fluorescence intensity and corresponding CSF value were set as reference points (100%). FIG. 21 shows that the residual fluorescence, which should indicate the amount of Probe 1-tagged crystalline cellulose at the surface of pulp 1 handsheets, increased from 2.7% to 28.6% as the PFI revolutions increased from 1500 to 6000. This decrease is not linear and was correlated with the decrease in CSF (from 87.9 ml to 71.1 ml), which is an indicator of the degree of hydration of pulp. Accordingly, the amorphogenesis process (water swelling of the pulp), which is associated to PFI refining, is evidently responsible for the recorded decrystallization or loss of crystalline cellulose at the surface of pulp 1 handsheets.

Figure 22:
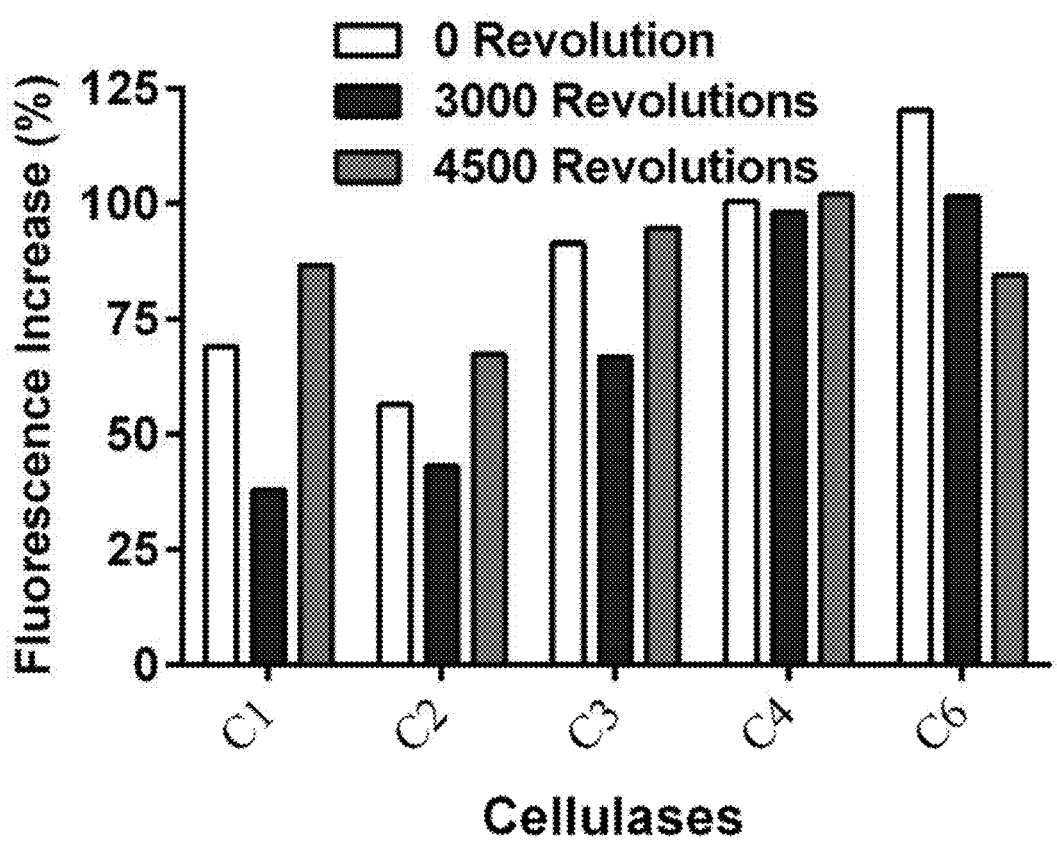
FIG. 22 is an example of a graph showing the impact of cellulase-treatment on the quantification of crystalline cellulose on the surface of pulp 1 handsheets.

FIG. 22 depicts the impact of cellulase treatment on the quantification of crystalline cellulose on the surface of pulp 1 handsheets. The untreated fluorescence intensities at 0, 3000, and 4500 revolutions were set as the reference values (100%). FIG. 22 shows that all cellulase treatments increased the detection of eGFP-tagged crystalline celluloses. These results indicate that enzymes expose previously buried crystalline celluloses at the surface of pulp 1 handsheets compared to untreated handsheets.

The highest increase recorded was for the treatment of pulp 1 with cellulase C6 without refining. Cellulase C1 and C2 treatments led to the lowest increase of crystalline cellulose on unrefined and refined pulp 1 at 3000 revolutions (vs untreated) compared to the other enzyme samples. However, the use of more intense refining (4500 revs) on treated pulp 1 with cellulase sample C1, C2, and C3 lead to an increase of crystalline celluloses. These observations might be explained by the generations of microfibrils after refining and consequently an increase exposition of crystalline cellulose at the surface of the fibers. These results suggest that cellulase treatments of pulp 1 followed by mechanical treatment expose a larger quantity of crystalline celluloses. In opposition to all other enzymes, refining had no impact on C4-treated handsheet.

Example 10

Figure 23:
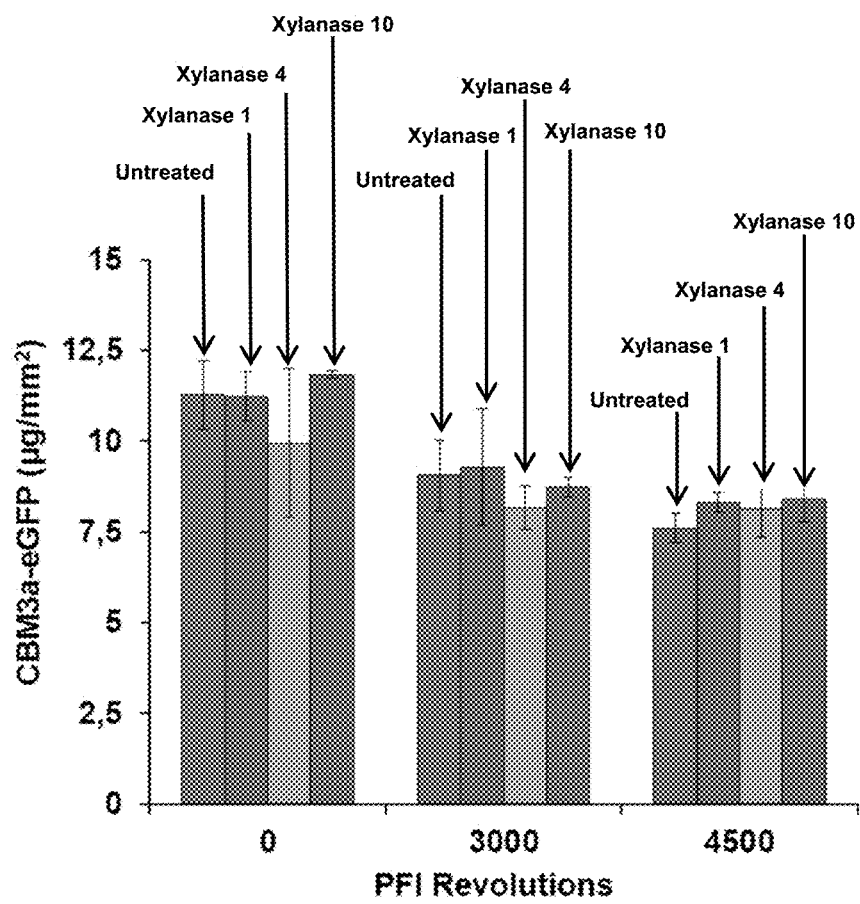
FIG. 23 is an example of graph depicting quantification ($\mu g/mm^2$) of Probe 1 bound on the surface of xylanase-treated handsheets.

This example demonstrates the prediction of the presence or absence of changes in surface crystalline cellulose after refining and xylanase treatments in accordance with the present invention. Digestion of the xylan polymers by xylanases can uncover crystalline cellulose and increase its detection on handsheet surfaces when compared with the untreated controls. Probe 1 was used to detect changes in crystalline cellulose at the surface of paper after xylanase treatments. FIG. 23 depicts the quantification ($\mu g/mm^2$) of Probe 1 bound on the surface of xylanase-treated handsheets from plant 2 refined at 0, 3000 and 4500 PFI revolutions. Pulp 2 was used for sheet preparation. The excitation wavelength was 488 nm. No xylanase treatments used here had a significant impact on fluorescence detected. The quantity of crystalline cellulose measured here suggests that xylanase preparations used had no impact on cellulose fiber surface. This result is in complete agreement with the analysis of paper physical properties and fiber morphologies after xylanase treatments. The probe 1 FPTM results reveal the absence of xylanase impact in a much less time than involved for traditional TAPPI methods, thus enabling a fast, high throughput protocol.

Example 11

This example demonstrates the detection of crystalline cellulose after refining in accordance with the present invention. Correlations were determined between Probe 1 detection and paper physical properties using two different pulps. Two pulps (Pulp 1 and Pulp 2) were refined and analyzed by Probe 1 and by standard TAPPI methods. The measurement of crystalline cellulose on handsheet disks (60 $g/m^2$) was performed by incubating the paper disks with 250 $\mu g/ml$ of Probe 1. Probe 1 fluorescence was used for recognition of crystalline cellulose on the surface of handsheets after refining (various levels of energy). Using a standardized curve, the measured fluorescence intensity is converted into a quantity ($\mu g$) of crystalline cellulose, which is then divided by the surface ($mm^2$) of the handsheets. The results ($\mu g/mm^2$) enable the quantification of the crystalline cellulose on the surface of the handsheets.

Figure 24:
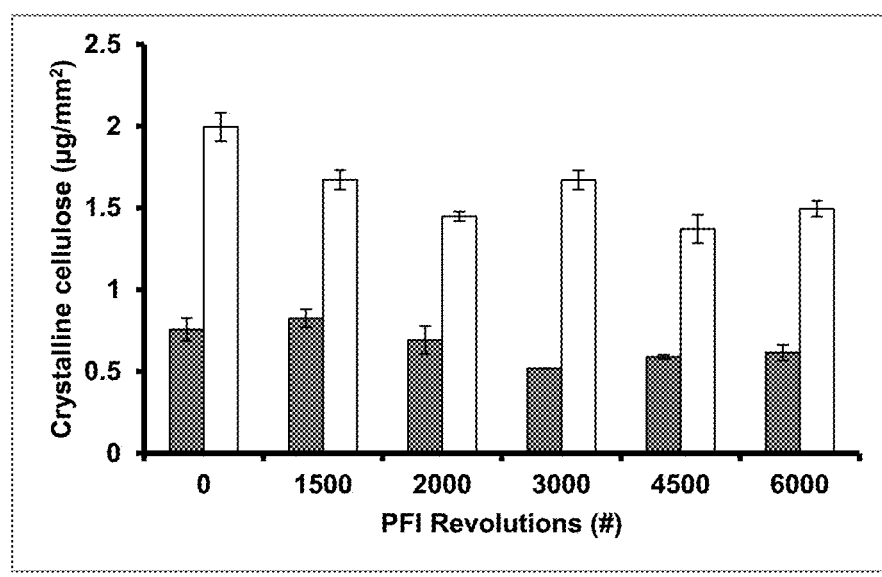
FIG. 24 is an example of a graph depicting quantification of crystalline cellulose ($\mu g/mm^2$) on the surface of PFI refined handsheet produced at two different plants.

FIG. 24 depicts the quantification of crystalline cellulose ($\mu g/mm^2$) on the surface of PFI refined handsheet (Pulp 1 (plant 1; left bar) vs Pulp 2 (plant 2; right bar). These FPTM results support the concept that pulp refining partially decrystallizes cellulose. In the case of the Pulp 2 handsheets, at least three decrystallization events (or steps) are observed: 0-2000, 3000-4500 and at 6000 PFI revolutions. This effect is less apparent than when using more than 3000 revs.

Figure 25A:
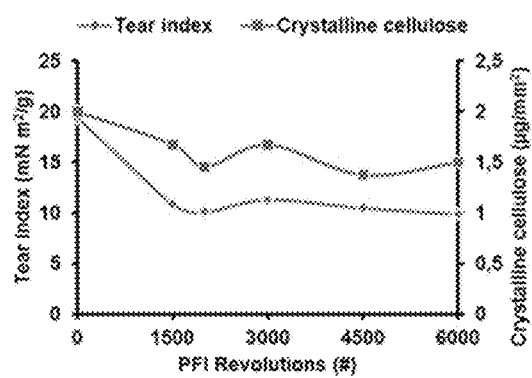
FIGS. 25A-25D are examples of graphs depicting correlations between crystalline cellulose quantification using Probe 1 ($\mu g/mm^2$) and pulp 2/paper physical properties as a function of refining energy (PFI revolutions) including, respectively, tear index (mN $m^2$/g), tensile index (N m/g), internal bond strength (J/$m^2$), an fibers mean length (mm).
Figure 25B:
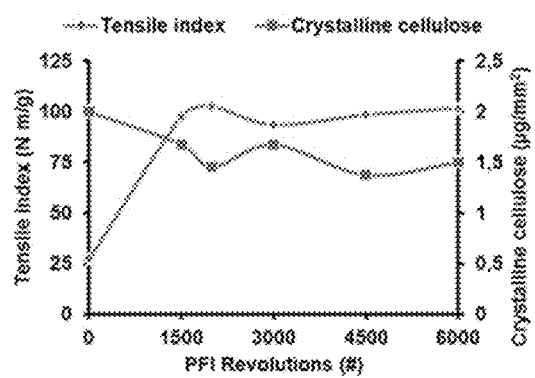
Figure 25C:
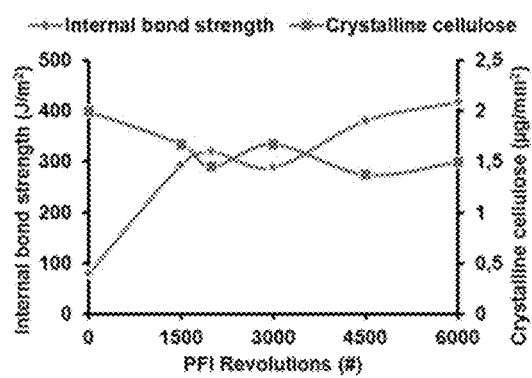
Figure 25D:
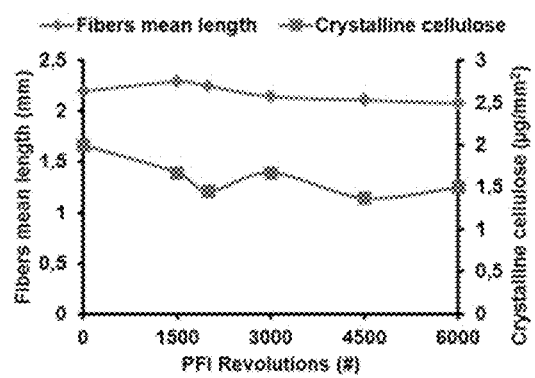

FIGS. 25A-25D depict correlations between crystalline cellulose quantification using Probe 1 ($\mu g/mm^2$) and Pulp 2/paper physical properties as a function of refining energy (PFI revolutions). FIG. 25A depicts tear index (mN $m^2/g$), FIG. 25B depicts tensile index (N m/g), FIG. 25C depicts internal bond strength ($J/m^2$), and FIG. 25D depicts fibers mean length (mm). FIGS. 25A-25D show the correlations between Probe 1 signal and the corresponding paper's physical properties for the Pulp 2 handsheets. An inverse correlation is observed with the tensile index and the internal bond strength (FIG. 25B-25C). In contrast, the tear index is directly correlated with the crystalline cellulose quantification (FIG. 25A). These correlations can be used for predicting the impact of various refining treatments on final paper properties in a very short time (1 hour vs days) compared to TAPPI pulp and paper analyses. The internal bond and fiber length were further modified by refining past 3000 revs, at variance with tear and tensile indices that stabilized under similar conditions.

Figure 26A:
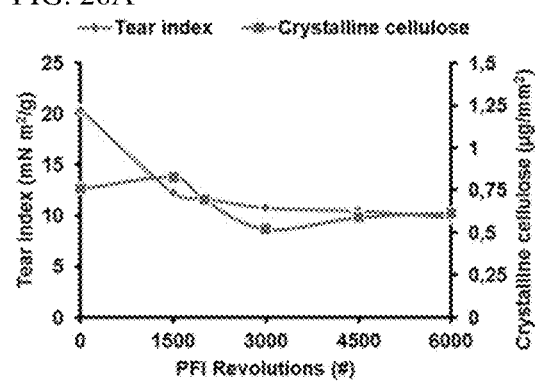
FIGS. 26A-26D are examples of graphs depicting correlations between crystalline cellulose quantification using Probe 1 ($\mu g/mm^2$) and pulp 1/paper physical properties as a function of refining energy (PFI revolutions) including, respectively, tear index (mN $m^2$/g), tensile index (N m/g), internal bond strength (J/$m^2$), an fibers mean length (mm).
Figure 26B:
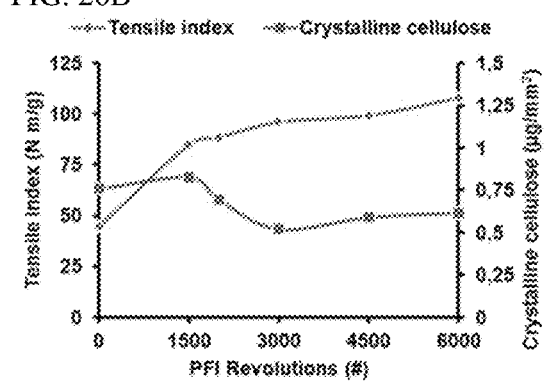
Figure 26C:
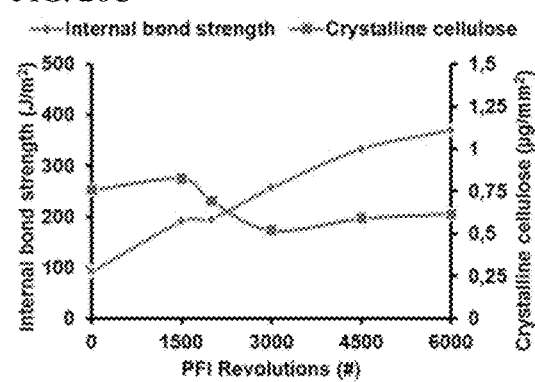
Figure 26D:
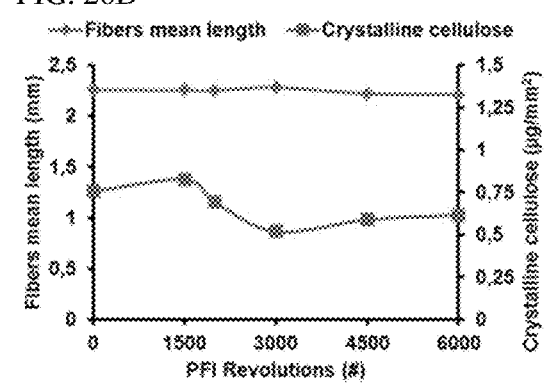

The changes in properties and crystalline cellulose detected after treatment of pulp 1 are shown in FIGS. 26A-26D. Correlations between crystalline cellulose quantification using Probe 1 ($\mu g/mm^2$) and pulp 1/paper physical properties as a function of refining energy (PFI revolutions) are depicted. FIG. 26A depicts tear index (mN $m^2/g$), FIG. 26B depicts tensile index (N m/g), FIG. 26C depicts internal bond strength ($J/m^2$), and FIG. 26D depicts fibers mean length (mm). The amount of cellulose detected by Probe 1 decreased as refining energy increased in general, with the exception of the value associated with 1500 revs. Except for this particular value, all panels suggest the same correlations as those observed with pulp 2 (FIGS. 25A-25B). The different content in lignin of either pulp did not appear to affect the overall correlations. Correlations were positive for tear index, and reciprocal for internal bond and tensile index.

The four properties monitored continued to change when refining was increased past 3000 revs. Thus, applying the method to different pulp may result in subtle changes in correlations at high refining energy. Independent of the physical properties and the pulp studied here, the impact of refining on crystalline cellulose was observed after a minimal degradation of fiber (i.e. when treatment exceeded 1500 revs). The impact of refining past 3000 revs is no longer associated with changes in crystalline cellulose at the surface (it is not changed by further refining). Consequently, to improve and develop pulp/paper physical properties, the refining intensity should minimally degrade the crystalline matrix of the pulp.

The results demonstrate that the method is a diagnostic indicator that can be taken into account when determining the refining conditions for a given set of properties. Its simplicity and high sensibility enable a fast and efficient diagnostic of the best refining conditions used for a set of physical properties. The results show that the method can be used to predict the impact of a treatment on pulp and paper properties for tear, tensile and internal bond strength, without performing actual measurements of those properties on handsheets.

Example 12

This example demonstrates the detection of xylan on the surface of paper disks in accordance with the present invention. Pulp 5 (unbleached mechanical pulp), Pulp 6 (bleached mechanical pulp, Pulp 3 (unbleached Kraft pulp), Pulp 4 (bleached Kraft pulp), and Pulp 2 (unbleached Kraft pulp) were used in this example (as described above in Table 5). The assay was performed in 96 well-microplates with each well containing a small handsheet disk (60 g/m$^2$). The specific detection of xylan on the surface of such disks made from different pulps was achieved by binding Probe 3 (CBM15-mOrange2). The fluorescence intensity was measured after incubating the paper disks with 200 µl solution of Probe 3. The excess Probe 3, as well as non-specific binding of the same adduct to any other moieties, was removed by washing three times with a TWEEN 20 solution (0.05%). Fluorescence intensity from bound Probe 3 was measured at a wavelength of 569 nm (excitation wavelength 549 nm) using a SYNERGY Mx microplate reader.

Figure 27:
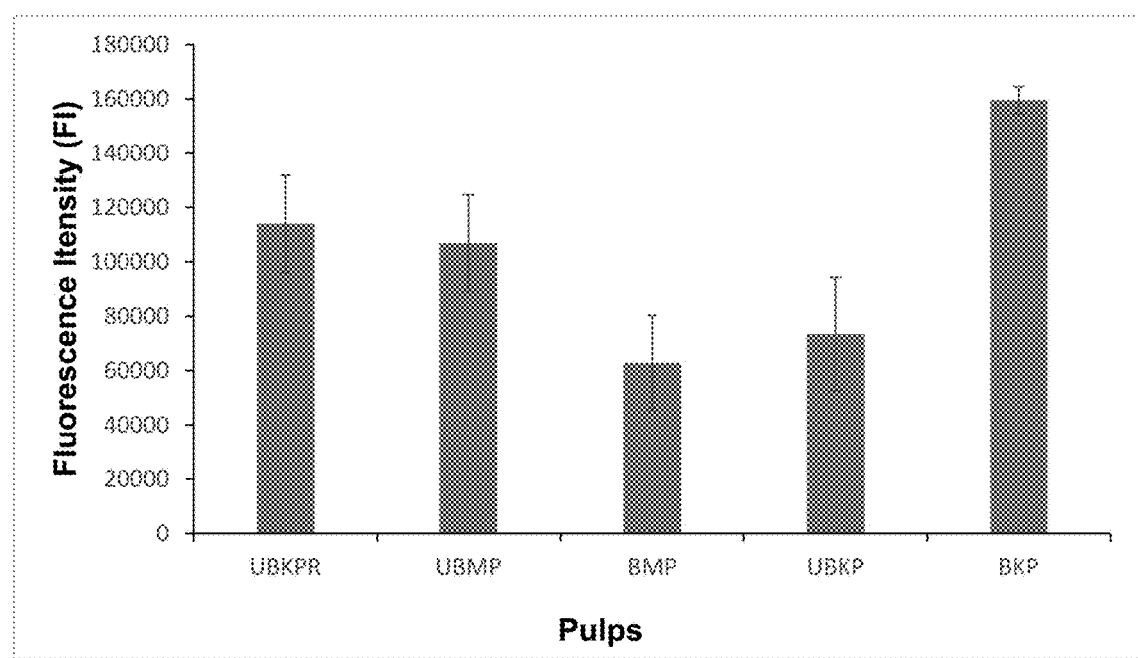
FIG. 27 is an example of a graph depicting fluorescence intensity of Probe 3 bound to xylan at the surface of five different paper disks including, respectively, UBKPR: Unbleached Kraft pulp (pulp 2), UBMP: unbleached mechanical pulp (pulp 5), BMP: bleached mechanical pulp (pulp 6), UBKP: unbleached Kraft pulp (pulp 3), and BKP: bleached Kraft pulp (pulp 4).

FIG. 27 depicts fluorescence intensity of Probe 3 bound to xylan at the surface of five different paper disks—UBKPR Unbleached Kraft pulp (Pulp 2), UBMP unbleached mechanical pulp (Pulp 5), BMP bleached mechanical pulp (Pulp 6), UBKP unbleached Kraft pulp (Pulp 3); and BKP bleached Kraft pulp (Pulp 4). These results show that Probe 3 has a higher binding affinity towards BKP derived disks compared to the other paper disks. These results may be attributed to the lignin content on the surface of the paper disks. In Kraft pulping, chemicals and heat are used to dissolve the lignin, the binding agent that covers cellulose and hemicellulose. The lignin content of unbleached chemical pulp is approximately 3-5% and bleaching process removes practically all of the remaining lignin, taking it towards 0% of the total content. Mechanical pulping methods preserve most of the wood component so that the lignin content is similar to that of wood (20-28%). Bleached Kraft paper that contains the lowest amount of lignin has been detected by the probe much more efficiently than the other paper disks. This can be ascribed by the increased exposure of xylan on the surface of bleached fibers. This analysis shows that Probe 3 detect xylan on the surface of the paper disks and that it can discriminate between paper surfaces made from different pulps.

Example 13

Figure 28:
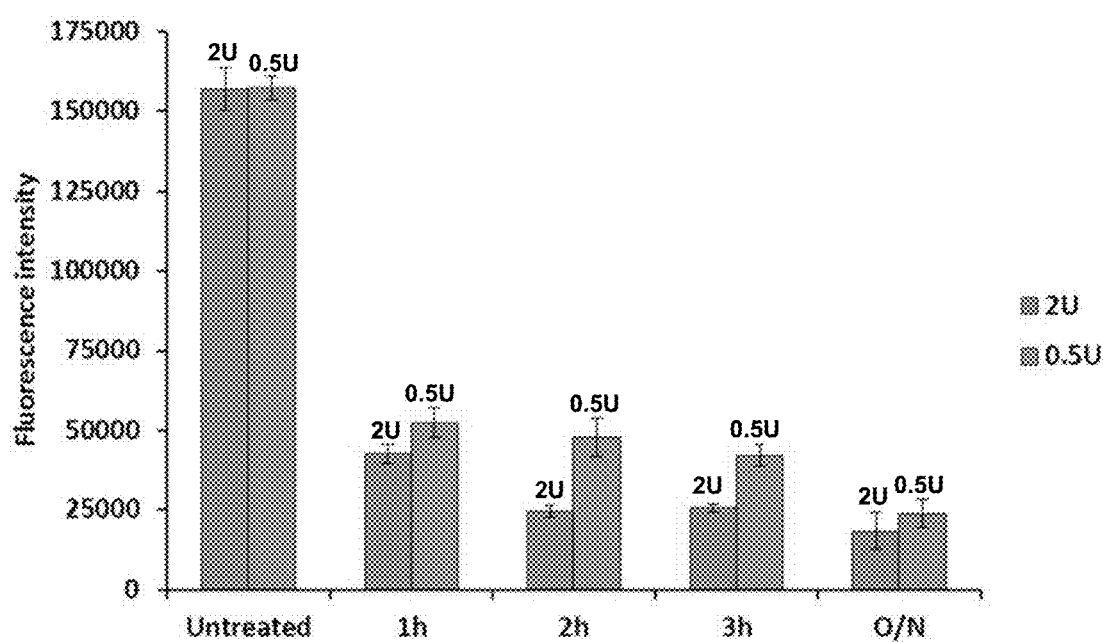
FIG. 28 is an example of a graph depicting fluorescence intensity of Probe 3 bound to xylan at the surface of untreated and xylanase treated Pulp 4 (BKP) paper.

This example demonstrates the detection of xylan removal after enzymatic treatments in accordance with the present invention. The ability to detect xylan was also tested for pulp where xylan content was changed at the fiber surface. In order to demonstrate binding of Probe 3 to xylan unambiguously, paper disks (from bleached Kraft pulp (BKP)) were treated with a commercial xylanase prior detection assay. Xylanase was used at two doses: 0.1 U per paper disk and 0.4 U per paper disk. Results are shown in FIG. 28. FIG. 28 depicts fluorescence intensity of Probe 3 bound to xylan at the surface of untreated and xylanase treated Pulp 4 (BKP) paper. Treatment duration is indicated on the x axis. Untreated indicates Pulp 4 paper disks without xylanase treatment. "O/N" indicates paper treated with xylanase overnight at room temperature. Binding of Probe 3 was reduced by almost 80% after xylanase treatment, establishing that the method detects variations in polymers at the surface of fibers.

Example 14

This example demonstrates the detection of mannan on the surface of paper disks in accordance with the present invention. A high content of mannan (and redeposition on the surface of cellulose fiber during the Kraft pulping) may inhibit the bleaching process. Accordingly, mannanase, in addition with xylanase, is used for prebleaching. In order to optimize mannanase treatment, it is useful to determine mannan content before and after prebleaching.

Two different grades of pulp (Pulp 3: unbleached Kraft pulp (UBKP) and pulp 4: bleached Kraft pulp (BKP)) were investigated with respect to their mannan content. The assay was performed in 96 well-microplates with each well containing a small handsheet disk (60 g/m2). The specific detection of mannan on the surface of such disks made from different pulps was achieved by binding the eCFP-CBM27 protein fusion, also named Probe 4. The fluorescence intensity was measured after incubating the paper disks with 200 µl solution of Probe 4. The excess Probe 4, as well as non-specific binding of the same adduct to any other moieties, was removed by washing 3 times with a TWEEN 20 solution (0.05%). Fluorescence intensity from bound Probe 4 was measured at a wavelength of 477 nm (excitation wavelength 434 nm) using a SYNERGY Mx microplate reader. The fluorescence intensities of the bound probes are presented in FIG. 29.

Figure 29:
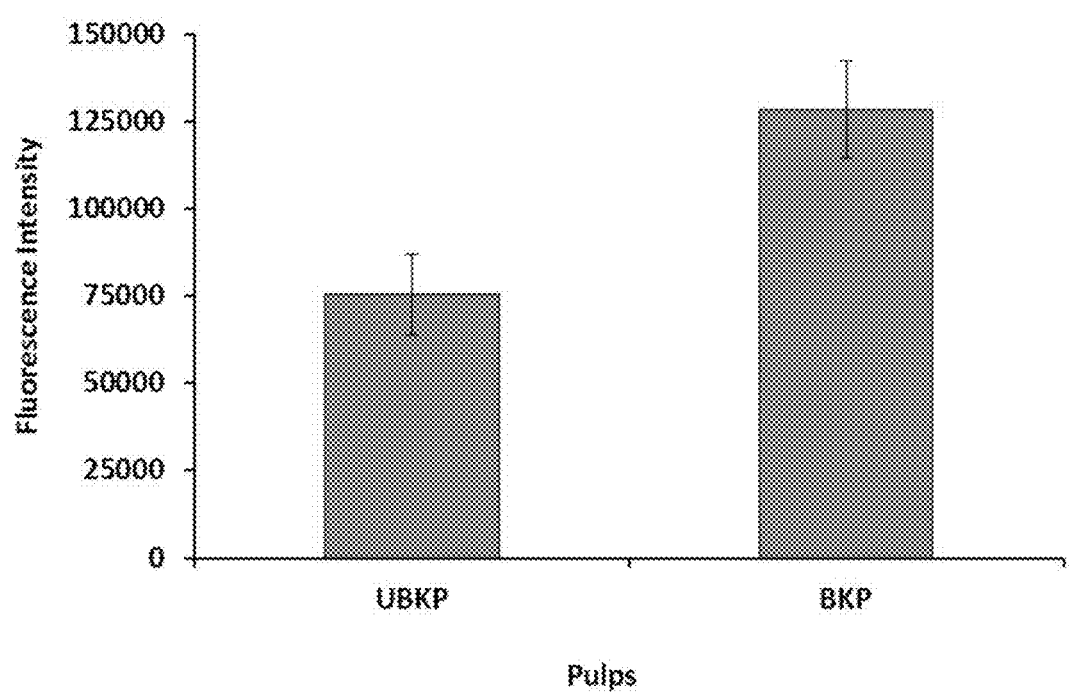
FIG. 29 is an example of a graph depicting fluorescence intensity of Probe 4 (eCFP-CBM27) bound to mannan at the surface of two different paper disks—unbleached Kraft pulp (Pulp 3, UBKP) and bleached Kraft pulp (Pulp 4, BKP).

FIG. 29 depicts fluorescence intensity of Probe 4 (eCFP-CBM27) bound to mannan at the surface of two different paper disks: unbleached Kraft pulp (Pulp 3, UBKP) and bleached Kraft pulp (Pulp 4, BKP). These results show that Probe 4 has a higher binding affinity towards Pulp 4 (BKP) derived disks compared to the pulp 3 (UBKP) paper disks. These results may be attributed to the redeposit of the hemicelluloses and to the lignin content on the surface of the paper disks of pulp 4 (BKP). In Kraft pulping, chemicals and heat are used to dissolve lignin, the binding agent that covers cellulose and hemicellulose. Thus the lignin content drops from 3-5% down to nearly zero. So, mannan in bleached Kraft paper (that contains the lowest amount of lignin) has been detected by the probe much more efficiently than the other paper disks. This result reflects the increased exposure of mannan on the surface of bleached fibers.

Example 15

Figure 30:
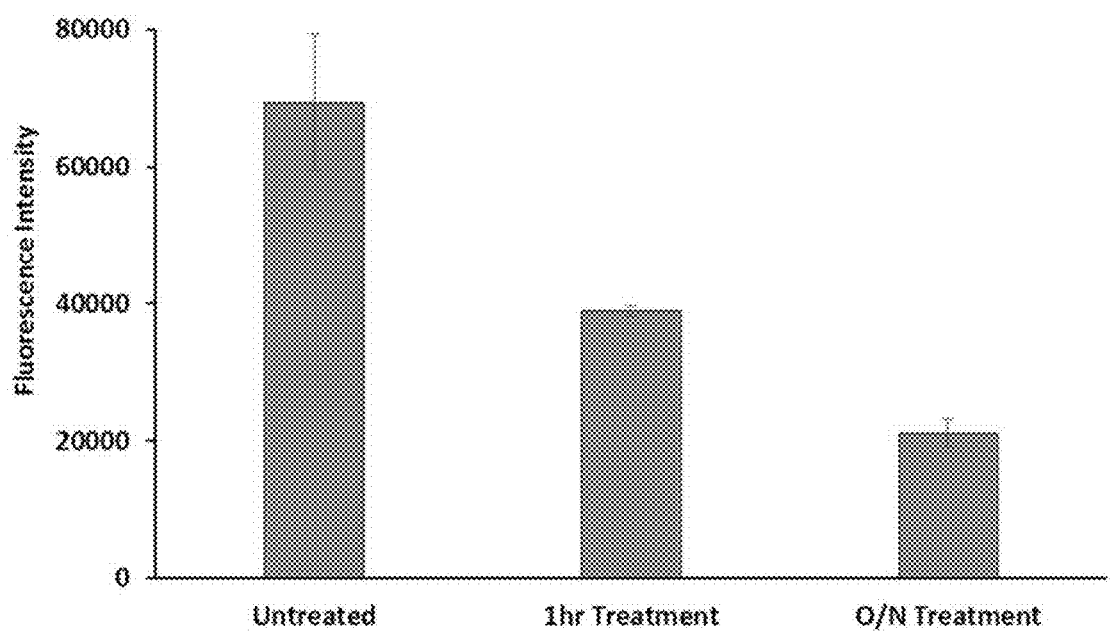
FIG. 30 is an example of a graph depicting fluorescence intensity of Probe 4 bound to mannan at the surface of mannanase-treated bleached Kraft pulp (Pulp 4, BKP) paper.

This example demonstrates the detection of mannan removal after enzymatic treatment in accordance with the present invention. The ability to detect mannan at the surface of fibers was tested. In order to show the binding of Probe 4 to mannan unambiguously, paper disks (from bleached Kraft pulp (Pulp 4, BKP)) were treated with a commercial mannanase (MEGAZYME-E-BMANN) enzyme prior to detection assay. Results are shown in FIG. 30. FIG. 30 depicts fluorescence intensity of Probe 4 bound to mannan at the surface of mannanase-treated bleached Kraft pulp (Pulp 4, BKP) paper. Binding of Probe 4 was reduced by almost 44% after a 1 hour treatment with mannanase. These results clearly demonstrate that the method detects variations in polymers at the surface of fibers.

The present invention includes the following aspects/embodiments/features in any order and/or in any combination:

1. A lignocellulosic polymer detection probe comprising a) a binding module that specifically binds to at least one lignocellulosic polymer and b) a reporter module that is spectroscopically detectable.

2. The probe of any preceding or following embodiment/feature/aspect, wherein the lignocellulosic polymer detection probe comprises a probe polypeptide.

3. The probe of any preceding or following embodiment/feature/aspect, wherein the binding module is a binding module polypeptide and the reporter module is a reporter module polypeptide.

4. The probe of any preceding or following embodiment/feature/aspect, wherein the binding module polypeptide is fused directly to the reporter module polypeptide.

5. The probe of any preceding or following embodiment/feature/aspect, wherein the binding module polypeptide is linked to the reporter polypeptide via a linker polypeptide.

6. The probe of any preceding or following embodiment/feature/aspect, wherein the probe polypeptide comprises an amino acid sequence of any one of SEQ ID NOS: 2, 6, 8, 10, and 12.

7. The probe of any preceding or following embodiment/feature/aspect, wherein the binding module polypeptide comprises an amino acid sequence of any one of SEQ ID NOS: 14, 16, 18, 20, and 22 and the reporter module polypeptide comprises an amino acid sequence of any one of SEQ ID NOS: 24, 26, 28, and 30.

8. The probe of any preceding or following embodiment/feature/aspect, wherein the binding module polypeptide is not an antibody or a fragment thereof.

9. The probe of any preceding or following embodiment/feature/aspect, wherein the reporter module is not an antibody or a fragment thereof.

10. The probe of any preceding or following embodiment/feature/aspect, wherein the reporter module is not a polypeptide.

11. The probe of any preceding or following embodiment/feature/aspect, wherein the reporter module is fluorescent.

12. The probe of any preceding or following embodiment/feature/aspect, wherein the reporter module has a fluorescence excitation peak (maximum) of from about 350 nm to about 700 nm.

13. The probe of any preceding or following embodiment/feature/aspect, wherein the reporter module has a fluorescence emission peak (maximum) of from about 400 nm to about 750 nm.

14. The probe of any preceding or following embodiment/feature/aspect, wherein the reporter module comprises a fluorescent protein.

15. The probe of any preceding or following embodiment/feature/aspect, wherein the fluorescent protein comprises an ultraviolet fluorescent protein, a blue fluorescent protein, a cyan fluorescent protein, a green fluorescent protein, a yellow fluorescent protein, an orange fluorescent protein, a red fluorescent protein, a far-red fluorescent protein, a near infrared fluorescent protein, an infrared fluorescent protein, a sapphire-type fluorescent protein, a long Stokes shift fluorescent protein, a switchable fluorescent protein, or any combination thereof.

16. The probe of any preceding or following embodiment/feature/aspect, wherein the fluorescent protein comprises Sirius, TagBFP, mTagBFP2, Azurite, EBFP2, mKalama1, Sirius, Sapphire, T-Sapphire, ECFP, mAmetrine, Cerulean, mCerulean3, SCFP3A, CyPet, mTurguoise, mTurquoise2, monomeric Midoriishi-Cyan, Aquamarine, eCFP, TagCFP, mTFP1, AmCyan1, EGFP, Emerald, Superfolder GFP, monomeric Azami Green, TurboGFP, TagGFP2, mUKG, mWasabi, Clover, mNeonGreen, eGFP, AcGFP1, ZGreen1, ZsYellow1, mBanana, EYFP, Topaz, Citrine, Venus, SYFP2, Ypet, IanRFP-deltaS83, mPapaya1, TagYFP, mOrange, mOrange2, monomeric Kusabira-Orange, mKOk, mKO2, mTangerine, mNectarine, TagRFP, TagRFP-T, mApple, mRuby, mRuby2, DsRed-Express2, DsRed-Express, tdTomato, DsRed-Monomer, DsRed-Monomer, DsRed2, AsRed2, mStrawberry, mCherry, HcRed1, FusionRed, mRaspberry, E2-Crimson, mPlum, HcRed-Tandem, mKate2, mNeptune, NirFP, TagRFP657, TagRFP675, iFP1.4, iRFP(iRFP713), iRFP670, iRFP682, iRFP702, iRFP720, iFP2.0, mIFP, mKeima Red, LSS-mKatel, LSS-mKate2, LSSmOrange, mBeRFP, PA-GFP, PATag RFP, Dendra2, Timer, PAmCherry, Kaede (green), Kaeda (red), KikGR1 (green), KikGR1 (red), PS-CFP2, mEos2 (green), mEos2 (red), mEos3.2 (green), mEos3.2(red), PSmOrange, Dropna, or any combination thereof.

17. The probe of any preceding or following embodiment/feature/aspect, wherein binding module is a carbohydrate-binding module (CBM) comprising CBM1, CBM2, CBM3, CBM3a CBM4, CBM5, CBM6, CBM9, CBM10, CBM11, CBM12, CBM14, CBM15, CBM17, CBM18, CBM19, CBM20, CBM21, CBM25, CBM27, CBM28, CBM33, CBM48, CBM49, or any combination thereof.

18. The probe of any preceding or following embodiment/feature/aspect, wherein the binding module specifically binds to cellulose, hemicellulose, lignin, xylan, mannan, or any combination thereof.

19. The probe of any preceding or following embodiment/feature/aspect, wherein the binding module specifically binds to crystallized cellulose.

20. The probe of any preceding or following embodiment/feature/aspect, wherein the lignocellulosic polymer detection probe comprises a plurality of lignocellulosic polymer detection probes, each lignocellulosic polymer detection probe specifically binding to a different lignocellulosic polymer.

21. The probe of any preceding or following embodiment/feature/aspect, wherein each lignocellulosic polymer detection probe comprises a different reporter module.

22. The probe of any preceding or following embodiment/feature/aspect, wherein each reporter module has a different fluorescence signature.

23. The probe of any preceding or following embodiment/feature/aspect, wherein the reporter modules comprise one or more of eGFP, mCherry, mOrange2, and eCFP.

24. The probe of any preceding or following embodiment/feature/aspect, wherein the binding modules comprise one or more of CBM3a, CBM4-1, CBM15, and CBM27.

25. The probe of any preceding or following embodiment/feature/aspect, wherein the lignocellulosic polymer detection probe comprises eGFP-CBM3a, mCherry-CBM4-1, mOrange2-CBM15, eCFP-CBM27, or any combination thereof.

26. The probe of any preceding or following embodiment/feature/aspect, wherein the lignocellulosic polymer detection probe is detectable at a distinct wavelength.

27. A complex comprising the probe of any preceding or following embodiment/feature/aspect specifically bound to a pulp or paper product comprising at least one surface available lignocellulosic polymer.

28. A pulp or paper product comprising at least one surface available lignocellulosic polymer and at least one probe of any preceding or following embodiment/feature/aspect specifically bound thereto.

29. A method of detecting a lignocellulosic polymer, the method comprising:
contacting the probe of any one of any preceding or following embodiment/feature/aspect with a biomass material; and
measuring a property associated with the reporter module to determine the presence or absence of at least one lignocellulosic polymer in the biomass material based on specific binding of the probe to the at least one lignocellulosic polymer.

30. The method of any preceding or following embodiment/feature/aspect, wherein the property measured is fluorescence.

31. The method of any preceding or following embodiment/feature/aspect, further comprising calculating the amount of the at least one lignocellulosic polymer, determining the type of the at least one lignocellulosic polymer, or both.

32. The method of any preceding or following embodiment/feature/aspect, wherein the biomass material comprises a wood biomass material.

33. The method of any preceding or following embodiment/feature/aspect, wherein the wood biomass material is pulp, furnish, paper, or any combination thereof.

34. The method of any preceding or following embodiment/feature/aspect, further comprising forming at least one handsheet from the wood biomass product, wherein the measuring is performed on the handsheet.

35. The method of any preceding or following embodiment/feature/aspect, wherein the measuring is performed before treatment, during treatment, or after treatment, or any combination thereof.

36. The method of any preceding or following embodiment/feature/aspect, wherein the treatment comprises an enzymatic treatment, bleaching, amorphogenesis, milling, or PFI refining, or any combination thereof.

37. The method of any preceding or following embodiment/feature/aspect, wherein the treatment comprises enzymatic treatment with at least one enzyme comprising a cellulase, a xylanase, a mannase, a lignase, or any combination thereof.

38. The method of any preceding or following embodiment/feature/aspect, further comprising performing at least one treatment of the biomass material based on the amount of the at least one lignocellulosic polymer measured, the type of lignocellulosic polymer measured, or both.

39. The method of any preceding or following embodiment/feature/aspect, wherein the amount of lignocellulosic polymer measured correlates negatively or positively with at least one physical property of the biomass product.

40. The method of any preceding or following embodiment/feature/aspect, wherein the at least one physical property comprises burst index, drainage rate, tear index, tensile index, or internal bond strength, or any combination thereof.

41. The method of any preceding or following embodiment/feature/aspect, further comprising dosing at least one enzyme based on the amount of lignocellulosic polymer measured, the type of lignocellulosic polymer measured, or both.

42. The method of any preceding or following embodiment/feature/aspect, further comprising adjusting mill speed based on the amount of lignocellulosic polymer measured, the type of lignocellulosic polymer measured, or both.

43. The method of any preceding or following embodiment/feature/aspect, further comprising adjusting total water content of the biomass material based on the amount of lignocellulosic polymer measured, the type of lignocellulosic polymer measured, or both.

44. The method of any preceding or following embodiment/feature/aspect, wherein the probe comprises a plurality of probes.

45. A method of determining the effectiveness of an industrial treatment on pulp or a paper product comprising:
contacting the lignocellulosic polymer detection probe of any one of any preceding or following embodiment/feature/aspect with pulp or a paper product;
detecting the specific binding of the probe to the pulp or the paper product;
calculating the amount of at least one lignocellulosic polymer on a surface of the pulp or the paper product; and
determining the effectiveness of an industrial treatment on the pulp or paper product based on the amount of the at least one lignocellulosic polymer detected.

46. The method of any preceding or following embodiment/feature/aspect, wherein the industrial treatment comprises an enzymatic treatment, a chemical treatment, or a physical treatment, or any combination thereof.

47. The method of any preceding or following embodiment/feature/aspect, wherein the method is performed before the industrial treatment, during the industrial treatment, or after the industrial treatment, or any combination thereof.

48. The method of any preceding or following embodiment/feature/aspect, wherein the lignocellulosic polymer detection probe is detectable at a distinct wavelength.

49. A method of determining a physical property of pulp or a paper product comprising:
contacting the lignocellulosic polymer detection probe of any preceding or following embodiment/feature/aspect with pulp or a paper product;
detecting the specific binding of the probe to the pulp or the paper product;
calculating the amount of at least one lignocellulosic polymer on a surface of the pulp or the paper product; and
determining at least one physical property of the pulp or paper product based on the amount of the at least one lignocellulosic polymer detected.

50. The method of any preceding or following embodiment/feature/aspect, wherein the at least one physical property comprises burst index, drainage rate, tear index, tensile index, or internal bond strength, or any combination thereof.

51. A polymer detection probe comprising a) a binding module that specifically binds to at least one polymer and b) a reporter module that is spectroscopically detectable.

52. The probe of any preceding or following embodiment/feature/aspect, wherein the polymer detection probe comprises a probe polypeptide.

53. The probe of any preceding or following embodiment/feature/aspect, wherein the reporter module is fluorescent.

54. The probe of any preceding or following embodiment/feature/aspect, wherein the reporter module comprises a fluorescent protein.

55. The probe of any preceding or following embodiment/feature/aspect, wherein the fluorescent protein comprises an ultraviolet fluorescent protein, a blue fluorescent protein, a cyan fluorescent protein, a green fluorescent protein, a yellow fluorescent protein, an orange fluorescent protein, a red fluorescent protein, a far-red fluorescent protein, a near infrared fluorescent protein, an infrared fluorescent protein, a sapphire-type fluorescent protein, a long Stokes shift fluorescent protein, a switchable fluorescent protein, or any combination thereof.

56. The probe of any preceding or following embodiment/feature/aspect, wherein binding module is a carbohydrate-binding module (CBM).

57. The probe of any preceding or following embodiment/feature/aspect, wherein the binding module specifically binds to cellulose, hemicellulose, lignin, xylan, mannan, glucuronoxylan, arabinoxylan, glucomannan, xyloglucan, or any combination thereof or a linear fragment thereof, or a branched fragment thereof, or an oligomer thereof, or a monomer and/or macromer thereof, for example, glucose, D-glucose, mannose, xylose, galactose, rhamnose, arabinose, monolignol, p-coumaryl alcohol, coniferyl alcohol, sinapyl alcohol, p-hydroxyphenyl phenylpropanoid, guaiacyl phenylpropanoid, or syringyl phenylpropanoid, or a combination thereof.

58. The probe of any preceding or following embodiment/feature/aspect, wherein the binding module specifically binds to a glycoprotein, carbohydrate, or both, specific to a particular blood antigen, type, group, or subgroup.

59. The probe of any preceding or following embodiment/feature/aspect, wherein the binding module specifically binds to a polyaryletherketone (PAEK), a polyether ether ketone (PEEK), a polyethylene, a polypropylene, a polystyrene, a polytetrfluoroethylene, a polyvinylchloride, a polyamide, a para-aramid, a polyethylene terephthalate, a polyimide, a polycarbonate, a polypeptide, a polynucleotide, a glycoprotein, a protein, a phosphorylated protein, a modified protein, a lipid, a surfactant, lecithin, or a biosurfactant, or any combination thereof.

60. The probe of any preceding or following embodiment/feature/aspect, wherein the polymer detection probe comprises a plurality of polymer detection probes, each polymer detection probe specifically binding to a different polymer.

61. The probe of any preceding or following embodiment/feature/aspect, wherein each polymer detection probe comprises a different reporter module.

62. The probe of any preceding or following embodiment/feature/aspect, wherein each reporter module has a different fluorescence signature.

63. The probe of any preceding or following embodiment/feature/aspect, wherein the polymer detection probe is detectable at a distinct wavelength.

64. A complex comprising the probe of any preceding or following embodiment/feature/aspect specifically bound to a material comprising at least one surface available polymer.

65. A method of detecting a polymer, the method comprising:
    contacting the probe of any preceding or following embodiment/feature/aspect with a material; and
    measuring a property associated with the reporter module to determine the presence or absence of at least one polymer in the material based on specific binding of the probe to the at least one polymer.

66. The method of any preceding or following embodiment/feature/aspect, wherein the property measured is fluorescence.

67. The method of any preceding or following embodiment/feature/aspect, further comprising calculating the amount of the at least one polymer, determining the type of the at least one polymer, or both.

68. The method of any preceding or following embodiment/feature/aspect, wherein the material comprises a blood sample.

69. The method of any preceding or following embodiment/feature/aspect, further comprising determining at least one of a blood antigen, type, group, and subgroup of the blood sample.

70. The method of any preceding or following embodiment/feature/aspect, wherein the probe comprises a plurality of probes.

71. The probe of any preceding or following embodiment/feature/aspect, wherein said polymer is at least one saccharide polymer.

72. The probe of any preceding or following embodiment/feature/aspect, wherein said polymer is at least one oligosaccharide polymer.

The present invention can include any combination of these various features or embodiments above and/or below as set forth in sentences and/or paragraphs. Any combination of disclosed features herein is considered part of the present invention and no limitation is intended with respect to combinable features.

The following references are incorporated by reference herein in their entireties:
Linder, M. et al. (1996) J Biol Chem 271, 21268-21272.
McLean, B. W. et al. (2002) J Biol Chem 277, 50245-50254.
Hilden, L. et al. (2003) Biotechnology letters 25, 553-558.
Lehtio, J. et al. (2003) Proc Natl Acad Sci USA 100, 484-489.
Czjzek et al., J Biol Chem. 2001 Dec. 21; 276(51):48580-7. Epub 2001 Oct. 22.
Ding, S.-Y. et al. (2006) BioTechniques 41, 435-443.
McCartney, L. et al. (2006) Proc Natl Acad Sci USA 103, 4765-4770.
Hong, J. et al. (2007) Langmuir: the ACS journal of surfaces and colloids 23, 12535-12540.
Herve, C. et al. (2010) Proc Natl Acad Sci USA 107, 15293-15298.
Gourlay, K. et al. (2012) Biotechnology for biofuels 5, 51.
Knox, J. P. (2012) Methods in enzymology 510, 233-245.
Ruel, K. et al. (2012) Plant science: an international journal of experimental plant biology 193-194, 48-61.
Luis, A. S. et al. (2013) J. Biol. Chem. 288, 4799-4809,
Zhang, M. et al. (2013) Physical chemistry chemical physics: PCCP 15, 6508-6515.
Mou et al. (2013) Bioresources 8, 2325-2336.
Machado et al., (2009) Cellulose 16, 817-824.
Kim et al. (2010) Planta 232, 817-824.
Kim et al. (2012) Planta 236, 35-50.
Široký et al. (2012) Carbohyd. Polym. 89, 213-221.
Gao et al., (2014) Biotechnology for biofuels 7, 24.
Filonova et al. (2007) Biomacromolecules 8, 91-97.
Carbohydrate-Binding-Modules.html on Mar. 30, 2015.
U.S. Pat. Nos. 5,856,201; 5,837,814; 5,738,984; 5,719,044; 5,670,623; 6,174,700; 5,962,289; 7,361,487; 5,928,917,
Boraston et al., Biochem J., 382: 769-781 (2004),
Shoseyov et al., Microbiology and Molecular Biology Reviews, 70(2): 283-295 (2006),
Christiansen et al., FEBS Journal, 276:5006-5029 (2009).

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

SEQUENCE LISTING

SEQ ID NO: 1 (nucleic acid) for eGFP-CBM3a (Probe 1). The underlined text represents the thrombin cleavage site which link eGFP to CBM3a.
ATGGGTCATCACCATCACCATCACGGTGTGAGCAAGGGCGAGGAGCTGTT
CACCGGGGTGGTGCCCATCCTGGTCGAGCTGGACGGCGACGTAAACGGCC
ACAAGTTCAGCGTGTCCGGCGAGGGCGAGGGCGATGCCACCTACGGCAAG
CTGACCCTGAAGTTCATCTGCACCACCGGCAAGCTGCCCGTGCCTTGGCC
CACCCTCGTGACCACCCTGACCTACGGCGTGCAGTGCTTCAGCCGCTACC
CCGACCACATGAAGCAGCACGACTTCTTCAAGTCCGCCATGCCCGAAGGC
TACGTCCAGGAGCGCACCATCTTCTTCAAGGACGACGGCAACTACAAGAC
CCGCGCCGAGGTGAAGTTCGAGGGCGACACCCTGGTGAACCGCATCGAGC
TGAAGGGCATCGACTTCAAGGAGGACGGCAACATCCTGGGGCACAAGCTG
GAGTACAACTACAACAGCCACAACGTCTATATCATGGCCGACAAGCAGAA
GAACGGCATCAAGGTGAACTTCAAGATCCGCCACAACATCGAGGACGGCA
GCGTCGAGCTCGCCGACCACTACCAGCAGAACACCCCCATCGGCGACGGC
CCCGTGCTGCTGCCCGACAACCACTACCTGAGCACCCAGTCCGCCCTGAG
CAAAGACCCCAACGAGAAGCGCGATCACATGGTCCTGCTGGAGTTCGTGA
CCGCCGCCGGGATCACTCTCGGCATGGACGAGCTGTACAAAAGTTCCGGT
CTGGTGCCGCGTGGTAGCACACCGGTATCAGGCAATTTGAAGGTTGAATT
CTACAACAGCAATCCTTCAGATACTACTAACTCAATCAATCCTCAGTTCA
AGGTTACTAATACCGGAAGCAGTGCAATTGATTTGTCCAAACTCACATTG
AGATATTATTATACAGTAGACGGACAGAAAGATCAGACCTTCTGGTGTGA
CCATGCTGCAATAATCGGCAGTAACGGCAGCTACAACGGAATTACTTCAA
ATGTAAAAGGAACATTTGTAAAAATGAGTTCCTCAACAAATAACGCAGAC
ACCTACCTTGAAATTAGCTTTACAGGCGGAACTCTTGAACCGGGTGCACA
TGTTCAGATACAAGGTAGATTTGCAAAGAATGACTGGAGTAACTATACAC
AGTCAAATGACTACTCATTCAAGTCTGCTTCACAGTTTGTTGAATGGGAT
CAGGTAACAGCATACTTGAACGGTGTTCTTGTATGGGGTAAAGAATAA SEQ ID NO: 2 (amino acid) for eGFP-CBM3a (Probe 1). The underlined text represents the thrombin cleavage site which link eGFP to CBM3a.
MGHHHHHHGVSKGEELFTGVVPILVELDGDVNGHKFSVSGEGEGDATYGK
LTLKFICTTGKLPVPWPTLVTTLTYGVQCFSRYPDHMKQHDFFKSAMPEG
YVQERTIFFKDDGNYKTRAEVKFEGDTLVNRIELKGIDFKEDGNILGHKL
EYNYNSHNVYIMADKQKNGIKVNFKIRHNIEDGSVQLADHYQQNTPIGDG
PVLLPDNHYLSTQSALSKDPNEKRDHMVLLEFVTAAGITLGMDELYK<u>SSG
LVPRGS</u>TPVSGNLKVEFYNSNPSDTTNSINPQFKVTNTGSSAIDLSKLTL
RYYYTVDGQKDQTFWCDHAAIIGSNGSYNGITSNVKGTFVKMSSSTNNAD
TYLEISFTGGTLEPGAHVQIQGRFAKNDWSNYTQSNDYSFKSASQFVEWD
QVTAYLNGVLVWGKE SEQ ID NO: 3 for Probe 1 linker.
AGTTCCGGTCTGGTGCCGCGTGGTAGC SEQ ID NO: 4 (amino acid) for Probe 1 linker.
SSGLVPRGS SEQ ID NO: 5 (nucleic acid) for mCherry-CBM4-1 (Probe 2a). The underlined text represents the glycine which link mCheiTy to CBM4-1.
ATGGGTCATCACCATCACCATCACGGTGTGAGCAAGGGCGAGGAGGATAA
CATGGCCATCATCAAGGAGTTCATGCGCTTCAAGGTGCACATGGAGGGCT
CCGTGAACGGCCACGAGTTCGAGATCGAGGGCGAGGGCGAGGGCCGCCCC
TACGAGGGCACCCAGACCGCCAAGCTGAAGGTGACCAAGGGTGGCCCCCT
GCCCTTCGCCTGGGACATCCTGTCCCCTCAGTTCATGTACGGCTCCAAGG
CCTACGTGAAGCACCCCGCCGACATCCCCGACTACTTGAAGCTGTCCTTC
CCCGAGGGCTTCAAGTGGGAGCGCGTGATGAACTTCGAGGACGGCGGCGT
GGTGACCGTGACCCAGGACTCCTCCCTGCAGGACGGCGAGTTCATCTACA
AGGTGAAGCTGCGCGGCACCAACTTCCCCTCCGACGGCCCCGTAATGCAG
AAGAAGACCATGGGCTGGGAGGCCTCCTCCGAGCGGATGTACCCCGAGGA
CGGCGCCCTGAAGGGCGAGATCAAGCAGAGGCTGAAGCTGAAGGACGGCG
GCCACTACGACGCTGAGGTCAAGACCACCTACAAGGCCAAGAAGCCCGTG
CAGCTGCCCGGCGCCTACAACGTCAACATCAAGTTGGACATCACCTCCCA
CAACGAGGACTACACCATCGTGGAACAGTACGAACGCGCCGAGGGCCGCC ACTCCACCGGCGGCATGGACGAGCTGTACAAG<u>GGT</u>GCGTCGCCGATCGGG
GAGGGAACGTTCGACGACGGGCCCGAGGGGTGGGTCGCGTACGGCACCGA
CGGCCCCCTCGACACGAGCACGGGCGCGCTGTGCGTCGCCGTGCCGGCCG
GCTCCGCGCAGTACGGCGTCGGCGTCGTGCTCAACGGCGTCGCGATCGAG
GAAGGGACCACCTACACGCTCCGGTACACCGCGACGGCCTCGACCGACGT
CACCGTGCGGGCGCTCGTCGGGCAGAACGGCGCCCCTACGGCACCGTGC
TCGACACGAGCCCGGCCCTGACGTCCGAGCCCGCGGCAGGTGACCGAGACG
TTCACGGCCTCGGCGACGTACCCCGCGACACCCGCCGCCGACGACCCCGA
GGGGCAGATCGCCTTCCAGCTCGGCGGGTTCAGCGCCGACGCGTGGACGT
TCTGCCTCGACGACGTCGCGCTCGACTCCGAGGTCGAGCTCTAA SEQ ID NO: 6 (amino acid) for mCherry-CBM4-1 (Probe 2a). The underlined text represents the glycine which link mCherry to CBM4-1.
MGHHHHHHGVSKGEEDNMAIIKEFMRFKVHMEGSVNGHEFEIEGEGEGRP
YEGTQTAKLKVTKGGPLPFAWDILSPQFMYGSKAYVKHPADIPDYLKLSF
PEGFKWERVMNFEDGGVVTVTQDSSLQDGEFIYKVKLRGTNFPSDGPVMQ
KKTMGWEASSERMYPEDGALKGEIKQRLKLKDGGHYDAEVKTTYKAKKPV
QLPGAYNVNIKLDITSHNEDYTIVEQYERAEGRHSTGGMDELYK<u>G</u>ASPIG
EGTFDDGPEGWVAYGTDGPLDTSTGALCVAVPAGSAQYGVGVVLNGVAIE
EGTTYTLRYTATASTDVTVRALVGQNGAPYGTVLDTSPALTSEPRQVTET
FTASATYPATPAADDPEGQIAFQLGGFSADAWTFCLDDVALDSEVEL SEQ ID NO: 7 (nucleic acid) for mCherry-CBM17 (Probe 2b). The underlined text represents the glycine codon that link mCherry to CBM17.
ATGGGTCATCACCATCACCATCACGGTGTGAGCAAGGGCGAGGAGGATAA
CATGGCCATCATCAAGGAGTTCATGCGCTTCAAGGTGCACATGGAGGGCT
CCGTGAACGGCCACGAGTTCGAGATCGAGGGCGAGGGCGAGGGCCGCCCC
TACGAGGGCACCCAGACCGCCAAGCTGAAGGTGACCAAGGGTGGCCCCCT
GCCCTTCGCCTGGGACATCCTGTCCCCTCAGTTCATGTACGGCTCCAAGG
CCTACGTGAAGCACCCCGCCGACATCCCCGACTACTTGAAGCTGTCCTTC
CCCGAGGGCTTCAAGTGGGAGCGCGTGATGAACTTCGAGGACGGCGGCGT
GGTGACCGTGACCCAGGACTCCTCCCTGCAGGACGGCGAGTTCATCTACA
AGGTGAAGCTGCGCGGCACCAACTTCCCCTCCGACGGCCCCGTAATGCAG
AAGAAGACCATGGGCTGGGAGGCCTCCTCCGAGCGGATGTACCCCGAGGA
CGGCGCCCTGAAGGGCGAGATCAAGCAGAGGCTGAAGCTGAAGGACGGCG
GCCACTACGACGCTGAGGTCAAGACCACCTACAAGGCCAAGAAGCCCGTG
CAGCTGCCCGGCGCCTACAACGTCAACATCAAGTTGGACATCACCTCCCA
CAACGAGGACTACACCATCGTGGAACAGTACGAACGCGCCGAGGGCCGCC
ACTCCACCGGCGGCATGGACGAGCTGTACAAG<u>GGT</u>TATGGGCAGATAAT
GAATTAACCACTTCAGGTCAATATGTACGTGCTCGTATTAAGGGAGCTTA
TTATGCTACACCAGTTGATCCTGTAACAAACCAACCAACAGCACCGAAAG
ACTTTTCTTCAGGCTTTTGGGACTTTAATGACGGTACTACACAAGGTTTT
GGTGTAAATCCAGATAGTCCAATAACTGCTATTAATGTTGAAAATGCTAA
CAATGCTTTAAAAATCAGCAATCTTAATAGTAAGGGTAGTAATGATTTAT
CTGAAGGAAACTTTTGGGCCAATGTCCGCATTTCAGCTGATATCTGGGGA
CAAAGTATAAATATATATGGAGACACAAAACTAACAATGGATGTTATAGC
TCCAACACCTGTAAATGTATCAATCGCAGCTATCCCACAAAGTAGTACTC
ACGGTTGGGGAAATCCTACAAGAGCTATACGTGTTTGGACAAACAACTTT
GTAGCACAAACTGATGGAACCTATAAAGCAACTTTGACCATTTCTACAAA
CGATAGTCCAAATTTCAATACTATAGCTACAGATGCTGCTGATAGTGTAG
TAACAAATATGATTCTATTTGTTGGTTCAAATTCAGATAATATTTCTTTA
GACAATATAAAGTTTACTAAATAAGGATCCGGCTGCTAACAAAGCCCGAA
AGGAAGCTGAGTTGGCTGCTGCCACCGCTGAGCAATAACTAGCATAACCC
CTTGGGGCCTCTAA SEQ ID NO: 8 (amino acid) for mCherry-CBM17 (Probe 2b). The underlined text represents the glycine codon that link mCherry to CBM17.
MGHHHHHHGVSKGEEDNMAIIKEFMRFKVHMEGSVNGHEFEIEGEGEGRP
YEGTQTAKLKVTKGGPLPFAWDILSPQFMYGSKAYVKHPADIPDYLKLSF
PEGFKWERVMNFEDGGVVTVTQDSSLQDGEFIYKVKLRGTNFPSDGPVMQ
KKTMGWEASSERMYPEDGALKGEIKQRLKLKDGGHYDAEVKTTYKAKKPV
QLPGAYNVNIKLDITSHNEDYTIVEQYERAEGRHSTGGMDELYK<u>G</u>LWADN
ELTTSGQYVRARIKGAYYATPVDPVTNQPTAPKDFSSGFWDFNDGTTQGF
GVNPDSPITAINVENANNALKISNLNSKGSNDLSEGNFWANVRISADIWG
QSINIYGDTKLTMDVIAPTPVNVSIAAIPQSSTHGWGNPTRAIRVWTNNF
VAQTDGTYKATLTISTNDSPNFNTIATDAADSVVTNMILFVGSNSDNISL
DNIKFTK SEQ ID NO: 9 (nucleic acid) for mOrange2-CBM15 (Probe 3). The underlined text represents the glycine codon that link mOrange2 to CBM15.
ATGGGTCATCACCATCACCATCACGGTGTGAGCAAGGGCGAGGAGAATAA
CATGGCCATCATCAAGGAGTTCATGCGCTTCAAGGTGCGCATGGAGGGCT
CCGTGAACGGCCACGAGTTCGAGATCGAGGGCGAGGGCGAGGGCCGCCCC

SEQUENCE LISTING

TACGAGGGCTTTCAGACCGCTAAGCTGAAGGTGACCAAGGGTGGCCCCCT
GCCCTTCGCCTGGGACATCCTGTCCCCTCATTTCACCTACGGCTCCAAGG
CCTACGTGAAGCACCCCGCCGACATCCCCGACTACTTCAAGCTGTCCTTC
CCCGAGGGCTTCAAGTGGGAGCGCGTGATGAACTACGAGGACGGCGGCGT
GGTGACCGTGACCCAGGACTCCTCCCTGCAGGACGGCGAGTTCATCTACA
AGGTGAAGCTGCGCGGCACCAACTTCCCCTCCGACGGCCCCGTGATGCAG
AAGAAGACCATGGGCTGGGAGGCCTCCTCCGAGCGGATGTACCCCGAGGA
CGGTGCCCTGAAGGGCAAGATCAAGATGAGGCTGAAGCTGAAGGACGGCG
GCCACTACACCTCCGAGGTCAAGACCACCTACAAGGCCAAGAAGCCCGTG
CAGCTGCCCGGCGCCTACATCGTGGACATCAAGTTGGACATCACCTCCCA
CAACGAGGACTACACCATCGTGGAACAGTACGAAGCGCCGAGGGCCGCC
ACTCCACCGGCGGCATGGACGAGCTGTACAAGGGTGTCGCTGCCAGCGAG
GGCAATGTTGTTATAGAGGTGGACATGGCAAATGGCTGGAGAGGCAACGC
ATCAGGCAGTACCAGCCATTCCGGTATTACCTACAGTGCCGATGGCGTTA
CCTTTGCCGCACTGGGCGATGGCGTGGGCGCTGTTTTTGATATTGCCCGA
CCAACCACACTGGAAGATGCTGTGATAGCAATGGTTGTTAATGTCAGCGC
TGAATTTAAGGCCAGTGAAGCCAACTTGCAGATATTTGCCCAGTTAAAAG
AAGACTGGTCAAAGGGCAATGGGATTGTCTGGCGGCCAGCAGCGAACTC
ACTGCGGATACTGACCTAACCCTGACCTGCACCATTGATGAAGACGACGA
TAAATTCAACCAAACGGCGCGATGCAAGTCGGTATCCAGGCCAAGG
GAACACCCGCCGGAACTATCACCATTAAAAGCGTCACCATTACACTCGCA
CAGGAAGCCTATTCAGCCAATTAA

SEQ ID NO: 10 (amino acid) for mOrange2-CBM15
(Probe 3). The underlined text represents the
glycine codon that link mOrange2 to CBM15.
MGHHHHHHGVSKGEENNMAIIKEFMRFKVRMEGSVNGHEFEIEGEGEGRP
YEGFQTAKLKVTKGGPLPFAWDILSPHFTYGSKAYVKHPADIPDYFKLSF
PEGFKWERVMNYEDGGVVTVTQDSSLQDGEFIYKVKLRGTNFPSDGPVMQ
KKTMGWEASSERMYPEDGALKGKIKMRLKLKDGGHYTSEVKTTYKAKKPV
QLPGAYIVDIKLDITSHNEDYTIVEQYERAEGRHSTGGMDELYKGVAASE
GNVVIEVDMANGWRGNASGSTSHSGITYSADGVTFAALGDGVGAVFDIAR
PTTLEDAVIAMVVNVSAEFKASEANLQIFAQLKEDWSKGEWDCLAASSEL
TADTDLTLTCTIDEDDDKFNQTARDVQVGIQAKGTPAGTITIKSVTITLA
QEAYSAN SEQ ID NO: 11 (nucleic acid) for eCFP-CBM27
(Probe 4). The underlined text represents the
glycine codon that link eCFP to CBM27.
ATGGGTCATCACCATCACCATCACGGTGTGAGCAAGGGCGAGGAGCTGTT
CACCGGGGTGGTGCCCATCCTGGTCGAGCTGGACGGCGACGTAAACGGCC
ACAAGTTCAGCGTGTCCGGCGAGGGCGAGGGCGATGCCACCTACGGCAAG
CTGACCCTGAAGTTCATCTGCACCACCGGCAAGCTGCCCGTGCCCTGGCC
CACCCTCGTGACCACCCTGACCTGGGGCGTGCAGTGCTTCAGCCGCTACC
CCGACCACATGAAGCAGCACGACTTCTTCAAGTCCGCCATGCCCGAAGGC
TACGTCCAGGAGCGCACCATCTTCTTCAAGGACGACGGCAACTACAAGAC
CCGCGCCGAGGTGAAGTTCGAGGGCGACACCCTGGTGAACCGCATCGAAC
TGAAGGGCATCGATTTCAAGGAGGACGGCAACATCCTGGGGCACAAGCTG
GAGTACAACTACATCAGCCACAACGTCTATATCACCGCCGACAAGCAGAA
GAACGGCATCAAGGCCAACTTCAAGATCCGCCACAACATCGAGGACGGCA
GCGTGCAGCTCGCCGACCACTACCAGCAGAACACCCCCATCGGCGACGGC
CCCGTGCTGCTGCCCGACAACCACTACCTGAGCACCCAGTCCGCCCTGAG
CAAAGACCCCAACGAGAAGCGCGATCACATGGTCCTGCTGGAGTTCGTGA
CCGCCGCCGGGATCACTCTCGGCATGGACGAGCTGTACAAGGGTAACGAA
GCACGGTACGTGCTCGCAGAGGAAGTTGATTTTCCTCTCCAGAAGAGGT
GAAAACTGGTGGAACAGCGGAACCTGGCAGGCAGAGTTCGGGTCACCTG
ACATTGAATGGAACGGTGAGGTGGGAAATGGAGCACTGCAGCTGAACGTG
AAACTGCCCGGAAAGAGCGACTGGGAAGAAGTGAGAGTAGCAAGGAAGTT
CGAAAGACTCTCAGAATGTGAGATCCTCGAGTACGACATCTACATTCCAA
ACGTCGAGGGACTCAAGGGAAGGTTGAGGCCGTACGCGGTTCTGAACCCC
GGCTGGGTGAAGATAGGCCTCGACATGAACAACGCGAACGTGGAAAGTGC
GGAGATCATCACTTTCGGCGGAAAAGAGTACAGAAGATTCCATGTAAGAA
TTGAGTTCGACAGAACAGCGGGTGAAAGAACTTCACATAGGAGTTGTC
GGTGATCATCTGAGGTACGATGGACCGATTTTCATCGATAATGTGAGACT
TTATAAAGAACAGGAGGTATGTAA SEQ ID NO: 12 (amino acid) for eCFP-CBM27 (Probe
4). The underlined text represents the glycine
codon that link eCFP to CBM27.
MGHHHHHHGVSKGEELFTGVVPILVELDGDVNGHKFSVSGEGEGDATYGK
LTLKFICTTGKLPVPWPTLVTTLTWGVQCFSRYPDHMKQHDFFKSAMPEG
YVQERTIFFKDDGNYKTRAEVKFEGDTLVNRIELKGIDFKEDGNILGHKL
EYNYISHNVYITADKQKNGIKANFKIRHNIEDGSVQLADHYQQNTPIGDG
PVLLPDNHYLSTQSALSKDPNEKRDHMVLLEFVTAAGITLGMDELYKGNE
ARYVLAEEVDFSSPEEVKNWWNSGTWQAEFGSPDIEWNGEVGNGALQLNV
KLPGKSDWEEVRVARKFERLSECEILEYDIYIPNVEGLKGRLRPYAVLNP
GWVKIGLDMNNANVESAEIITFGGKEYRRFHVRIEFDRTAGVKELHIGVV
GDHLRYDGPIFIDNVRLYKRTGGM SEQ ID NO: 13 (nucleic acid) for CBM3a.
ATGGGTCATCACCATCACCATCACGGTACACCGACCAAGGGAGCAACACC
AACAAATACAGCTACGCCGACAAAATCAGCTACGGCTACGCCCACCAGGC
CATCGGTACCGACAAACACACCGACAAACACACCGGCAAATACACCGGTA
TCAGGCAATTTGAAGGTTGAATTCTACAACAGCAATCCTTCAGATACTAC
TAACTCAATCAATCCTCAGTTCAAGGTTACTAATACCGGAAGCAGTGCAA
TTGATTTGTCCAAACTCACATTGAGATATTATTATACAGTAGACGGACAG
AAAGATCAGACCTTCTGGTGTGACCATGCTGCAATAATCGGCAGTAACGG
CAGCTACAACGGAATTACTTCAAATGTAAAAGGAACATTTGTAAAAATGA
GTTCCTCAACAAATAACGCAGACACCTACCTTGAAATTAGCTTTACAGGC
GGAACTCTTGAACCGGGTGCACATGTTCAGATACAAGGTAGATTTGCAAA
GAATGACTGGAGTAACTATACAGTCAAATGACTACTCATTCAAGTCTG
CTTCACAGTTTGTTAATGGGATCAGGTAACAGCATACTTGAACGGTGTT
CTTGTATGGGGTAAAGAATAA SEQ ID NO: 14 (amino acid) for CBM3a.
MGHHHHHHGTPTKGATPTNTATPTKSATATPTRPSVPTNTPTNTPANTPV
SGNLKVEFYNSNPSDTTNSINPQFKVTNTGSSAIDLSKLTLRYYYTVDGQ
KDQTFWCDHAAIIGSNGSYNGITSNVKGTFVKMSSSTNNADTYLEISFTG
GTLEPGAHVQIQGRFAKNDWSNYTQSNDYSFKSASQFVEWDQVTAYLNGV
LVWGKE SEQ ID NO: 15 (nucleic acid) for CBM4-1.
ATGGGTCATCACCATCACCATCACGGTGCGTCGCCGATCGGGGAGGGAAC
GTTCGACGACGGGCCCGAGGGTGGGTCGCGTACGGCACCGACGGCCCCC
TCGACACGAGCACGGGCGCGCTGTGCGTCGCCGTGCCGGCCGGCTCCGCG
CAGTACGGCGTCGGCGTCGTGCTCAACGGCGTCGCGATCGAGGAAGGGAC
CACCTACACGCTCCGGTACACCGCGAGCACCGACGTCACCGTGC
GGGCGCTCGTCGGGCAGAACGGCGCCCCCTACGGCACCGTGCTCGACACG
AGCCCGGCCCTGACGTCCGAGCCGCGGCAGGTGACCGAGACGTTCACGGC
CTCGGCGACGTACCCCGCGACACCCGCCGCGAGCACCCCGAGGGGCAGA
TCGCCTTCCAGCTCGGCGGGTTCAGCGCCGACGCGTGGACGTTCTGCCTC
GACGACGTCGCGCTCGACTCCGAGGTCGAGCTCTAA SEQ ID NO: 16 (amino acid) for CBM4-1.
MGHHHHHHGASPIGEGTFDDGPEGWVAYGTDGPLDTSTGALCVAVPAGSA
QYGVGVVLNGVAIEEGTTYTLRYTATASTDVTVRALVGQNGAPYGTVLDT
SPALTSEPRQVTETFTASATYPATPAADDPEGQIAFQLGGFSADAWTFCL
DDVALDSEVEL SEQ ID NO: 17 (nucleic acid) for CBM17.
ATGGGTCATCACCATCACCATCACGGTTTATGGGCAGATAATGAATTAAC
CACTTCAGGTCAATATGTACGTGCTCGTATTAAGGGAGCTTATTATGCTA
CACCAGTTGATCCTGTAACAAACCAACCAACAGCACCGAAAGACTTTTCT
TCAGGCTTTTGGGACTTTAATGACGGTACTACACAAGGTTTTGGTGTAAA
TCCAGATAGTCCAATAACTGCTATTAATGTTGAAAATGCTAACAATGCTT
TAAAAATCAGCAATCTTAATAGTAAGGGTAGTAATGATTTATCTGAAGGA
AACTTTTGGCCAATGTCCGCATTTCAGCTGATATCTGGGGACAAAGTAT
AAATATATATGGAGACACAAAACTAACAATGGATGTTATAGCTCCAACAC
CTGTAAATGTATCAATCGCAGCTATCCCACAAAGTAGTACTCACGGTTGG
GGAAATCCTACAAGAGCTATACGTGTTTGGACAAACAACTTTGTAGCACA
AACTGATGGAACCTATAAAGCAACTTTGACCATTTCTACAAACGATAGTC
CAAATTTCAATACTATAGCTACAGATGCTGCTGATAGTGTAGTAACAAAT
ATGATTCTATTTGTTGGTTCAAATTCAGATAATATTTCTTTAGACAATAT
AAAGTTTACTAAATAA SEQ ID NO: 18 (amino acid) for CBM17.
MGHHHHHHGLWADNELTTSGQYVRARIKGAYYATPVDPVTNQPTAPKDFS
SGFWDFNDGTTQGFGVNPDSPITAINVENANNALKISNLNSKGSNDLSEG
NFWANVRISADIWGQSINIYGDTKLTMDVIAPTPVNVSIAAIPQSSTHGW
GNPTRAIRVWTNNFVAQTDGTYKATLTISTNDSPNFNTIATDAADSVVTN
MILFVGSNSDNISLDNIKFTK SEQ ID NO: 19 (nucleic acid) for CBM15.
ATGGGTCATCACCATCACCATCACGGTGTCGCTGCCAGCGAGGGCAATGT
TGTTATAGAGGTGGACATGGCAAATGGCTGGAGAGGCAACGCATCAGGCA
GTACCAGCCATTCCGGTATTACCTACAGTGCCGATGGCGTTACCTTTGCC
GCACTGGGCGATGGCGTGGGCGCTGTTTTTGATATTGCCCGACCAACCAC
ACTGGAAGATGCTGTGATAGCAATGGTTGTTAATGTCAGCGCTGAATTTA
AGGCCAGTGAAGCCAACTTGCAGATATTTGCCCAGTTAAAAGAAGACTGG
TCAAAGGGCAATGGGATTGTCTGGCGGCCAGCAGCGAACTCACTGCGGA
TACTGACCTAACCCTGACCTGCACCATTGATGAAGACGACGATAAATTCA

SEQUENCE LISTING

```
ACCAAACGGCGCGCGATGTACAAGTCGGTATCCAGGCCAAGGGAACACCC
GCCGGAACTATCACCATTAAAAGCGTCACCATTACACTCGCACAGGAAGC
CTATTCAGCCAATTAA

SEQ ID NO: 20 (amino acid) for CBM15.
MGHHHHHHGVAASEGNVVIEVDMANGWRGNASGSTSHSGITYSADGVTFA
ALGDGVGAVFDIARPTTLEDAVIAMVVNVSAEFKASEANLQIFAQLKEDW
SKGEWDCLAASSELTADTDLTLTCTIDEDDDICFNQTARDVQVGIQAKGT
PAGTITIKSVTITLAQEAYSAN SEQ ID NO: 21 (nucleic acid) for CBM27.
ATGGGTCATCACCATCACCATCACGGTAACGAAGCACGGTACGTGCTCGC
AGAGAGGATTGATTTTTCCTCCAGAAGAGGTGAAAAACTGGTGGAACA
GCGGAACCTGCAGGCAGAGTTCGGGTCACCTGACATTGAATGGAACGGT
GAGGTGGGAAATGGAGCACTGCAGCTGAACGTGAAACTGCCCGGAAAGA
CGACTGGGAAGAAGTGAGAGTGGCAAGGAAGTTCGAAAGACTCTCAGAAT
GTGAGATCCTCGAGTACGACATCTACATTCCAAACGTCGAGGGACTCAAG
GGAAGGTTGAGGCCGTACGCGGTTCTGAACCCCGGCTGGGTGAAGATAGG
CCTCGACATGAACAACGCGAACGTGGAAAGTGCGGAGATCATCACTTTCG
GCGGAAAAGAGTACAGAAGATTCATGTAAGAATTGAGTTCGACAGAACA
GCGGGGGTGAAAGAACTTCACATAGGAGTTGTCGGTGATCATCTGAGGTA
CGATGGACCGATTTTCATCGATAATGTGAGACTTTATAAAAGAACAGGAG
GTATGTAA SEQ ID NO: 22 (amino acid) for CBM27.
MGHHHHHHGNEARYVLAEEVDFSSPEEVKNWWNSGTWQAEFGSPDIEWNG
EVGNGALQLNVKLPGKSDWEEVRVARKFERLSECEILEYDIYIPNVEGLK
GRLRPYAVLNPGWVKIGLDMNNANVESAEIITFGGKEYRRFHVRIEFDRT
AGVKELHIGVVGDHLRYDGPIFIDNVRLYKRTGGM SEQ ID NO: 23 (nucleic acid) for eGFP.
ATGGGTCATCACCATCACCATCACGGTGTGAGCAAGGGCGAGGAGCTGTT
CACCGGGGTGGTGCCCATCCTGGTCGAGCTGGACGGCGACGTAAACGGCC
ACAAGTTCAGCGTGTCCGGCGAGGGCGAGGGCGATGCCACCTACGGCAAG
CTGACCCTGAAGTTCATCTGCACCACCGGCAAGCTGCCCGTGCCCTGGCC
CACCCTCGTGACCACCCTGACCTACGGCGTGCAGTGCTTCAGCCGCTACC
CCGACCACATGAAGCAGCACGACTTCTTCAAGTCCGCCATGCCCGAAGGC
TACGTCCAGGAGCGCACCATCTTCTTCAAGGACGACGGCAACTACAAGAC
CCGCGCCGAGGTGAAGTTCGAGGGCGACACCCTGGTGAACCGCATCGAGC
TGAAGGGCATCGACTTCAAGGAGGACGGCAACATCCTGGGGCACAAGCTG
GAGTACAACTACAACAGCCACAACGTCTATATCATGGCCGACAAGCAGAA
GAACGGCATCAAGGTGAACTTCAAGATCCGCCACAACATCGAGGACGGCA
GCGTGCAGCTCGCCGACCACTACCAGCAGAACACCCCCATCGGCGACGGC
CGTGCTGCTGCCCGACAACCACTACCTGAGCACCCAGTCCGCCCTGAGCA
AAGACCCCAACGAGAAGCGCGATCACATGGTCCTGCTGGAGTTCGTGACC
GCCGCCGGGATCACTCTCGGCATGGACGAGCTGTACAAGTAA SEQ ID NO: 24 (amino acid) for eGFP.
MGHHHHHHGVSKGEELFTGVVPILVELDGDVNGHKFSVSGEGEGDATYGK
LTLKFICTTGKLPVPWPTLVTTLTYGVQCFSRYPDHMKQHDFFKSAMPEG
YVQERTIFFKDDGNYKTRAEVKFEGDTLVNRIELKGIDFKEDGNILGHKL
EYNYNSHNVYIMADKQKNGIKVNFKIRHNIEDGSVQLADHYQQNTPIGDG
PVLLPDNHYLSTQSALSKDPNEKRDHMVLLEFVTAAGITLGMDELYK SEQ ID NO: 25 (nucleic acid) for mCherry.
ATGGGTCATCACCATCACCATCACGGTGTGAGCAAGGGCGAGGAGGATAA
CATGGCCATCATCAAGGAGTTCATGCGCTTCAAGGTGCACATGGAGGGCT
CCGTGAACGGCCACGAGTTCGAGATCGAGGGCGAGGGCGAGGGCCGCCCC
TACGAGGGCACCCAGACCGCCAAGCTGAAGGTGACCAAGGGTGGCCCCCT
GCCCTTCGCCTGGGACATCCTGTCCCCTCAGTTCATGTACGGCTCCAAGG
CCTACGTGAAGCACCCCGCCGACATCCCCGACTACTTGAAGCTGTCCTTC
CCCGAGGGCTTCAAGTGGGAGCGCGTGATGAACTTCGAGGACGGCGGCGT
GGTGACCGTGACCCAGGACTCCTCCCTGCAGGACGGCGAGTTCATCTACA
```

```
AGGTGAAGCTGCGCGGCACCAACTTCCCCTCCGACGGCCCCGTAATGCAG
AAGAAGACCATGGGCTGGGAGGCCTCCTCCGAGCGGATGTACCCCGAGGA
CGGCGCCCTGAAGGGCGAGATCAAGCAGAGGCTGAAGCTGAAGGACGGCG
GCCACTACGACGCTGAGGTCAAGACCACCTACAAGGCCAAGAAGCCCGTG
CAGCTGCCCGGCGCCTACAACGTCAACATCAAGTTGGACATCACCTCCCA
CAACGAGGACTACACCATCGTGGAACAGTACGAACGCGCCGAGGGCCGCC
ACTCCACCGGCGGCATGGACGAGCTGTACAAGTAA

SEQ ID NO: 26 (amino acid) for mCherry.
MGHHHHHHGVSKGEEDNMAIIKEFMRFKVHMEGSVNGHEFEIEGEGEGRP
YEGTQTAKLKVTKGGPLPFAWDILSPQFMYGSKAYVKHPADIPDYLKLSF
PEGFKWERVMNFEDGGVVTVTQDSSLQDGEFIYKVKLRGTNFPSDGPVMQ
KKTMGWEASSERMYPEDGALKGEIKQRLKLKDGGHYDAEVKTTYKAKKPV
QLPGAYNVNIKLDITSHNEDYTIVEQYERAEGRHSTGGMDELYK SEQ ID NO: 27 (nucleic acid) for mOrange2.
ATGGGTCATCACCATCACCATCACGGTGTGAGCAAGGGCGAGGAGAATAA
CATGGCCATCATCAAGGAGTTCATGCGCTTCAAGGTGCGCATGGAGGGCT
CCGTGAACGGCCACGAGTTCGAGATCGAGGGCGAGGGCGAGGGCCGCCCC
TACGAGGGCTTTCAGACCGCTAAGCTGAAGGTGACCAAGGGTGGCCCCCT
GCCCTTCGCCTGGGACATCCTGTCCCCTCATTTCACCTACGGCTCCAAGG
CCTACGTGAAGCACCCCGCCGACATCCCCGACTACTTCAAGCTGTCCTTC
CCCGAGGGCTTCAAGTGGGAGCGCGTGATGAACTACGAGGACGGCGGCGT
GGTGACCGTGACCCAGGACTCCTCCCTGCAGGACGGCGAGTTCATCTACA
AGGTGAAGCTGCGCGGCACCAACTTCCCCTCCGACGGCCCCGTGATGCAG
AAGAAGACCATGGGCTGGGAGGCCTCCTCCGAGCGGATGTACCCCGAGGA
CGGTGCCCTGAAGGGCAAGATCAAGATGAGGCTGAAGCTGAAGGACGGCG
GCCACTACACCTCCGAGGTCAAGACCACCTACAAGGCCAAGAAGCCCGTG
CAGCTGCCCGGCGCCTACATCGTCGACATCAAGTTGGACATCACCTCCCA
CAACGAGGACTACACCATCGTGGAACAGTACGAACGCGCCGAGGGCCGCC
ACTCCACCGGCGGCATGGACGAGCTGTACAAGTAA SEQ ID NO: 28 (amino acid) for mOrange2.
MGHHHHHHGVSKGEENNMAIIKEFMRFKVRMEGSVNGHEFEIEGEGEGRP
YEGFQTAKLKVTKGGPLPFAWDILSPHFTYGSKAYVKHPADIPDYFKLSF
PEGFKWERVMNYEDGGVVTVTQDSSLQDGEFIYKVKLRGTNFPSDGPVMQ
KKTMGWEASSERMYPEDGALKGKIKMRLKLKDGGHYTSEVKTTYKAKKPV
QLPGAYIVDIKLDITSHNEDYTIVEQYERAEGRHSTGGMDELYK SEQ ID NO: 29 (nucleic acid) for eCFP.
ATGGGTCATCACCATCACCATCACGGTGTGAGCAAGGGCGAGGAGCTGTT
CACCGGGGTGGTGCCCATCCTGGTCGAGCTGGACGGCGACGTAAACGGCC
ACAAGTTCAGCGTGTCCGGCGAGGGCGAGGGCGATGCCACCTACGGCAAG
CTGACCCTGAAGTTCATCTGCACCACCGGCAAGCTGCCCGTGCCCTGGCC
CACCCTCGTGACCACCCTGACCTGGGGCGTGCAGTGCTTCAGCCGCTACC
CCGACCACATGAAGCAGCACGACTTCTTCAAGTCCGCCATGCCCGAAGGC
TACGTCCAGGAGCGCACCATCTTCTTCAAGGACGACGGCAACTACAAGAC
CCGCGCCGAGGTGAAGTTCGAGGGCGACACCCTGGTGAACCGCATCGAGC
TGAAGGGCATCGACTTCAAGGAGGACGGCAACATCCTGGGGCACAAGCTG
GAGTACAACTACATCAGCCACAACGTCTATATCACCGCCGACAAGCAGAA
GAACGGCATCAAGGCCAACTTCAAGATCCGCCACAACATCGAGGACGGCA
GCGTGCAGCTCGCCGACCACTACCAGCAGAACACCCCCATCGGCGACGGC
CCCGTGCTGCTGCCCGACAACCACTACCTGAGCACCCAGTCCGCCCTGAG
CAAAGACCCCAACGAGAAGCGCGATCACATGGTCCTGCTGGAGTTCGTGA
CCGCCGCCGGGATCACTCTCGGCATGGACGAGCTGTACAAGTAA SEQ ID NO: 30 (amino acid) for eCFP.
MGHHHHHHGVSKGEELFTGVVPILVELDGDVNGHKFSVSGEGEGDATYGK
LTLKFICTTGKLPVPWPTLVTTLTWGVQCFSRYPDHMKQHDFFKSAMPEG
YVQERTIFFKDDGNYKTRAEVKFEGDTLVNRIELKGIDFKEDGNILGHKL
EYNYISHNVYITADKQKNGIKANFKIRHNIEDGSVQLADHYQQNTPIGDG
PVLLPDNHYLSTQSALSKDPNEKRDHMVLLEFVTAAGITLGMDELYK
```

---

What is claimed is:

1. A method of detecting a lignocellulosic polymer, the method comprising:
   contacting a lignocellulosic polymer detection probe with a biomass material, said lignocellulosic polymer detection probe comprising a) a binding module that specifically binds to at least one lignocellulosic polymer and b) a reporter module that is spectroscopically detectable, wherein the binding module is a binding module polypeptide that comprises the amino acid sequence of SEQ ID NO: 14, 16, 18, 20, or 22, and wherein the reporter module is a reporter module polypeptide that comprises the amino acid sequence of SEQ ID NO: 24, 26, 28, or 30; and
   measuring a property associated with the reporter module to determine the presence or absence of at least one lignocellulosic polymer in the biomass material based on specific binding of the probe to the at least one lignocellulosic polymer.

2. The method of claim 1, wherein the property measured is fluorescence.

3. The method of claim 1, further comprising calculating the amount of the at least one lignocellulosic polymer, determining the type of the at least one lignocellulosic polymer, or both.

4. The method of claim 1, wherein the biomass material comprises a wood biomass material.

5. The method of claim 4, wherein the wood biomass material pulp, furnish, paper, or any combination thereof.

6. The method of claim 5, further comprising forming at least one handsheet from the wood biomass product, wherein the measuring is performed on the handsheet.

7. The method of claim 1, wherein the measuring is performed before treatment, during treatment, or after treatment, or any combination thereof.

8. The method of claim 7, wherein the treatment comprises an enzymatic treatment, bleaching, amorphogenesis, milling, or PFI refining, or any combination thereof.

9. The method of claim 7, wherein the treatment comprises enzymatic treatment with at least one enzyme comprising a cellulase, a xylanase, a mannase, a lignase, or any combination thereof.

10. The method of claim 3, further comprising performing at least one treatment of the biomass material based on the amount of the at least one lignocellulosic polymer measured, the type of lignocellulosic polymer measured, or both.

11. The method of claim 3, wherein the amount of lignocellulosic polymer measured correlates negatively or positively with at least one physical property of the biomass material.

12. The method of claim 11, wherein the at least one physical property comprises burst index, drainage rate, tear index, tensile index, or internal bond strength, or any combination thereof.

13. The method of claim 3, further comprising dosing at least one enzyme based on the amount of lignocellulosic polymer measured, the type of lignocellulosic polymer measured, or both.

14. The method of claim 3, further comprising adjusting mill speed based on the amount of lignocellulosic polymer measured, the type of lignocellulosic polymer measured, or both.

15. The method of claim 3, further comprising adjusting total water content of the biomass material based on the amount of lignocellulosic polymer measured, the type of lignocellulosic polymer measured, or both.

16. The method of claim 1, wherein the probe comprises a plurality of probes.

17. A method of determining the effectiveness of an industrial treatment on pulp or a paper product comprising:
contacting a lignocellulosic polymer detection probe with a pulp or a paper product, said lignocellulosic polymer detection probe comprising a) a binding module that specifically binds to at least one lignocellulosic polymer and b) a reporter module that is spectroscopically detectable, wherein the binding module is a binding module polypeptide that comprises the amino acid sequence of SEQ ID NO: 14, 16, 18, 20, or 22, and wherein the reporter module is a reporter module polypeptide that comprises the amino acid sequence of SEQ ID NO: 24, 26, 28, or 30;
detecting the specific binding of the probe to the pulp or the paper product;
calculating the amount of at least one lignocellulosic polymer on a surface of the pulp or the paper product; and
determining the effectiveness of an industrial treatment on the pulp or paper product based on the amount of the at least one lignocellulosic polymer detected.

18. The method of claim 17, wherein the industrial treatment comprises an enzymatic treatment, a chemical treatment, or a physical treatment, or any combination thereof.

19. The method of claim 17, wherein the method is performed before the industrial treatment, during the industrial treatment, or after the industrial treatment, or any combination thereof.

20. The method of claim 17, wherein the lignocellulosic polymer detection probe is detectable at a distinct wavelength.

21. A method of determining a physical property of pulp or a paper product comprising:
contacting a lignocellulosic polymer detection probe with a pulp or a paper product, said lignocellulosic polymer detection probe comprising a) a binding module that specifically binds to at least one lignocellulosic polymer and b) a reporter module that is spectroscopically detectable, wherein the binding module is a binding module polypeptide that comprises the amino acid sequence of SEQ ID NO: 14, 16, 18, 20, or 22, and wherein the reporter module is a reporter module polypeptide that comprises the amino acid sequence of SEQ ID NO: 24, 26, 28, or 30;
detecting the specific binding of the probe to the pulp or the paper product;
calculating the amount of at least one lignocellulosic polymer on a surface of the pulp or the paper product; and
determining at least one physical property of the pulp or paper product based on the amount of the at least one lignocellulosic polymer detected.

22. The method of claim 21, wherein the at least one physical property comprises burst index, drainage rate, tear index, tensile index, or internal bond strength, or any combination thereof.

23. A method of detecting a polymer, the method comprising:
contacting a polymer detection probe with a material, said polymer detection probe comprising a) a binding module that specifically binds to at least one polymer and b) a reporter module that is spectroscopically detectable, wherein the binding module is a binding module polypeptide polypeptide that comprises the amino acid sequence of SEQ ID NO: 14, 16, 18, 20, or 22, and wherein the reporter module is a reporter module polypeptide that comprises the amino acid sequence of SEQ ID NO: 24, 26, 28, or 30; and
measuring a property associated with the reporter module to determine the presence or absence of at least one polymer in the material based on specific binding of the probe to the at least one polymer.

24. The method of claim 23, wherein the property measured is fluorescence.

25. The method of claim 23, further comprising calculating the amount of the at least one polymer, determining the type of the at least one polymer, or both.

26. The method of claim 23, wherein the material comprises a blood sample.

27. The method of 26, further comprising determining at least one of a blood antigen, type, group, and subgroup of the blood sample.

28. The method of claim 23, wherein the probe comprises a plurality of probes.

29. The method of claim 1, wherein the binding module polypeptide is fused directly to the reporter module polypeptide.

30. The method of claim 1, wherein the binding module polypeptide is linked to the reporter polypeptide via a linker polypeptide.

31. The method of claim 1, wherein the reporter module has a fluorescence excitation peak (maximum) of from about 350 nm to about 700 nm.

32. The method of claim 1, wherein the reporter module has a fluorescence emission peak (maximum) of from about 400 nm to about 750 nm.

33. The method of claim 1, wherein the binding module specifically binds to cellulose, hemicellulose, lignin, xylan, mannan, or any combination thereof.

34. The method of claim 1, wherein the binding module specifically binds to crystallized cellulose.

35. The method of claim 1, wherein the lignocellulosic polymer detection probe comprises a plurality of lignocellulosic polymer detection probes, each lignocellulosic polymer detection probe specifically binding to a different lignocellulosic polymer.

36. The method of claim 35, wherein each lignocellulosic polymer detection probe comprises a different reporter module.

37. The method of claim 35, wherein each reporter module has a different fluorescence signature.

38. The method of claim 1, wherein the lignocellulosic polymer detection probe comprises eGFP-CBM3a, mCherry-CBM4-1, mOrange2-CBM15, eCFP-CBM27, or any combination thereof.

39. The method of claim 1, wherein the lignocellulosic polymer detection probe is detectable at a distinct wavelength.

40. The method of claim 13, wherein the binding module specifically binds to cellulose, hemicellulose, lignin, xylan, mannan, glucuronoxylan, arabinoxylan, glucomannan, xyloglucan, or any combination thereof or a linear fragment thereof, or a branched fragment thereof, or an oligomer thereof, or a monomer and/or macromer thereof.

41. The method of claim 13, wherein the binding module specifically binds to a glycoprotein, carbohydrate, or both, specific to a particular blood antigen, type, group, or subgroup.

42. The method of claim 13, wherein the binding module specifically binds to a polyaryletherketone (PAEK), a polyether ether ketone (PEEK), a polyethylene, a polypropylene, a polystyrene, a polytetrfluoroethylene, a polyvinylchloride, a polyamide, a para-aramid, a polyethylene terephthalate, a polyimide, a polycarbonate, a polypeptide, a polynucleotide, a glycoprotein, a protein, a phosphorylated protein, a modified protein, a lipid, a surfactant, lecithin, or a biosurfactant, or any combination thereof.

43. The method of claim 13, wherein the polymer detection probe comprises a plurality of polymer detection probes, each polymer detection probe specifically binding to a different polymer.

44. The method of claim 43, wherein each polymer detection probe comprises a different reporter module.

45. The method of claim 43, wherein each reporter module has a different fluorescence signature.

46. The method of claim 44, wherein the polymer detection probe is detectable at a distinct wavelength.

* * * * *

SEQUENCE LISTING

<160> NUMBER OF SEQ ID NOS: 30

<210> SEQ ID NO 1
<211> LENGTH: 1248
<212> TYPE: DNA
<213> ORGANISM: Artificial Sequence
<220> FEATURE:
<223> OTHER INFORMATION: Nucleic acid sequence for eGFP-CBM3a (Probe 1).

```
<220> FEATURE:
<221> NAME/KEY: misc_feature
<222> LOCATION: (742)..(768)
<223> OTHER INFORMATION: Thrombin cleavage site that links eGFP to
      CBM3a.

<400> SEQUENCE: 1
atgggtcatc accatcacca tcacggtgtg agcaagggcg aggagctgtt caccggggtg       60
gtgcccatcc tggtcgagct ggacggcgac gtaaacggcc acaagttcag cgtgtccggc      120
gagggcgagg gcgatgccac ctacggcaag ctgaccctga agttcatctg caccaccggc      180
aagctgcccg tgccctggcc caccctcgtg accaccctga cctacggcgt gcagtgcttc      240
agccgctacc ccgaccacat gaagcagcac gacttcttca gtccgccat gcccgaaggc       300 tacgtccagg agcgcaccat cttcttcaag gacgacggca actacaagac ccgcgccgag      360
gtgaagttcg agggcgacac cctggtgaac cgcatcgagc tgaagggcat cgacttcaag      420
gaggacggca acatcctggg gcacaagctg gagtacaact acaacagcca caacgtctat      480
atcatggccg acaagcagaa gaacggcatc aaggtgaact tcaagatccg ccacaacatc      540
gaggacggca gcgtgcagct cgccgaccac taccagcaga acacccccat cggcgacggc      600
cccgtgctgc tgcccgacaa ccactacctg agcacccagt ccgccctgag caaagacccc      660
aacgagaagc gcgatcacat ggtcctgctg gagttcgtga ccgccgccgg gatcactctc      720
ggcatggacg agctgtacaa aagttccggt ctggtgccgc gtggtagcac accggtatca      780
ggcaatttga aggttgaatt ctacaacagc aatccttcag atactactaa ctcaatcaat      840
cctcagttca aggttactaa taccggaagc agtgcaattg atttgtccaa actcacattg      900
agatattatt atacagtaga cggacagaaa gatcagacct tctggtgtga ccatgctgca      960
ataatcggca gtaacggcag ctacaacgga attacttcaa atgtaaaagg aacatttgta     1020
aaaatgagtt cctcaacaaa taacgcagac acctaccttg aaattagctt tacaggcgga     1080
actcttgaac cgggtgcaca tgttcagata caaggtagat tgcaaagaa tgactggagt       1140 aactatacac agtcaaatga ctactcattc aagtctgctt cacagtttgt tgaatgggat     1200
caggtaacag catacttgaa cggtgttctt gtatggggta agaataa                   1248

<210> SEQ ID NO 2
<211> LENGTH: 415
<212> TYPE: PRT
<213> ORGANISM: Artificial Sequence
<220> FEATURE:
<223> OTHER INFORMATION: Amino acid sequence for eGFP-CBM3a (Probe 1).
<220> FEATURE:
<221> NAME/KEY: misc_feature
<222> LOCATION: (248)..(256)
<223> OTHER INFORMATION: Thrombin cleavage site that links eGFP to
      CBM3a.

<400> SEQUENCE: 2

Met Gly His His His His His His Gly Val Ser Lys Gly Glu Glu Leu
1               5                   10                  15

Phe Thr Gly Val Val Pro Ile Leu Val Glu Leu Asp Gly Asp Val Asn
            20                  25                  30

Gly His Lys Phe Ser Val Ser Gly Glu Gly Glu Gly Asp Ala Thr Tyr
        35                  40                  45

Gly Lys Leu Thr Leu Lys Phe Ile Cys Thr Thr Gly Lys Leu Pro Val
    50                  55                  60

Pro Trp Pro Thr Leu Val Thr Thr Leu Thr Tyr Gly Val Gln Cys Phe
65                  70                  75                  80
```

Ser Arg Tyr Pro Asp His Met Lys Gln His Asp Phe Phe Lys Ser Ala
                85                  90                  95

Met Pro Glu Gly Tyr Val Gln Glu Arg Thr Ile Phe Phe Lys Asp Asp
            100                 105                 110

Gly Asn Tyr Lys Thr Arg Ala Glu Val Lys Phe Glu Gly Asp Thr Leu
        115                 120                 125

Val Asn Arg Ile Glu Leu Lys Gly Ile Asp Phe Lys Glu Asp Gly Asn
130                 135                 140

Ile Leu Gly His Lys Leu Glu Tyr Asn Tyr Asn Ser His Asn Val Tyr
145                 150                 155                 160

Ile Met Ala Asp Lys Gln Lys Asn Gly Ile Lys Val Asn Phe Lys Ile
                165                 170                 175

Arg His Asn Ile Glu Asp Gly Ser Val Gln Leu Ala Asp His Tyr Gln
            180                 185                 190

Gln Asn Thr Pro Ile Gly Asp Gly Pro Val Leu Leu Pro Asp Asn His
        195                 200                 205

Tyr Leu Ser Thr Gln Ser Ala Leu Ser Lys Asp Pro Asn Glu Lys Arg
210                 215                 220

Asp His Met Val Leu Leu Glu Phe Val Thr Ala Ala Gly Ile Thr Leu
225                 230                 235                 240

Gly Met Asp Glu Leu Tyr Lys Ser Ser Gly Leu Val Pro Arg Gly Ser
                245                 250                 255

Thr Pro Val Ser Gly Asn Leu Lys Val Glu Phe Tyr Asn Ser Asn Pro
            260                 265                 270

Ser Asp Thr Thr Asn Ser Ile Asn Pro Gln Phe Lys Val Thr Asn Thr
        275                 280                 285

Gly Ser Ser Ala Ile Asp Leu Ser Lys Leu Thr Leu Arg Tyr Tyr Tyr
290                 295                 300

Thr Val Asp Gly Gln Lys Asp Gln Thr Phe Trp Cys Asp His Ala Ala
305                 310                 315                 320

Ile Ile Gly Ser Asn Gly Ser Tyr Asn Gly Ile Thr Ser Asn Val Lys
                325                 330                 335

Gly Thr Phe Val Lys Met Ser Ser Thr Asn Asn Ala Asp Thr Tyr
            340                 345                 350

Leu Glu Ile Ser Phe Thr Gly Gly Thr Leu Glu Pro Gly Ala His Val
        355                 360                 365

Gln Ile Gln Gly Arg Phe Ala Lys Asn Asp Trp Ser Asn Tyr Thr Gln
370                 375                 380

Ser Asn Asp Tyr Ser Phe Lys Ser Ala Ser Gln Phe Val Glu Trp Asp
385                 390                 395                 400

Gln Val Thr Ala Tyr Leu Asn Gly Val Leu Val Trp Gly Lys Glu
                405                 410                 415

<210> SEQ ID NO 3
<211> LENGTH: 27
<212> TYPE: DNA
<213> ORGANISM: Artificial Sequence
<220> FEATURE:
<223> OTHER INFORMATION: Nucleic acid sequence for probe 1 linker.

<400> SEQUENCE: 3
agttccggtc tggtgccgcg tggtagc                                    27

<210> SEQ ID NO 4
<211> LENGTH: 9

<212> TYPE: PRT
<213> ORGANISM: Artificial Sequence
<220> FEATURE:
<223> OTHER INFORMATION: Amino acid sequence for Probe 1 linker.

<400> SEQUENCE: 4

Ser Ser Gly Leu Val Pro Arg Gly Ser
1               5

<210> SEQ ID NO 5
<211> LENGTH: 1194
<212> TYPE: DNA
<213> ORGANISM: Artificial Sequence
<220> FEATURE:
<223> OTHER INFORMATION: Nucleic acid sequence for mCherry-CBM4-1 (Probe
      2a).
<220> FEATURE:
<221> NAME/KEY: misc_feature
<222> LOCATION: (733)..(735)
<223> OTHER INFORMATION: Glycine codon that links mCherry to CBM4-1.

<400> SEQUENCE: 5
atgggtcatc accatcacca tcacggtgtg agcaagggcg aggaggataa catggccatc      60
atcaaggagt tcatgcgctt caaggtgcac atggagggcc cgtgaacgg ccacgagttc     120 gagatcgagg gcgagggcga gggccgcccc tacgagggca cccagaccgc caagctgaag     180
gtgaccaagg gtggcccect gcccttcgcc tgggacatcc tgtcccctca gttcatgtac     240
ggctccaagg cctacgtgaa gcaccccgcc gacatccccg actacttgaa gctgtccttc     300
cccgagggct tcaagtggga gcgcgtgatg aacttcgagg acggcggcgt ggtgaccgtg     360
acccaggact cctccctgca ggacggcgag ttcatctaca aggtgaagct gcgcggcacc     420
aacttcccct ccgacggccc cgtaatgcag aagaagacca tgggctggga ggcctcctcc     480
gagcggatgt accccgagga cggcgccctg aagggcgaga tcaagcagag gctgaagctg     540
aaggacggcg ccactacga cgctgaggtc aagaccacct acaaggccaa gaagcccgtg     600
cagctgcccg gcgcctacaa cgtcaacatc aagttggaca tcacctccca caacgaggac     660
tacaccatcg tggaacagta cgaacgcgcc gagggccgcc actccaccgg cggcatggac     720
gagctgtaca agggtgcgtc gccgatcggg gagggaacgt cgacgacgg gcccgagggg     780 tgggtcgcgt acggcaccga cggcccccctc gacacgagca cgggcgcgct gtgcgtcgcc     840
gtgccggccg gctccgcgca gtacggcgtc ggcgtcgtgc tcaacggcgt cgcgatcgag     900
gaagggacca cctacacgct ccggtacacc gcgacggcct cgaccgacgt caccgtgcgg     960
gcgctcgtcg gcagaacgg cgcccctac ggcaccgtgc tcgacacgag cccggccctg    1020
acgtccgagc cgcggcaggt gaccgagacg ttcacggcct cggcgacgta ccccgcgaca    1080
cccgccgccg acgaccccga ggggcagatc gccttccagc tcggcgggtt cagcgccgac    1140
gcgtggacgt tctgcctcga cgacgtcgcg ctcgactccg aggtcgagct ctaa          1194

<210> SEQ ID NO 6
<211> LENGTH: 397
<212> TYPE: PRT
<213> ORGANISM: Artificial Sequence
<220> FEATURE:
<223> OTHER INFORMATION: Amino acid sequence for mCherry-CBM4-1 (Probe
      2a).
<220> FEATURE:
<221> NAME/KEY: misc_feature
<222> LOCATION: (245)..(245)
<223> OTHER INFORMATION: Glycine that links mCherry to CBM4-1.

<400> SEQUENCE: 6

```
Met Gly His His His His His Gly Val Ser Lys Gly Glu Glu Asp
1               5                   10                  15

Asn Met Ala Ile Ile Lys Glu Phe Met Arg Phe Lys Val His Met Glu
            20                  25                  30

Gly Ser Val Asn Gly His Glu Phe Glu Ile Glu Gly Glu Gly Glu Gly
        35                  40                  45

Arg Pro Tyr Glu Gly Thr Gln Thr Ala Lys Leu Lys Val Thr Lys Gly
    50                  55                  60

Gly Pro Leu Pro Phe Ala Trp Asp Ile Leu Ser Pro Gln Phe Met Tyr
65                  70                  75                  80

Gly Ser Lys Ala Tyr Val Lys His Pro Ala Asp Ile Pro Asp Tyr Leu
                85                  90                  95

Lys Leu Ser Phe Pro Glu Gly Phe Lys Trp Glu Arg Val Met Asn Phe
            100                 105                 110

Glu Asp Gly Gly Val Val Thr Val Thr Gln Asp Ser Ser Leu Gln Asp
        115                 120                 125

Gly Glu Phe Ile Tyr Lys Val Lys Leu Arg Gly Thr Asn Phe Pro Ser
    130                 135                 140

Asp Gly Pro Val Met Gln Lys Lys Thr Met Gly Trp Glu Ala Ser Ser
145                 150                 155                 160

Glu Arg Met Tyr Pro Glu Asp Gly Ala Leu Lys Gly Glu Ile Lys Gln
                165                 170                 175

Arg Leu Lys Leu Lys Asp Gly Gly His Tyr Asp Ala Glu Val Lys Thr
            180                 185                 190

Thr Tyr Lys Ala Lys Lys Pro Val Gln Leu Pro Gly Ala Tyr Asn Val
        195                 200                 205

Asn Ile Lys Leu Asp Ile Thr Ser His Asn Glu Asp Tyr Thr Ile Val
    210                 215                 220

Glu Gln Tyr Glu Arg Ala Glu Gly Arg His Ser Thr Gly Gly Met Asp
225                 230                 235                 240

Glu Leu Tyr Lys Gly Ala Ser Pro Ile Gly Glu Gly Thr Phe Asp Asp
                245                 250                 255

Gly Pro Glu Gly Trp Val Ala Tyr Gly Thr Asp Gly Pro Leu Asp Thr
            260                 265                 270

Ser Thr Gly Ala Leu Cys Val Ala Val Pro Ala Gly Ser Ala Gln Tyr
        275                 280                 285

Gly Val Gly Val Val Leu Asn Gly Val Ala Ile Glu Glu Gly Thr Thr
    290                 295                 300

Tyr Thr Leu Arg Tyr Thr Ala Thr Ala Ser Thr Asp Val Thr Val Arg
305                 310                 315                 320

Ala Leu Val Gly Gln Asn Gly Ala Pro Tyr Gly Thr Val Leu Asp Thr
                325                 330                 335

Ser Pro Ala Leu Thr Ser Glu Pro Arg Gln Val Thr Glu Thr Phe Thr
            340                 345                 350

Ala Ser Ala Thr Tyr Pro Ala Thr Pro Ala Ala Asp Pro Glu Gly
        355                 360                 365

Gln Ile Ala Phe Gln Leu Gly Gly Phe Ser Ala Asp Ala Trp Thr Phe
    370                 375                 380

Cys Leu Asp Asp Val Ala Leu Asp Ser Glu Val Glu Leu
385                 390                 395

<210> SEQ ID NO 7
<211> LENGTH: 1464
```

```
<212> TYPE: DNA
<213> ORGANISM: Artificial Sequence
<220> FEATURE:
<223> OTHER INFORMATION: Nucleic acid sequence for mCherry-CBM17 (Probe
      2b).
<220> FEATURE:
<221> NAME/KEY: misc_feature
<222> LOCATION: (733)..(735)
<223> OTHER INFORMATION: Glycine codon that links mCherry to CBM17.

<400> SEQUENCE: 7
atgggtcatc accatcacca tcacggtgtg agcaagggcg aggaggataa catggccatc      60
atcaaggagt tcatgcgctt caaggtgcac atggagggct ccgtgaacgg ccacgagttc     120
gagatcgagg gcgagggcga gggccgcccc tacgagggca cccagaccgc caagctgaag     180
gtgaccaagg gtggcccccc tgcccttcgcc tgggacatcc tgtcccctca gttcatgtac    240
ggctccaagg cctacgtgaa gcaccccgcc gacatccccg actacttgaa gctgtccttc     300
cccgagggct tcaagtggga gcgcgtgatg aacttcgagg acggcggcgt ggtgaccgtg     360
acccaggact cctccctgca ggacggcgag ttcatctaca aggtgaagct gcgcggcacc     420
aacttcccct ccgacggccc cgtaatgcag aagaagacca tgggctggga ggcctcctcc     480
gagcggatgt accccgagga cggcgccctg aagggcgaga tcaagcagag gctgaagctg     540
aaggacggcg ccactacga cgctgaggtc aagaccacct acaaggccaa gaagcccgtg      600
cagctgcccg gcgcctacaa cgtcaacatc aagttggaca tcacctccca caacgaggac     660
tacaccatcg tggaacagta cgaacgcgcc gagggccgcc actccaccgg cggcatggac     720
gagctgtaca agggttatg gcagataat gaattaacca cttcaggtca atatgtacgt       780
gctcgtatta agggagctta ttatgctaca ccagttgatc ctgtaacaaa ccaaccaaca     840
gcaccgaaag acttttcttc aggcttttgg gactttaatg acggtactac acaaggtttt    900
ggtgtaaatc cagatagtcc aataactgct attaatgttg aaaatgctaa caatgcttta    960
aaaatcagca atcttaatag taagggtagt aatgatttat ctgaaggaaa cttttgggcc   1020
aatgtccgca tttcagctga tatctgggga caaagtataa atatatatgg agacacaaaa   1080
ctaacaatgg atgttatagc tccaacacct gtaaatgtat caatcgcagc tatcccacaa   1140
agtagtactc acggttgggg aaatcctaca agagctatac gtgtttggac aaacaacttt   1200
gtagcacaaa ctgatggaac ctataaagca acttttgacca tttctacaaa cgatagtcca   1260
aatttcaata ctatagctac agatgctgct gatagtgtag taacaaatat gattctattt   1320
gttggttcaa attcagataa tatttcttta gacaatataa agtttactaa ataaggatcc   1380
ggctgctaac aaagcccgaa aggaagctga gttggctgct gccaccgctg agcaataact   1440
agcataaccc cttggggcct ctaa                                          1464

<210> SEQ ID NO 8
<211> LENGTH: 457
<212> TYPE: PRT
<213> ORGANISM: Artificial Sequence
<220> FEATURE:
<223> OTHER INFORMATION: Amino acid sequence for mCherry-CBM17 (Probe
      2b).
<220> FEATURE:
<221> NAME/KEY: misc_feature
<222> LOCATION: (245)..(245)
<223> OTHER INFORMATION: Glycine that links mCherry to CBM17.

<400> SEQUENCE: 8

Met Gly His His His His His His Gly Val Ser Lys Gly Glu Glu Asp
1               5                   10                  15
```

Asn Met Ala Ile Ile Lys Glu Phe Met Arg Phe Lys Val His Met Glu
            20                  25                  30

Gly Ser Val Asn Gly His Glu Phe Glu Ile Glu Gly Glu Gly Glu Gly
            35                  40                  45

Arg Pro Tyr Glu Gly Thr Gln Thr Ala Lys Leu Lys Val Thr Lys Gly
50                  55                  60

Gly Pro Leu Pro Phe Ala Trp Asp Ile Leu Ser Pro Gln Phe Met Tyr
65                  70                  75                  80

Gly Ser Lys Ala Tyr Val Lys His Pro Ala Asp Ile Pro Asp Tyr Leu
                85                  90                  95

Lys Leu Ser Phe Pro Glu Gly Phe Lys Trp Glu Arg Val Met Asn Phe
                100                 105                 110

Glu Asp Gly Gly Val Val Thr Val Thr Gln Asp Ser Ser Leu Gln Asp
            115                 120                 125

Gly Glu Phe Ile Tyr Lys Val Lys Leu Arg Gly Thr Asn Phe Pro Ser
130                 135                 140

Asp Gly Pro Val Met Gln Lys Lys Thr Met Gly Trp Glu Ala Ser Ser
145                 150                 155                 160

Glu Arg Met Tyr Pro Glu Asp Gly Ala Leu Lys Gly Glu Ile Lys Gln
                165                 170                 175

Arg Leu Lys Leu Lys Asp Gly Gly His Tyr Asp Ala Glu Val Lys Thr
            180                 185                 190

Thr Tyr Lys Ala Lys Lys Pro Val Gln Leu Pro Gly Ala Tyr Asn Val
            195                 200                 205

Asn Ile Lys Leu Asp Ile Thr Ser His Asn Glu Asp Tyr Thr Ile Val
            210                 215                 220

Glu Gln Tyr Glu Arg Ala Glu Gly Arg His Ser Thr Gly Gly Met Asp
225                 230                 235                 240

Glu Leu Tyr Lys Gly Leu Trp Ala Asp Asn Glu Leu Thr Thr Ser Gly
                245                 250                 255

Gln Tyr Val Arg Ala Arg Ile Lys Gly Ala Tyr Tyr Ala Thr Pro Val
            260                 265                 270

Asp Pro Val Thr Asn Gln Pro Thr Ala Pro Lys Asp Phe Ser Ser Gly
            275                 280                 285

Phe Trp Asp Phe Asn Asp Gly Thr Thr Gln Gly Phe Gly Val Asn Pro
290                 295                 300

Asp Ser Pro Ile Thr Ala Ile Asn Val Glu Asn Ala Asn Asn Ala Leu
305                 310                 315                 320

Lys Ile Ser Asn Leu Asn Ser Lys Gly Ser Asn Asp Leu Ser Glu Gly
                325                 330                 335

Asn Phe Trp Ala Asn Val Arg Ile Ser Ala Asp Ile Trp Gly Gln Ser
            340                 345                 350

Ile Asn Ile Tyr Gly Asp Thr Lys Leu Thr Met Asp Val Ile Ala Pro
            355                 360                 365

Thr Pro Val Asn Val Ser Ile Ala Ala Ile Pro Gln Ser Ser Thr His
            370                 375                 380

Gly Trp Gly Asn Pro Thr Arg Ala Ile Arg Val Trp Thr Asn Asn Phe
385                 390                 395                 400

Val Ala Gln Thr Asp Gly Thr Tyr Lys Ala Thr Leu Thr Ile Ser Thr
            405                 410                 415

Asn Asp Ser Pro Asn Phe Asn Thr Ile Ala Thr Ala Ala Asp Ser
            420                 425                 430

Val Val Thr Asn Met Ile Leu Phe Val Gly Ser Asn Ser Asp Asn Ile
    435                 440                 445

Ser Leu Asp Asn Ile Lys Phe Thr Lys
    450                 455

<210> SEQ ID NO 9
<211> LENGTH: 1224
<212> TYPE: DNA
<213> ORGANISM: Artificial Sequence
<220> FEATURE:
<223> OTHER INFORMATION: Nucleic acid sequence for mOrange2-CBM15 (Probe
      3).
<220> FEATURE:
<221> NAME/KEY: misc_feature
<222> LOCATION: (733)..(735)
<223> OTHER INFORMATION: Glycine codon that links mOrange2 to CBM15.

<400> SEQUENCE: 9
atgggtcatc accatcacca tcacggtgtg agcaagggcg aggagaataa catggccatc      60
atcaaggagt tcatgcgctt caaggtgcgc atggagggcc cgtgaacgg ccacgagttc     120 gagatcgagg gcgagggcga gggccgcccc tacgagggct tcagaccgc taagctgaag     180 gtgaccaagg gtggcccct gcccttcgcc tgggacatcc tgtcccctca tttcacctac     240
ggctccaagg cctacgtgaa gcaccccgcc gacatccccg actacttcaa gctgtccttc     300
cccgagggct tcaagtggga gcgcgtgatg aactacgagg acggcggcgt ggtgaccgtg     360
acccaggact cctccctgca ggacggcgag ttcatctaca aggtgaagct gcgcggcacc     420
aacttcccct ccgacggccc cgtgatgcag aagaagacca tgggctggga ggcctcctcc     480
gagcggatgt accccgagga cggtgccctg aagggcaaga tcaagatgag gctgaagctg     540
aaggacggcg ccactacac ctccgaggtc aagaccacct acaaggccaa gaagcccgtg     600
cagctgcccg gcgcctacat cgtcgacatc aagttggaca tcacctccca caacgaggac     660
tacaccatcg tggaacagta cgaacgcgcc gagggccgcc actccaccgg cggcatggac     720
gagctgtaca aggtgtcgc tgccagcgag ggcaatgttg ttatagaggt ggacatggca     780
aatggctgga gagcaacgc atcaggcagt accagccatt ccggtattac ctacagtgcc     840
gatggcgtta cctttgccgc actgggcgat ggcgtgggcg ctgtttttga tattgcccga     900
ccaaccacac tggaagatgc tgtgatagca atggttgtta atgtcagcgc tgaatttaag     960
gccagtgaag ccaacttgca gatatttgcc cagttaaaag aagactggtc aaagggcgaa    1020
tgggattgtc tggcggccag cagcgaactc actgcggata ctgacctaac cctgacctgc    1080
accattgatg aagacgacga taaattcaac caaacggcgc gcgatgtgca agtcggtatc    1140
caggccaagg gaacacccgc cggaactatc accattaaaa gcgtcaccat tacactcgca    1200
caggaagcct attcagccaa ttaa                                            1224

<210> SEQ ID NO 10
<211> LENGTH: 407
<212> TYPE: PRT
<213> ORGANISM: Artificial Sequence
<220> FEATURE:
<223> OTHER INFORMATION: Amino acid sequence for mOrange2-CBM15 (Probe
      3).
<220> FEATURE:
<221> NAME/KEY: misc_feature
<222> LOCATION: (245)..(245)
<223> OTHER INFORMATION: Glycine that links mOrange2 to CBM15.

<400> SEQUENCE: 10

Met Gly His His His His His Gly Val Ser Lys Gly Glu Glu Asn

```
  1               5                  10                 15
Asn Met Ala Ile Ile Lys Glu Phe Met Arg Phe Lys Val Arg Met Glu
             20                  25                 30

Gly Ser Val Asn Gly His Glu Phe Ile Glu Gly Glu Gly Glu Gly
             35                  40                 45

Arg Pro Tyr Glu Gly Phe Gln Thr Ala Lys Leu Lys Val Thr Lys Gly
     50                  55                 60

Gly Pro Leu Pro Phe Ala Trp Asp Ile Leu Ser Pro His Phe Thr Tyr
 65              70                  75                 80

Gly Ser Lys Ala Tyr Val Lys His Pro Ala Asp Ile Pro Asp Tyr Phe
                 85                  90                 95

Lys Leu Ser Phe Pro Glu Gly Phe Lys Trp Glu Arg Val Met Asn Tyr
             100                 105                110

Glu Asp Gly Gly Val Val Thr Val Thr Gln Asp Ser Ser Leu Gln Asp
             115                 120                125

Gly Glu Phe Ile Tyr Lys Val Lys Leu Arg Gly Thr Asn Phe Pro Ser
 130                 135                 140

Asp Gly Pro Val Met Gln Lys Lys Thr Met Gly Trp Glu Ala Ser Ser
145                 150                 155                160

Glu Arg Met Tyr Pro Glu Asp Gly Ala Leu Lys Gly Lys Ile Lys Met
                 165                 170                175

Arg Leu Lys Leu Lys Asp Gly Gly His Tyr Thr Ser Glu Val Lys Thr
             180                 185                 190

Thr Tyr Lys Ala Lys Lys Pro Val Gln Leu Pro Gly Ala Tyr Ile Val
         195                 200                 205

Asp Ile Lys Leu Asp Ile Thr Ser His Asn Glu Asp Tyr Thr Ile Val
210                 215                 220

Glu Gln Tyr Glu Arg Ala Glu Gly Arg His Ser Thr Gly Gly Met Asp
225                 230                 235                240

Glu Leu Tyr Lys Gly Val Ala Ala Ser Glu Gly Asn Val Val Ile Glu
             245                 250                 255

Val Asp Met Ala Asn Gly Trp Arg Gly Asn Ala Ser Gly Ser Thr Ser
         260                 265                 270

His Ser Gly Ile Thr Tyr Ser Ala Asp Gly Val Thr Phe Ala Ala Leu
         275                 280                 285

Gly Asp Gly Val Gly Ala Val Phe Asp Ile Ala Arg Pro Thr Thr Leu
     290                 295                 300

Glu Asp Ala Val Ile Ala Met Val Val Asn Val Ser Ala Glu Phe Lys
305                 310                 315                320

Ala Ser Glu Ala Asn Leu Gln Ile Phe Ala Gln Leu Lys Glu Asp Trp
                 325                 330                 335

Ser Lys Gly Glu Trp Asp Cys Leu Ala Ala Ser Ser Glu Leu Thr Ala
             340                 345                 350

Asp Thr Asp Leu Thr Leu Thr Cys Thr Ile Asp Glu Asp Asp Lys
             355                 360                 365

Phe Asn Gln Thr Ala Arg Asp Val Gln Val Gly Ile Gln Ala Lys Gly
 370                 375                 380

Thr Pro Ala Gly Thr Ile Thr Ile Lys Ser Val Thr Ile Thr Leu Ala
385                 390                 395                400

Gln Glu Ala Tyr Ser Ala Asn
                 405

<210> SEQ ID NO 11
```

-continued

```
<211> LENGTH: 1275
<212> TYPE: DNA
<213> ORGANISM: Artificial Sequence
<220> FEATURE:
<223> OTHER INFORMATION: Nucleic acid sequence for eCFP-CBM27 (Probe 4).
<220> FEATURE:
<221> NAME/KEY: misc_feature
<222> LOCATION: (742)..(744)
<223> OTHER INFORMATION: Glycine codon that links eCFP to CBM27.

<400> SEQUENCE: 11
atgggtcatc accatcacca tcacggtgtg agcaagggcg aggagctgtt caccggggtg      60
gtgcccatcc tggtcgagct ggacggcgac gtaaacggcc acaagttcag cgtgtccggc     120
gagggcgagg gcgatgccac ctacggcaag ctgaccctga agttcatctg caccaccggc     180
aagctgcccg tgccctggcc caccctcgtg accaccctga cctggggcgt gcagtgcttc     240
agccgctacc ccgaccacat gaagcagcac gacttcttca gtccgccat gcccgaaggc      300 tacgtccagg agcgcaccat cttcttcaag gacgacggca actacaagac ccgcgccgag     360
gtgaagttcg agggcgacac cctggtgaac cgcatcgagc tgaagggcat cgacttcaag     420
gaggacggca acatcctggg cacaagctg gagtacaact acatcagcca caacgtctat      480
atcaccgcca caagcagaa gaacggcatc aaggccaact tcaagatccg ccacaacatc      540
gaggacggca gcgtgcagct cgccgaccac taccagcaga cacccccat cggcgacggc      600 cccgtgctgc tgcccgacaa ccactacctg agcacccagt ccgccctgag caaagacccc     660
aacgagaagc gcgatcacat ggtcctgctg gagttcgtga ccgccgccgg gatcactctc     720
ggcatggacg agctgtacaa gggtaacgaa gcacggtacg tgctcgcaga ggaagttgat     780
ttttcctctc cagaagaggt gaaaaactgg tggaacagcg aacctggca ggcagagttc      840 gggtcacctg acattgaatg gaccggtgag gtgggaaatg gagcactgca gctgaacgtg     900
aaactgcccg gaaagagcga ctgggaagaa gtgagagtag caaggaagtt cgaaagactc     960
tcagaatgtg gatcctcga gtacgacatc tacattccaa cgtcgaggg actcaaggga     1020 aggttgaggc cgtacgcggt tctgaacccc ggctgggtga agataggcct cgacatgaac    1080
aacgcgaacg tggaaagtgc ggagatcatc actttcggcg aaaagagta cagaagattc    1140 catgtaagaa ttgagttcga cagaacagcg ggggtgaaag aacttcacat aggagttgtc    1200
ggtgatcatc tgaggtacga tggaccgatt ttcatcgata atgtgagact ttataaaaga    1260
acaggaggta tgtaa                                                     1275

<210> SEQ ID NO 12
<211> LENGTH: 424
<212> TYPE: PRT
<213> ORGANISM: Artificial Sequence
<220> FEATURE:
<223> OTHER INFORMATION: Amino acid sequence for eCFP-CBM27 (Probe 4).
<220> FEATURE:
<221> NAME/KEY: misc_feature
<222> LOCATION: (248)..(248)
<223> OTHER INFORMATION: Glycine that links eCFP to CBM27.

<400> SEQUENCE: 12

Met Gly His His His His His His Gly Val Ser Lys Gly Glu Glu Leu
1               5                   10                  15

Phe Thr Gly Val Val Pro Ile Leu Val Glu Leu Asp Gly Asp Val Asn
                20                  25                  30

Gly His Lys Phe Ser Val Ser Gly Glu Gly Glu Gly Asp Ala Thr Tyr
            35                  40                  45
```

```
Gly Lys Leu Thr Leu Lys Phe Ile Cys Thr Thr Gly Lys Leu Pro Val
 50                  55                  60

Pro Trp Pro Thr Leu Val Thr Leu Thr Trp Gly Val Gln Cys Phe
 65              70                  75                  80

Ser Arg Tyr Pro Asp His Met Lys Gln His Asp Phe Phe Lys Ser Ala
                 85                  90                  95

Met Pro Glu Gly Tyr Val Gln Glu Arg Thr Ile Phe Phe Lys Asp Asp
            100                 105                 110

Gly Asn Tyr Lys Thr Arg Ala Glu Val Lys Phe Glu Gly Asp Thr Leu
            115                 120                 125

Val Asn Arg Ile Glu Leu Lys Gly Ile Asp Phe Lys Glu Asp Gly Asn
130                 135                 140

Ile Leu Gly His Lys Leu Glu Tyr Asn Tyr Ile Ser His Asn Val Tyr
145                 150                 155                 160

Ile Thr Ala Asp Lys Gln Lys Asn Gly Ile Lys Ala Asn Phe Lys Ile
                165                 170                 175

Arg His Asn Ile Glu Asp Gly Ser Val Gln Leu Ala Asp His Tyr Gln
            180                 185                 190

Gln Asn Thr Pro Ile Gly Asp Gly Pro Val Leu Leu Pro Asp Asn His
            195                 200                 205

Tyr Leu Ser Thr Gln Ser Ala Leu Ser Lys Asp Pro Asn Glu Lys Arg
210                 215                 220

Asp His Met Val Leu Leu Glu Phe Val Thr Ala Ala Gly Ile Thr Leu
225                 230                 235                 240

Gly Met Asp Glu Leu Tyr Lys Gly Asn Glu Ala Arg Tyr Val Leu Ala
                245                 250                 255

Glu Glu Val Asp Phe Ser Ser Pro Glu Glu Val Lys Asn Trp Trp Asn
            260                 265                 270

Ser Gly Thr Trp Gln Ala Glu Phe Gly Ser Pro Asp Ile Glu Trp Asn
            275                 280                 285

Gly Glu Val Gly Asn Gly Ala Leu Gln Leu Asn Val Lys Leu Pro Gly
            290                 295                 300

Lys Ser Asp Trp Glu Glu Val Arg Val Ala Arg Lys Phe Glu Arg Leu
305                 310                 315                 320

Ser Glu Cys Glu Ile Leu Glu Tyr Asp Ile Tyr Ile Pro Asn Val Glu
                325                 330                 335

Gly Leu Lys Gly Arg Leu Arg Pro Tyr Ala Val Leu Asn Pro Gly Trp
            340                 345                 350

Val Lys Ile Gly Leu Asp Met Asn Asn Ala Asn Val Glu Ser Ala Glu
            355                 360                 365

Ile Ile Thr Phe Gly Gly Lys Glu Tyr Arg Arg Phe His Val Arg Ile
370                 375                 380

Glu Phe Asp Arg Thr Ala Gly Val Lys Glu Leu His Ile Gly Val Val
385                 390                 395                 400

Gly Asp His Leu Arg Tyr Asp Gly Pro Ile Phe Ile Asp Asn Val Arg
                405                 410                 415

Leu Tyr Lys Arg Thr Gly Gly Met
420
```

<210> SEQ ID NO 13
<211> LENGTH: 621
<212> TYPE: DNA
<213> ORGANISM: Artificial Sequence
<220> FEATURE:
<223> OTHER INFORMATION: Nucleic acid sequence for CBM3a.

<400> SEQUENCE: 13

```
atgggtcatc accatcacca tcacggtaca ccgaccaagg gagcaacacc aacaaataca    60
gctacgccga caaatcagc tacggctacg cccaccaggc catcggtacc gacaaacaca   120
ccgacaaaca caccggcaaa tacaccggta tcaggcaatt tgaaggttga attctacaac   180
agcaatcctt cagatactac taactcaatc aatcctcagt tcaaggttac taataccgga   240
agcagtgcaa ttgatttgtc caaactcaca ttgagatatt attatacagt agacggacag   300
aaagatcaga ccttctggtg tgaccatgct gcaataatcg gcagtaacgg cagctacaac   360
ggaattactt caaatgtaaa aggaacattt gtaaaaatga gttcctcaac aaataacgca   420
gacacctacc ttgaaattag ctttacaggc ggaactcttg aaccgggtgc acatgttcag   480
atacaaggta gatttgcaaa gaatgactgg agtaactata cacagtcaaa tgactactca   540
ttcaagtctg cttcacagtt tgttgaatgg gatcaggtaa cagcatactt gaacggtgtt   600
cttgtatggg gtaaagaata a                                             621
```

<210> SEQ ID NO 14
<211> LENGTH: 206
<212> TYPE: PRT
<213> ORGANISM: Artificial Sequence
<220> FEATURE:
<223> OTHER INFORMATION: Amino acid sequence for CBM3a.

<400> SEQUENCE: 14

```
Met Gly His His His His His His Gly Thr Pro Thr Lys Gly Ala Thr
1               5                   10                  15

Pro Thr Asn Thr Ala Thr Pro Thr Lys Ser Ala Thr Ala Thr Pro Thr
            20                  25                  30

Arg Pro Ser Val Pro Thr Asn Thr Pro Thr Asn Thr Pro Ala Asn Thr
        35                  40                  45

Pro Val Ser Gly Asn Leu Lys Val Glu Phe Tyr Asn Ser Asn Pro Ser
    50                  55                  60

Asp Thr Thr Asn Ser Ile Asn Pro Gln Phe Lys Val Thr Asn Thr Gly
65                  70                  75                  80

Ser Ser Ala Ile Asp Leu Ser Lys Leu Thr Leu Arg Tyr Tyr Tyr Thr
                85                  90                  95

Val Asp Gly Gln Lys Asp Gln Thr Phe Trp Cys Asp His Ala Ala Ile
            100                 105                 110

Ile Gly Ser Asn Gly Ser Tyr Asn Gly Ile Thr Ser Asn Val Lys Gly
        115                 120                 125

Thr Phe Val Lys Met Ser Ser Ser Thr Asn Asn Ala Asp Thr Tyr Leu
    130                 135                 140

Glu Ile Ser Phe Thr Gly Gly Thr Leu Glu Pro Gly Ala His Val Gln
145                 150                 155                 160

Ile Gln Gly Arg Phe Ala Lys Asn Asp Trp Ser Asn Tyr Thr Gln Ser
                165                 170                 175

Asn Asp Tyr Ser Phe Lys Ser Ala Ser Gln Phe Val Glu Trp Asp Gln
            180                 185                 190

Val Thr Ala Tyr Leu Asn Gly Val Leu Val Trp Gly Lys Glu
        195                 200                 205
```

<210> SEQ ID NO 15
<211> LENGTH: 486
<212> TYPE: DNA
<213> ORGANISM: Artificial Sequence

```
<220> FEATURE:
<223> OTHER INFORMATION: Nucleic acid sequence for CBM4-1.

<400> SEQUENCE: 15
atgggtcatc accatcacca tcacggtgcg tcgccgatcg gggagggaac gttcgacgac      60
gggcccgagg ggtgggtcgc gtacggcacc gacggccccc tcgacacgag cacgggcgcg    120
ctgtgcgtcg ccgtgccggc cggctccgcg cagtacggcg tcggcgtcgt gctcaacggc    180
gtcgcgatcg aggaagggac cacctacacg ctccggtaca ccgcgacggc ctcgaccgac    240
gtcaccgtgc gggcgctcgt cgggcagaac ggcgcccccct acggcaccgt gctcgacacg    300
agcccggccc tgacgtccga ccgcggcag gtgaccgaga cgttcacggc ctcggcgacg    360
taccccgcga cacccgccgc cgacgacccc gaggggcaga tcgccttcca gctcggcggg    420
ttcagcgccg acgcgtggac gttctgcctc gacgacgtcg cgctcgactc cgaggtcgag    480
ctctaa                                                               486

<210> SEQ ID NO 16
<211> LENGTH: 161
<212> TYPE: PRT
<213> ORGANISM: Artificial Sequence
<220> FEATURE:
<223> OTHER INFORMATION: Amino acid sequence for CBM4-1.

<400> SEQUENCE: 16

Met Gly His His His His His His Gly Ala Ser Pro Ile Gly Glu Gly
 1               5                  10                  15

Thr Phe Asp Asp Gly Pro Glu Gly Trp Val Ala Tyr Gly Thr Asp Gly
            20                  25                  30

Pro Leu Asp Thr Ser Thr Gly Ala Leu Cys Val Ala Val Pro Ala Gly
        35                  40                  45

Ser Ala Gln Tyr Gly Val Gly Val Val Leu Asn Gly Val Ala Ile Glu
    50                  55                  60

Glu Gly Thr Thr Tyr Thr Leu Arg Tyr Thr Ala Thr Ala Ser Thr Asp
65                  70                  75                  80

Val Thr Val Arg Ala Leu Val Gly Gln Asn Gly Ala Pro Tyr Gly Thr
                85                  90                  95

Val Leu Asp Thr Ser Pro Ala Leu Thr Ser Glu Pro Arg Gln Val Thr
            100                 105                 110

Glu Thr Phe Thr Ala Ser Ala Thr Tyr Pro Ala Thr Pro Ala Ala Asp
        115                 120                 125

Asp Pro Glu Gly Gln Ile Ala Phe Gln Leu Gly Gly Phe Ser Ala Asp
    130                 135                 140

Ala Trp Thr Phe Cys Leu Asp Asp Val Ala Leu Asp Ser Glu Val Glu
145                 150                 155                 160

Leu

<210> SEQ ID NO 17
<211> LENGTH: 666
<212> TYPE: DNA
<213> ORGANISM: Artificial Sequence
<220> FEATURE:
<223> OTHER INFORMATION: Nucleic acid sequence for CBM17.

<400> SEQUENCE: 17
atgggtcatc accatcacca tcacggttta tgggcagata tgaattaac cacttcaggt      60 caatatgtac gtgctcgtat taagggagct tattatgcta caccagttga tcctgtaaca    120
```

-continued

```
aaccaaccaa cagcaccgaa agactttcct tcaggctttt gggactttaa tgacggtact    180
acacaaggtt ttggtgtaaa tccagatagt ccataactg ctattaatgt tgaaaatgct    240
aacaatgctt taaaaatcag caatcttaat agtaagggta gtaatgattt atctgaagga    300
aacttttggg ccaatgtccg catttcagct gatatctggg gacaaagtat aaatatatat    360
ggagacacaa actaacaat ggatgttata gctccaacac ctgtaaatgt atcaatcgca    420
gctatcccac aaagtagtac tcacggttgg ggaaatccta aagagctat acgtgtttgg    480 acaaacaact ttgtagcaca aactgatgga acctataaag caactttgac catttctaca    540
aacgatagtc caaatttcaa tactatagct acagatgctg ctgatagtgt agtaacaaat    600
atgattctat ttgttggttc aaattcagat aatatttctt tagacaatat aaagtttact    660
aaataa                                                              666
```

<210> SEQ ID NO 18
<211> LENGTH: 221
<212> TYPE: PRT
<213> ORGANISM: Artificial Sequence
<220> FEATURE:
<223> OTHER INFORMATION: Amino acid sequence for CBM17.

<400> SEQUENCE: 18

```
Met Gly His His His His His His Gly Leu Trp Ala Asp Asn Glu Leu
1               5                   10                  15

Thr Thr Ser Gly Gln Tyr Val Arg Ala Arg Ile Lys Gly Ala Tyr Tyr
            20                  25                  30

Ala Thr Pro Val Asp Pro Val Thr Asn Gln Pro Thr Ala Pro Lys Asp
        35                  40                  45

Phe Ser Ser Gly Phe Trp Asp Phe Asn Asp Gly Thr Thr Gln Gly Phe
    50                  55                  60

Gly Val Asn Pro Asp Ser Pro Ile Thr Ala Ile Asn Val Glu Asn Ala
65                  70                  75                  80

Asn Asn Ala Leu Lys Ile Ser Asn Leu Asn Ser Lys Gly Ser Asn Asp
                85                  90                  95

Leu Ser Glu Gly Asn Phe Trp Ala Asn Val Arg Ile Ser Ala Asp Ile
            100                 105                 110

Trp Gly Gln Ser Ile Asn Ile Tyr Gly Asp Thr Lys Leu Thr Met Asp
        115                 120                 125

Val Ile Ala Pro Thr Pro Val Asn Val Ser Ile Ala Ala Ile Pro Gln
    130                 135                 140

Ser Ser Thr His Gly Trp Gly Asn Pro Thr Arg Ala Ile Arg Val Trp
145                 150                 155                 160

Thr Asn Asn Phe Val Ala Gln Thr Asp Gly Thr Tyr Lys Ala Thr Leu
                165                 170                 175

Thr Ile Ser Thr Asn Asp Ser Pro Asn Phe Asn Thr Ile Ala Thr Asp
            180                 185                 190

Ala Ala Asp Ser Val Val Thr Asn Met Ile Leu Phe Val Gly Ser Asn
        195                 200                 205

Ser Asp Asn Ile Ser Leu Asp Asn Ile Lys Phe Thr Lys
    210                 215                 220
```

<210> SEQ ID NO 19
<211> LENGTH: 516
<212> TYPE: DNA
<213> ORGANISM: Artificial Sequence
<220> FEATURE:
<223> OTHER INFORMATION: Nucleic acid sequence for CBM15.

<400> SEQUENCE: 19

```
atgggtcatc accatcacca tcacggtgtc gctgccagcg agggcaatgt tgttatagag      60
gtggacatgg caaatggctg gagaggcaac gcatcaggca gtaccagcca ttccggtatt     120
acctacagtg ccgatggcgt tacctttgcc gcactgggcg atggcgtggg cgctgttttt     180
gatattgccc gaccaaccac actggaagat gctgtgatag caatggttgt taatgtcagc     240
gctgaattta aggccagtga agccaacttg cagatatttg cccagttaaa agaagactgg     300
tcaaagggcg aatgggattg tctggcggcc agcagcgaac tcactgcgga tactgaccta     360
accctgacct gcaccattga tgaagacgac gataaattca accaaacggc gcgcgatgta     420
caagtcggta tccaggccaa gggaacaccc gccggaacta tcaccattaa aagcgtcacc     480
attacactcg cacaggaagc ctattcagcc aattaa                               516
```

<210> SEQ ID NO 20
<211> LENGTH: 171
<212> TYPE: PRT
<213> ORGANISM: Artificial Sequence
<220> FEATURE:
<223> OTHER INFORMATION: Amino acid sequence for CBM15.

<400> SEQUENCE: 20

```
Met Gly His His His His His His Gly Val Ala Ala Ser Glu Gly Asn
1               5                   10                  15

Val Val Ile Glu Val Asp Met Ala Asn Gly Trp Arg Gly Asn Ala Ser
            20                  25                  30

Gly Ser Thr Ser His Ser Gly Ile Thr Tyr Ser Ala Asp Gly Val Thr
        35                  40                  45

Phe Ala Ala Leu Gly Asp Gly Val Gly Ala Val Phe Asp Ile Ala Arg
    50                  55                  60

Pro Thr Thr Leu Glu Asp Ala Val Ile Ala Met Val Val Asn Val Ser
65                  70                  75                  80

Ala Glu Phe Lys Ala Ser Glu Ala Asn Leu Gln Ile Phe Ala Gln Leu
                85                  90                  95

Lys Glu Asp Trp Ser Lys Gly Glu Trp Asp Cys Leu Ala Ala Ser Ser
            100                 105                 110

Glu Leu Thr Ala Asp Thr Asp Leu Thr Leu Thr Cys Thr Ile Asp Glu
        115                 120                 125

Asp Asp Asp Lys Phe Asn Gln Thr Ala Arg Asp Val Gln Val Gly Ile
    130                 135                 140

Gln Ala Lys Gly Thr Pro Ala Gly Thr Ile Thr Ile Lys Ser Val Thr
145                 150                 155                 160

Ile Thr Leu Ala Gln Glu Ala Tyr Ser Ala Asn
                165                 170
```

<210> SEQ ID NO 21
<211> LENGTH: 558
<212> TYPE: DNA
<213> ORGANISM: Artificial Sequence
<220> FEATURE:
<223> OTHER INFORMATION: Nucleic acid sequence for CBM27.

<400> SEQUENCE: 21

```
atgggtcatc accatcacca tcacggtaac gaagcacggt acgtgctcgc agaggaagtt      60 gattttcct ctccagaaga ggtgaaaaac tggtggaaca gcggaacctg caggcagag      120 ttcgggtcac ctgacattga atggaacggt gaggtgggaa atggagcact gcagctgaac     180
```

```
gtgaaactgc ccggaaagag cgactgggaa gaagtgagag tagcaaggaa gttcgaaaga    240
ctctcagaat gtgagatcct cgagtacgac atctacattc caaacgtcga gggactcaag    300
ggaaggttga ggccgtacgc ggttctgaac cccggctggg tgaagatagg cctcgacatg    360
aacaacgcga acgtgaaaag tgcggagatc atcactttcg gcggaaaaga gtacagaaga    420
ttccatgtaa gaattgagtt cgacagaaca gcggggggtga agaacttca cataggagtt    480 gtcggtgatc atctgaggta cgatggaccg attttcatcg ataatgtgag actttataaa    540
agaacaggag gtatgtaa                                                   558
```

```
<210> SEQ ID NO 22
<211> LENGTH: 185
<212> TYPE: PRT
<213> ORGANISM: Artificial Sequence
<220> FEATURE:
<223> OTHER INFORMATION: Amino acid sequence for CBM27.

<400> SEQUENCE: 22

Met Gly His His His His His His Gly Asn Glu Ala Arg Tyr Val Leu
 1               5                  10                  15

Ala Glu Glu Val Asp Phe Ser Ser Pro Glu Glu Val Lys Asn Trp Trp
            20                  25                  30

Asn Ser Gly Thr Trp Gln Ala Glu Phe Gly Ser Pro Asp Ile Glu Trp
        35                  40                  45

Asn Gly Glu Val Gly Asn Gly Ala Leu Gln Leu Asn Val Lys Leu Pro
    50                  55                  60

Gly Lys Ser Asp Trp Glu Val Arg Val Ala Arg Lys Phe Glu Arg
65                  70                  75                  80

Leu Ser Glu Cys Glu Ile Leu Glu Tyr Asp Ile Tyr Ile Pro Asn Val
                85                  90                  95

Glu Gly Leu Lys Gly Arg Leu Arg Pro Tyr Ala Val Leu Asn Pro Gly
            100                 105                 110

Trp Val Lys Ile Gly Leu Asp Met Asn Asn Ala Asn Val Glu Ser Ala
        115                 120                 125

Glu Ile Ile Thr Phe Gly Gly Lys Glu Tyr Arg Arg Phe His Val Arg
    130                 135                 140

Ile Glu Phe Asp Arg Thr Ala Gly Val Lys Glu Leu His Ile Gly Val
145                 150                 155                 160

Val Gly Asp His Leu Arg Tyr Asp Gly Pro Ile Phe Ile Asp Asn Val
                165                 170                 175

Arg Leu Tyr Lys Arg Thr Gly Gly Met
            180                 185
```

```
<210> SEQ ID NO 23
<211> LENGTH: 744
<212> TYPE: DNA
<213> ORGANISM: Artificial Sequence
<220> FEATURE:
<223> OTHER INFORMATION: Nucleic acid sequence for eGFP.

<400> SEQUENCE: 23
atgggtcatc accatcacca tcacggtgtg agcaagggcg aggagctgtt caccggggtg     60
gtgcccatcc tggtcgagct ggacggcgac gtaaacggcc acaagttcag cgtgtccggc    120
gagggcgagg gcgatgccac ctacggcaag ctgaccctga agttcatctg caccaccggc    180
aagctgcccg tgccctggcc caccctcgtg accaccctga cctacggcgt gcagtgcttc    240
```

```
agccgctacc ccgaccacat gaagcagcac gacttcttca agtccgccat gcccgaaggc    300
tacgtccagg agcgcaccat cttcttcaag gacgacggca actacaagac ccgcgccgag    360
gtgaagttcg agggcgacac cctggtgaac cgcatcgagc tgaagggcat cgacttcaag    420
gaggacggca acatcctggg gcacaagctg gagtacaact acaacagcca caacgtctat    480
atcatggccg acaagcagaa gaacggcatc aaggtgaact tcaagatccg ccacaacatc    540
gaggacggca gcgtgcagct cgccgaccac taccagcaga caccccccat cggcgacggc    600
cccgtgctgc tgcccgacaa ccactacctg agcacccagt ccgccctgag caaagacccc    660
aacgagaagc gcgatcacat ggtcctgctg gagttcgtga ccgccgccgg gatcactctc    720
ggcatggacg agctgtacaa gtaa                                            744
```

<210> SEQ ID NO 24
<211> LENGTH: 247
<212> TYPE: PRT
<213> ORGANISM: Artificial Sequence
<220> FEATURE:
<223> OTHER INFORMATION: Amino acid sequence for eGFP.

<400> SEQUENCE: 24

```
Met Gly His His His His His His Gly Val Ser Lys Gly Glu Glu Leu
1               5                  10                  15

Phe Thr Gly Val Val Pro Ile Leu Val Glu Leu Asp Gly Asp Val Asn
            20                  25                  30

Gly His Lys Phe Ser Val Ser Gly Glu Gly Glu Gly Asp Ala Thr Tyr
        35                  40                  45

Gly Lys Leu Thr Leu Lys Phe Ile Cys Thr Thr Gly Lys Leu Pro Val
    50                  55                  60

Pro Trp Pro Thr Leu Val Thr Thr Leu Thr Tyr Gly Val Gln Cys Phe
65                  70                  75                  80

Ser Arg Tyr Pro Asp His Met Lys Gln His Asp Phe Phe Lys Ser Ala
                85                  90                  95

Met Pro Glu Gly Tyr Val Gln Glu Arg Thr Ile Phe Phe Lys Asp Asp
            100                 105                 110

Gly Asn Tyr Lys Thr Arg Ala Glu Val Lys Phe Glu Gly Asp Thr Leu
        115                 120                 125

Val Asn Arg Ile Glu Leu Lys Gly Ile Asp Phe Lys Glu Asp Gly Asn
    130                 135                 140

Ile Leu Gly His Lys Leu Glu Tyr Asn Tyr Asn Ser His Asn Val Tyr
145                 150                 155                 160

Ile Met Ala Asp Lys Gln Lys Asn Gly Ile Lys Val Asn Phe Lys Ile
                165                 170                 175

Arg His Asn Ile Glu Asp Gly Ser Val Gln Leu Ala Asp His Tyr Gln
            180                 185                 190

Gln Asn Thr Pro Ile Gly Asp Gly Pro Val Leu Leu Pro Asp Asn His
        195                 200                 205

Tyr Leu Ser Thr Gln Ser Ala Leu Ser Lys Asp Pro Asn Glu Lys Arg
    210                 215                 220

Asp His Met Val Leu Leu Glu Phe Val Thr Ala Ala Gly Ile Thr Leu
225                 230                 235                 240

Gly Met Asp Glu Leu Tyr Lys
                245
```

<210> SEQ ID NO 25
<211> LENGTH: 735

<212> TYPE: DNA
<213> ORGANISM: Artificial Sequence
<220> FEATURE:
<223> OTHER INFORMATION: Nucleic acid sequence for mCherry.

<400> SEQUENCE: 25

```
atgggtcatc accatcacca tcacggtgtg agcaagggcg aggaggataa catggccatc      60
atcaaggagt tcatgcgctt caaggtgcac atggagggct ccgtgaacgg ccacgagttc     120
gagatcgagg gcgagggcga gggccgcccc tacgagggca cccagaccgc caagctgaag     180
gtgaccaagg gtggccccct gcccttcgcc tgggacatcc tgtcccctca gttcatgtac     240
ggctccaagg cctacgtgaa gcaccccgcc gacatccccg actacttgaa gctgtccttc     300
cccgagggct tcaagtggga gcgcgtgatg aacttcgagg acggcggcgt ggtgaccgtg     360
acccaggact cctccctgca ggacggcgag ttcatctaca aggtgaagct gcgcggcacc     420
aacttcccct ccgacggccc cgtaatgcag aagaagacca tgggctggga ggcctcctcc     480
gagcggatgt accccgagga cggcgccctg aaggccgaga tcaagcagag gctgaagctg     540
aaggacggcg gccactacga cgctgaggtc aagaccacct acaaggccaa gaagcccgtg     600
cagctgcccg gcgcctacaa cgtcaacatc aagttggaca tcacctccca caacgaggac     660
tacaccatcg tggaacagta cgaacgcgcc gagggccgcc actccaccgg cggcatggac     720
gagctgtaca agtaa                                                      735
```

<210> SEQ ID NO 26
<211> LENGTH: 244
<212> TYPE: PRT
<213> ORGANISM: Artificial Sequence
<220> FEATURE:
<223> OTHER INFORMATION: Amino acid sequence for mCherry.

<400> SEQUENCE: 26

```
Met Gly His His His His His Gly Val Ser Lys Gly Glu Glu Asp
1               5                   10                  15

Asn Met Ala Ile Ile Lys Glu Phe Met Arg Phe Lys Val His Met Glu
            20                  25                  30

Gly Ser Val Asn Gly His Glu Phe Glu Ile Glu Gly Glu Gly Glu Gly
        35                  40                  45

Arg Pro Tyr Glu Gly Thr Gln Thr Ala Lys Leu Lys Val Thr Lys Gly
    50                  55                  60

Gly Pro Leu Pro Phe Ala Trp Asp Ile Leu Ser Pro Gln Phe Met Tyr
65                  70                  75                  80

Gly Ser Lys Ala Tyr Val Lys His Pro Ala Asp Ile Pro Asp Tyr Leu
                85                  90                  95

Lys Leu Ser Phe Pro Glu Gly Phe Lys Trp Glu Arg Val Met Asn Phe
            100                 105                 110

Glu Asp Gly Gly Val Val Thr Val Thr Gln Asp Ser Ser Leu Gln Asp
        115                 120                 125

Gly Glu Phe Ile Tyr Lys Val Lys Leu Arg Gly Thr Asn Phe Pro Ser
    130                 135                 140

Asp Gly Pro Val Met Gln Lys Lys Thr Met Gly Trp Glu Ala Ser Ser
145                 150                 155                 160

Glu Arg Met Tyr Pro Glu Asp Gly Ala Leu Lys Gly Glu Ile Lys Gln
                165                 170                 175

Arg Leu Lys Leu Lys Asp Gly Gly His Tyr Asp Ala Glu Val Lys Thr
            180                 185                 190
```

```
Thr Tyr Lys Ala Lys Lys Pro Val Gln Leu Pro Gly Ala Tyr Asn Val
            195                 200                 205

Asn Ile Lys Leu Asp Ile Thr Ser His Asn Glu Asp Tyr Thr Ile Val
        210                 215                 220

Glu Gln Tyr Glu Arg Ala Glu Gly Arg His Ser Thr Gly Gly Met Asp
225                 230                 235                 240

Glu Leu Tyr Lys
```

<210> SEQ ID NO 27
<211> LENGTH: 735
<212> TYPE: DNA
<213> ORGANISM: Artificial Sequence
<220> FEATURE:
<223> OTHER INFORMATION: Nucleic acid sequence for mOrange2.

<400> SEQUENCE: 27

```
atgggtcatc accatcacca tcacggtgtg agcaagggcg aggagaataa catggccatc      60
atcaaggagt tcatgcgctt caaggtgcgc atggagggct ccgtgaacgg ccacgagttc     120
gagatcgagg gcgagggcga gggccgcccc tacgagggct tcagaccgc taagctgaag     180
gtgaccaagg gtggcccct gcccttcgcc tgggacatcc tgtcccctca tttcacctac     240
ggctccaagg cctacgtgaa gcaccccgcc gacatccccg actacttcaa gctgtccttc     300
cccgagggct tcaagtggga gcgcgtgatg aactacgagg acggcggcgt ggtgaccgtg     360
acccaggact cctccctgca ggacggcgag ttcatctaca aggtgaagct gcgcggcacc     420
aacttcccct ccgacggccc cgtgatgcag aagaagacca tgggctggga ggcctcctcc     480
gagcggatgt accccgagga cggtgccctg aagggcaaga tcaagatgag gctgaagctg     540
aaggacggcg gccactacac ctccgaggtc aagaccacct acaaggccaa gaagcccgtg     600
cagctgcccg gcgcctacat cgtcgacatc aagttggaca tcacctccca caacgaggac     660
tacaccatcg tggaacagta cgaacgcgcc gagggccgcc actccaccgg cggcatggac     720
gagctgtaca agtaa                                                      735
```

<210> SEQ ID NO 28
<211> LENGTH: 244
<212> TYPE: PRT
<213> ORGANISM: Artificial Sequence
<220> FEATURE:
<223> OTHER INFORMATION: Amino acid sequence for mOrange2.

<400> SEQUENCE: 28

```
Met Gly His His His His His His Gly Val Ser Lys Gly Glu Glu Asn
1               5                   10                  15

Asn Met Ala Ile Ile Lys Glu Phe Met Arg Phe Lys Val Arg Met Glu
            20                  25                  30

Gly Ser Val Asn Gly His Glu Phe Glu Ile Glu Gly Glu Gly Glu Gly
        35                  40                  45

Arg Pro Tyr Glu Gly Phe Gln Thr Ala Lys Leu Lys Val Thr Lys Gly
    50                  55                  60

Gly Pro Leu Pro Phe Ala Trp Asp Ile Leu Ser Pro His Phe Thr Tyr
65                  70                  75                  80

Gly Ser Lys Ala Tyr Val Lys His Pro Ala Asp Ile Pro Asp Tyr Phe
                85                  90                  95

Lys Leu Ser Phe Pro Glu Gly Phe Lys Trp Glu Arg Val Met Asn Tyr
            100                 105                 110

Glu Asp Gly Gly Val Val Thr Val Thr Gln Asp Ser Ser Leu Gln Asp
```

```
            115                 120                 125
Gly Glu Phe Ile Tyr Lys Val Lys Leu Arg Gly Thr Asn Phe Pro Ser
    130                 135                 140

Asp Gly Pro Val Met Gln Lys Lys Thr Met Gly Trp Glu Ala Ser Ser
145                 150                 155                 160

Glu Arg Met Tyr Pro Glu Asp Gly Ala Leu Lys Gly Lys Ile Lys Met
                165                 170                 175

Arg Leu Lys Leu Lys Asp Gly Gly His Tyr Thr Ser Glu Val Lys Thr
            180                 185                 190

Thr Tyr Lys Ala Lys Lys Pro Val Gln Leu Pro Gly Ala Tyr Ile Val
        195                 200                 205

Asp Ile Lys Leu Asp Ile Thr Ser His Asn Glu Asp Tyr Thr Ile Val
    210                 215                 220

Glu Gln Tyr Glu Arg Ala Glu Gly Arg His Ser Thr Gly Gly Met Asp
225                 230                 235                 240

Glu Leu Tyr Lys

<210> SEQ ID NO 29
<211> LENGTH: 744
<212> TYPE: DNA
<213> ORGANISM: Artificial Sequence
<220> FEATURE:
<223> OTHER INFORMATION: Nucleic acid sequence for eCFP.

<400> SEQUENCE: 29
atgggtcatc accatcacca tcacggtgtg agcaagggcg aggagctgtt caccggggtg      60
gtgcccatcc tggtcgagct ggacggcgac gtaaacggcc acaagttcag cgtgtccggc     120
gagggcgagg gcgatgccac ctacggcaag ctgaccctga agttcatctg caccaccggc     180
aagctgcccg tgccctggcc caccctcgtg accaccctga cctggggcgt gcagtgcttc     240
agccgctacc ccgaccacat gaagcagcac gacttcttca agtccgccat gcccgaaggc     300
tacgtccagg agcgcaccat cttcttcaag gacgacggca actacaagac ccgcgccgag     360
gtgaagttcg agggcgacac cctggtgaac cgcatcgagc tgaagggcat cgacttcaag     420
gaggacggca acatcctggg gcacaagctg gagtacaact acatcagcca caacgtctat     480
atcaccgccg acaagcagaa gaacggcatc aaggccaact tcaagatccg ccacaacatc     540
gaggacggca gcgtgcagct cgccgaccac taccagcaga caccccccat cggcgacggc     600
cccgtgctgc tgcccgacaa ccactacctg agcacccagt ccgccctgag caaagacccc     660
aacgagaagc gcgatcacat ggtcctgctg gagttcgtga ccgccgccgg gatcactctc     720
ggcatggacg agctgtacaa gtaa                                            744

<210> SEQ ID NO 30
<211> LENGTH: 247
<212> TYPE: PRT
<213> ORGANISM: Artificial Sequence
<220> FEATURE:
<223> OTHER INFORMATION: Amino acid sequence for eCFP.

<400> SEQUENCE: 30

Met Gly His His His His His His Gly Val Ser Lys Gly Glu Glu Leu
1               5                   10                  15

Phe Thr Gly Val Val Pro Ile Leu Val Glu Leu Asp Gly Asp Val Asn
            20                  25                  30

Gly His Lys Phe Ser Val Ser Gly Glu Gly Glu Gly Asp Ala Thr Tyr
        35                  40                  45
```

```
Gly Lys Leu Thr Leu Lys Phe Ile Cys Thr Thr Gly Lys Leu Pro Val
    50                  55                  60

Pro Trp Pro Thr Leu Val Thr Thr Leu Thr Trp Gly Val Gln Cys Phe
65              70                  75                      80

Ser Arg Tyr Pro Asp His Met Lys Gln His Asp Phe Phe Lys Ser Ala
            85                  90                  95

Met Pro Glu Gly Tyr Val Gln Glu Arg Thr Ile Phe Phe Lys Asp Asp
            100             105                 110

Gly Asn Tyr Lys Thr Arg Ala Glu Val Lys Phe Glu Gly Asp Thr Leu
        115             120                 125

Val Asn Arg Ile Glu Leu Lys Gly Ile Asp Phe Lys Glu Asp Gly Asn
    130             135                 140

Ile Leu Gly His Lys Leu Glu Tyr Asn Tyr Ile Ser His Asn Val Tyr
145             150                 155                 160

Ile Thr Ala Asp Lys Gln Lys Asn Gly Ile Lys Ala Asn Phe Lys Ile
            165             170                 175

Arg His Asn Ile Glu Asp Gly Ser Val Gln Leu Ala Asp His Tyr Gln
            180             185                 190

Gln Asn Thr Pro Ile Gly Asp Gly Pro Val Leu Leu Pro Asp Asn His
        195             200             205

Tyr Leu Ser Thr Gln Ser Ala Leu Ser Lys Asp Pro Asn Glu Lys Arg
    210             215             220

Asp His Met Val Leu Leu Glu Phe Val Thr Ala Ala Gly Ile Thr Leu
225             230             235             240

Gly Met Asp Glu Leu Tyr Lys
            245
```